(12) United States Patent
Alexander et al.

(10) Patent No.: US 9,890,174 B2
(45) Date of Patent: Feb. 13, 2018

(54) FUSED TRICYCLIC IMIDAZOLE DERIVATIVES AS MODULATORS OF TNF ACTIVITY

(71) Applicant: UCB BIOPHARMA SPRL, Brussels (BE)

(72) Inventors: Rikki Peter Alexander, Slough (GB); Julien Alistair Brown, Slough (GB); Michael Deligny, Brussels (BE); Jag Paul Heer, Brussels (BE); Victoria Elizabeth Jackson, Slough (GB); Sophie Jadot, Brussels (BE); Boris Kroeplien, Slough (GB); Malcolm Mac Coss, Seabrook Island, SC (US); Yogesh Anil Sabnis, Brussels (BE); Dominique Louis Léon Swinnen, Brussels (BE); Nathalie Van Houtvin, Brussels (BE); Zhaoning Zhu, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/101,798

(22) PCT Filed: Dec. 8, 2014

(86) PCT No.: PCT/EP2014/076886
§ 371 (c)(1),
(2) Date: Jun. 3, 2016

(87) PCT Pub. No.: WO2015/086527
PCT Pub. Date: Jun. 18, 2015

(65) Prior Publication Data
US 2016/0304530 A1    Oct. 20, 2016

(30) Foreign Application Priority Data
Dec. 9, 2013  (GB) .................................. 1321730.2

(51) Int. Cl.
| | | |
|---|---|---|
| C07D 491/14 | (2006.01) | |
| C07D 471/04 | (2006.01) | |
| A61K 31/437 | (2006.01) | |
| A61K 31/4375 | (2006.01) | |
| C07D 491/147 | (2006.01) | |
| C07D 471/14 | (2006.01) | |

(52) U.S. Cl.
CPC ....... *C07D 491/147* (2013.01); *C07D 471/04* (2013.01); *C07D 471/14* (2013.01); *C07D 491/14* (2013.01)

(58) Field of Classification Search
None
See application file for complete search history.

(56) References Cited

U.S. PATENT DOCUMENTS 7,641,703 B2 * 1/2010 Guerin ................ A61K 8/49
8/405

FOREIGN PATENT DOCUMENTS

| WO | 03/014123 A1  | 2/2003  |
|----|---------------|---------|
| WO | 04/014900 A1  | 2/2004  |
| WO | 13/186229 A1  | 12/2013 |
| WO | 14/009295 A1  | 1/2014  |
| WO | 14/009296 A1  | 1/2014  |

OTHER PUBLICATIONS

El Bousmaqui et al, Heterocycles, 85(9), pp. 2135-2145, published online Jul. 25, 2012.*
Ryabukhin et al, Monatshefte fuer Chemie, 143(11), pp. 1507-1517, published online Jul. 18, 2012.*
Tansey et al., "The TNF superfamily in 2009: new pathways, new indications, and new drugs", Drug Discovery Today, 2009, 14(23/24), 1082-1088.
Carneiro et al., "Emerging Role for TNF-α in Erectile Dysfunction", J. Sexual Medicine, 2010, vol. 7, 3823-3834.
Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.

* cited by examiner

*Primary Examiner* — Zinna Northington-Davis
(74) *Attorney, Agent, or Firm* — McDonnell Boehnen Hulbert & Berghoff LLP

(57) ABSTRACT

A series of substituted fused tricyclic imidazole derivatives, in particular dihydro-1H-pyrano[4',3':4,5]imidazo[1,2-a]pyridine, 1,2,3,4-tetrahydroimidazo[1,2-a:5,4-c']dipyridine, dihydro-1H-pyrano[3',4':4,5]imidazo[1,2-a]pyridine and tetrahydro-6H-cyclohepta[4,5]imidazo[1,2-a]pyridine, and analogs thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

16 Claims, No Drawings

FUSED TRICYCLIC IMIDAZOLE DERIVATIVES AS MODULATORS OF TNF ACTIVITY

This application is the US national phase under 35 U.S.C. § 371 of international application PCT/EP2014/076886, filed Dec. 8, 2014, which claims priority to GB application 1321730.2, filed Dec. 9, 2013.

The present invention relates to a class of fused tricyclic imidazole derivatives, and to their use in therapy. More particularly, this invention is concerned with pharmacologically active substituted fused imidazo pyridine derivatives. In particular the present invention relates to dihydro-1H-pyrano[4',3':4,5]imidazo[1,2-a]pyridine, 1,2,3,4-tetrahydroimidazo[1,2-a:5,4-c']dipyridine, dihydro-1H-pyrano[3',4':4,5]imidazo[1,2-a]pyridine and tetrahydro-6H-cyclohepta[4,5]imidazo[1,2-a]pyridine.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and ontological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused imidazopyridine derivatives as provided by the present invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

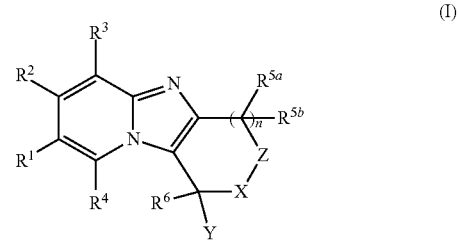

(I)

Wherein n represents an integer equal to 1 or 2.

Y represents $C_{3-7}$ cycloalkyl, aryl, $C_{3-7}$ heterocycloalkyl or heteroaryl, any of which groups may be optionally substituted by one or more substituents;

X and Z represent independently a heteroatom; or carbonyl, —S(O)—, —S(O)$_2$—, —S(O)(N—$R^d$), —NC(O)$R^d$, —N(CO)—O$R^d$, —NS(O)$_2R^d$, or —N($R^d$); or an optionally substituted straight or branched $C_{1-4}$ alkylene chain;

$R^1$ and $R^2$ independently represent hydrogen, halogen, cyano, nitro, hydroxy, trifluoromethyl, trifluoromethoxy, —$OR^a$, —$SR^a$, —$SOR^a$, —$SO_2R^a$, —$SF_5$, —$NR^bR^c$, —$NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$, —$SO_2NR^bR^c$, or —$S(O)(N$—$R^d)R^a$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{4-9}$)bicycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl-, heteroaryl-aryl- or ($C_{4-9}$)spiroheterocycloalkyl-heteroaryl-, any of which groups may be optionally substituted by one or more substituents;

$R^3$ and $R^4$ independently represents hydrogen, halogen, cyano, nitro, hydroxy, trifluoromethyl, trifluoromethoxy or —$OR^a$; or $C_{1-6}$ alkyl optionally substituted by one or more substituents;

$R^{5a}$ and $R^{5b}$ independently represent hydrogen, hydroxy, halogen, trifluoromethyl, cyano; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N$—$R^d)$, —$S(O)_2(N$—$R^d)$, —$OR^a$, —$C(O)$—$OR^d$, or —$O(CO)$—$R^d$—; $C_{1-6}$ alkyl, $C_{2-6}$ alkenyl, $C_{2-6}$ alkynyl, aryl, heteroaryl, any of which groups may be optionally substituted by one or more substituents; or $R^{5a}$ and $R^{5b}$ when taken together with the carbon to which they are attached represent a carbonyl, thiocarbonyl or —C=N—OH; and $R^6$ represents hydrogen, hydroxy, halogen, trifluoromethyl, or cyano; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N$—$R^d)$, —$S(O)_2(N$—$R^d)$, —$OR^a$, —$C(O)$—$OR^d$, or —$O(CO)$—$R^d$—; or $C_{1-6}$ alkyl, $C_{2-6}$ alkenyl, $C_{2-6}$ alkynyl, aryl, heteroaryl, any of which groups may be optionally substituted by one or more substituents; or $R^6$ and Y together with the carbon to which they are attached form a $C_{3-7}$ cycloalkyl or $C_{3-7}$ heterocycloalkyl, optionally substituted with one or more substituents; and $R^a$ represents $C_{1-6}$ alkyl, aryl, aryl($C_{1-6}$)alkyl, $C_{3-7}$ cycloalkyl, $C_{3-7}$ heterocycloalkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents; and $R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in therapy. The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H.

Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in Design of Prodrugs, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical $C_{4-9}$ bicycloalkyl groups include bicyclo[3.1.0]hexanyl, bicyclo[4.1.0]heptanyl, bicyclo[2.2.2]octanyl and bicyclo[3.3.1]-nonanyl.

Typical ($C_{4-9}$)bicycloalkenyl groups include bicyclo[3.1.0]hexenyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, dihydroisoindolyl, isoindolinyl, oxazolidinyl, thiazolidinyl, isothiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-c]pyrazinyl, homopiperazinyl, morpholinyl, benzoxazinyl, thiomorpholinyl, azepanyl, oxazepanyl, diazepanyl, thiadiazepanyl, azocanyl, (imino)(oxo)thiazinanyl, (oxo)thiazinanyl and (dioxo)thiazinanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]

nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, 2,3-dihydro-1H-isoindolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates.

Formula (I) and the formulae depicted hereinafter are intended to represent all individual stereoisomers and all possible mixtures thereof, unless stated or shown otherwise. In addition, compounds of formula (I) may exist as tautomers, for example keto $(CH_2C=O) \leftrightarrow$ enol $(CH=CHOH)$ tautomers or amide $(NHC=O) \leftrightarrow$ hydroxyimine $(N=COH)$ tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, n represents an integer equal to 1. In another embodiment n represents an integer equal to 2.

Generally, Y represents $C_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted $C_{3-7}$ cycloalkyl. In one aspect of that embodiment, Y represents unsubstituted $C_{3-7}$ cycloalkyl. In another aspect of that embodiment, Y represents monosubstituted $C_{3-7}$ cycloalkyl. In a further aspect of that embodiment, Y represents disubstituted $C_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted $C_{3-7}$ heterocycloalkyl. In one aspect of that embodiment, Y represents unsubstituted $C_{3-7}$ heterocycloalkyl. In another aspect of that embodiment, Y represents monosubstituted $C_{3-7}$ heterocycloalkyl. In a further aspect of that embodiment, Y represents disubstituted $C_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl, pyridinyl, pyrimidinyl or pyrazolyl any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, $(C_{1-6})$alkylsulfonyloxy, amino, $C_{1-6}$ alkyl-amino, di$(C_{1-6})$alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di$(C_{1-6})$alkylaminocarbonyl, aminosulfonyl, $C_{1-6}$ alkylaminosulfonyl and di$(C_{1-6})$alkylaminosulfonyl.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, methylsulfonyloxy, amino, methylamino, tert-butylamino, dimethylamino, phenylamino, acetylamino, methylsulfonylamino, formyl, acetyl, cyclopropylcarbonyl, azetidinylcarbonyl, pyrrolidinyl-carbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of particular substituents on the moiety Y include chloro, fluoro, cyano, methoxy, methylsulphonyl, trifluoromethoxy and difluoromethoxy.

Typical values of Y include benzocyclobutenyl, phenyl, (methysulphonyl)phenyl (including 4-methylsulphonylphenyl), benzonitrile (including 2-benzonitrile, 3-benzonitrile and 4-benzonitrile), fluorophenyl (including 2-fluorophenyl, 3-fluorophenyl and 4-fluorophenyl), chlorophenyl (including 2-chloro-phenyl, 3-chlorophenyl and 4-chlorophenyl), difluorophenyl (including 2,6-difluoro-phenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5- dimethylphenyl and 2,6-dimethylphenyl), (trifluoromethyl) phenyl [including 2-(trifluoromethyl)phenyl], (chloro)(trifluoromethyl)phenyl [including 5-chloro-2-(trifluoromethyl) phenyl], (methyl)-(trifluoromethyl)phenyl [including 2-methyl-5-(trifluoromethyl)phenyl], bis(trifluoro-methyl) phenyl [including 2,5-bis(trifluoromethyl)phenyl], methoxyphenyl (including 2-methoxyphenyl), (difluoromethoxy)phenyl [including 2-(difluoromethoxy)phenyl, 3-(difluoromethoxy)phenyl and 4-(difluoromethoxy)phenyl], (bis-(difluoromethoxy))phenyl [including 2,5-(di-fluoromethoxy))-phenyl and including 2,6-(bis-(difluoromethoxy))-phenyl], (difluoromethoxy)(fluoro)phenyl [including 2-(difluoromethoxy)-5-fluorophenyl, 2-(difluoromethoxy)-3-fluorophenyl, 2-(difluoromethoxy)-4-fluorophenyl, 2-(difluoromethoxy)-5-fluorophenyl, 2-(difluoromethoxy)-6-fluorophenyl and 5-(difluoromethoxy)-2-fluorophenyl], (difluoromethoxy)(difluoro)phenyl [(including 2-difluoromethoxy-3,5-difluoro-phenyl and difluoromethoxy-3,5-difluoro-phenyl)], (chloro)(difluoromethoxy)phenyl [including 2-chloro-5-(difluoromethoxy) phenyl, 5-chloro-2-(difluoromethoxy) phenyl, 5-chloro-3-(difluoromethoxy) phenyl, and 6-chloro-2-(difluoromethoxy) phenyl], (cyano) (difluoromethoxy) [including 6-cyano-2-(difluoromethoxy)-phenyl] (trifluoromethoxy) phenyl [including 2-(trifluoromethoxy)-phenyl], methylsulfonyloxyphenyl, (chloro)(trifluoromethoxy)phenyl, [including 3-chloro-6-trifluoromethoxy-phenyl)], (amino)(chloro) phenyl [including 5-amino-2-chloro-phenyl], methylthienyl [including 3-methylthien-2-yl), methylthiazolyl (including 2-methyl-1,3-thiazol-4-yl and 4-methyl-1,3-thiazol-4-yl)], (chloro)thiazolyl [including 4-chloro-1,3-thiazolyl], (chloro)(methyl)thiazolyl [including 5-chloro-2-methyl-1,3-thiazol-4-yl], dimethylthiazolyl [including 2,4-dimethyl-1,3-thiazol-5-yl], pyridinyl [including pyridin-3-yl and pyridin-4-yl], (methyl)(trifluoromethypthiazolyl [including 2-methyl-4-trifluoromethyl-1,3-thiazolyl], (dimethoxy)pyrimidinyl [including 4,6-dimethoxy-pyridin-5-yl] and (methoxy)pyrazinyl [including 5-methoxypyrazinyl].

Selected values of Y include phenyl, (methysulphonyl) phenyl, benzonitrile chlorophenyl, (chloro)(fluoro)phenyl, dichlorophenyl, dimethylphenyl, (trifluoromethyl)phenyl, (difluoromethoxy)phenyl, (bis-(difluoromethoxy))phenyl (difluoromethoxy)(fluoro)phenyl, (difluoromethoxy)(cyano) phenyl, (difluoromethoxy)(difluoro)phenyl, (chloro)(difluoromethoxy)phenyl, (chloro)(trifluoromethoxy)phenyl, (chloro)(methyl)thiazolyl, (chloro)thiazolyl, (methyl)(trifluoromethyl)thiazolyl, (dimethoxy)pyrimidinyl and (methoxy)pyrazinyl.

Particular values of Y include (difluoromethoxy)phenyl, (difluoromethoxy)(fluoro)phenyl, (chloro)(difluoromethoxy)phenyl and (difluoromethoxy)(cyano)phenyl.

Specific values of Y include 2-difluoromethoxy-phenyl, 2-difluoromethoxy-5-chloro-phenyl, 2-difluoromethoxy-6-chloro-phenyl, 2-difluoromethoxy-6-fluoro-phenyl, and 2-difluoromethoxy-6-cyano-phenyl.

In a particular embodiment, Y represents 2-(difluoromethoxy)phenyl.

In one embodiment, X represents a covalent bond; or an heteroatom; or —S(O), —S(O)$_2$, —S(O)(N—R$^d$), —NC(O)R$^d$, —N(CO)—OR$^d$, —NS(O)$_2$R$^d$, —N(R$^d$); or an optionally substituted straight or branched C$_{1-4}$ alkylene chain; and
Z represents an optionally substituted straight or branched C$_{1-4}$ alkylene chain.

In another embodiment, X represents an optionally substituted straight or branched C$_{1-4}$ alkylene chain; and
Z represents a covalent bond; or an heteroatom; or —S(O), —S(O)$_2$, —S(O)(N—R$^d$), —NC(O)R$^d$, —N(CO)—OR$^d$, —NS(O)$_2$R$^d$, —N(R$^d$); or an optionally substituted straight or branched C$_{1-4}$ alkylene chain.

Generally, X represents a heteroatom; or —S(O), —S(O)$_2$, —S(O)(N—R$^d$), —NC(O)R$^d$, —N(CO)—OR$^d$, —NS(O)$_2$R$^d$, —N(R$^d$); or an optionally substituted straight or branched C$_{1-4}$ alkylene chain;

Typically X represents an heteroatom; or —S(O), —N—R$^d$; or an optionally substituted straight or branched C$_{1-4}$ alkylene chain;

In a first embodiment, X represents a covalent bond.
In a second embodiment, X represents an heteroatom. In one aspect of that embodiment X is an oxygen. In a second aspect of that embodiment X is sulphur.
In a third embodiment, X represents —S(O).
In a fourth embodiment, X represents —S(O)$_2$.
In a fifth embodiment, X represents —S(O)(N—R$^d$).
In a sixth embodiment, X represents —NC(O)R$^d$.
In a seventh embodiment, X represents —N(CO)—OR$^d$.
In an eighth embodiment, X represents —NS(O)$_2$R$^d$.
In a ninth embodiment, X represents —N(R$^d$). In a particular aspect of this embodiment, X represents —NH.
In a tenth embodiment, X represents an optionally substituted straight or branched C$_{1-4}$ alkylene chain. Typical values of X according to this embodiment include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. In one aspect of this embodiment X represents an unsubstituted straight or branched C$_{1-4}$ alkylene chain. In a second aspect of this embodiment, X represents a monosubstituted straight or branched C$_{1-4}$ alkylene chain. In a third aspect of this embodiment, X represents a disubstituted straight or branched C$_{1-4}$ alkylene chain.

In an eleventh embodiment, X represents a carbonyl.
Particular values of X include methylene, oxygen and —N—H.

Typically, Z represents a covalent bond; or an heteroatom; or —NC(O)R$^d$, —N(CO)—OR$^d$, —NS(O)$_2$R$^d$, —N(R$^d$); or an optionally substituted straight or branched C$_{1-4}$ alkylene chain.

In a first embodiment, Z represents a covalent bond. In a second embodiment, Z represents an heteroatom. In one aspect of that embodiment Z is an oxygen. In a second aspect Z is sulphur. In a third embodiment, Z represents —S(O). In a fourth embodiment, Z represents —S(O)$_2$. In a fifth embodiment, Z represents —S(O)(N—R$^d$). In a sixth embodiment, Z represents —NC(O)R$^d$. In a seventh embodiment, Z represents —N(CO)—OR$^d$. In an eighth embodiment, Z represents —NS(O)$_2$R$^d$. In a ninth embodiment, Z represents —N(R$^d$). In a particular aspect of that embodiment, Z represents —NH.

In tenth embodiment, Z represents an optionally substituted straight or branched C$_{1-4}$ alkylene chain. Typical values of Z according to this embodiment include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. In one aspect of this embodiment Z represents an unsubstituted straight or branched C$_{1-4}$ alkylene chain. In a second aspect of this embodiment, Z represents a monosubstituted straight or branched C$_{1-4}$ alkylene chain. In a third aspect of this embodiment, Z represents a disubstituted straight or branched C$_{1-4}$ alkylene chain.

In an eleventh embodiment, Z represents a carbonyl.

Examples of typical substituents on the alkylene chain which may be present in a compound in accordance with the invention include halogen, hydroxy, oxo, $C_{1-6}$ alkoxy, aryl, —C(O)$R^d$, —CO$_2R^d$, —CONR$^b$R$^c$—S(O)(N—R$^d$)R$^a$, and —SO$_2$NR$^b$R$^c$.

Particular values of Z include methylene, oxygen and —N—H.

In a particular embodiment, X represents an optionally substituted straight or branched $C_{1-4}$ alkylene chain; and Z represents a covalent bond; or an heteroatom; or —NC(O)$R^d$, —N(CO)—OR$^d$, —NS(O)$_2R^d$, or —N(R$^d$); or an optionally substituted straight or branched $C_{1-4}$ alkylene chain.

In another particular embodiment, Z represents a covalent bond; or an optionally substituted straight or branched $C_{1-4}$ alkylene chain; and X represents an heteroatom, —S(O), or —N—R$^d$.

Suitably, $R^1$ and $R^2$ independently represent hydrogen, halogen, cyano, trifluoromethyl; —S(O)$_2$(N—R$^d$), or —CO$_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$heterocycloalkyl-, $(C_{3-7})$cycloalkyl-heteroaryl-, $(C_{3-7})$cycloalkyl $(C_{1-6})$alkyl-heteroaryl-, $(C_{4-7})$cycloalkenyl-hetero aryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl-, heteroaryl-aryl-, or $(C_{4-9})$spiroheterocycloalkyl-heteroaryl-, any of which groups may be optionally substituted by one or more substituents.

Typically, $R^2$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^3$ represents hydrogen, halogen, cyano, nitro, hydroxy, trifluoromethyl, trifluoromethoxy, —OR$^a$, —SR$^a$, —SOW, or —SO$_2R^a$; or $C_{1-6}$ alkyl optionally substituted by one or more substituents.

Typically, $R^3$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^4$ represents hydrogen, halogen, cyano, nitro, hydroxy, trifluoromethyl, trifluoromethoxy; —OR$^a$, —SR$^a$, —SOR$^a$, or —SO$_2R^a$; or $C_{1-6}$ alkyl optionally substituted by one or more substituents Typically, $R^4$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^{5a}$ represents hydrogen, hydroxy, halogen, cyano, trifluoromethyl, —NR$^b$R$^c$, —NR$^c$C(O)R$^d$, —(CO)NR$^c$R$^d$, —NHS(O)$_2R^e$, —S—R$^a$, —(SO)—R$^a$, —S(O)$_2R^a$, —S(O)(N—R$^d$), —S(O)$_2$(N—R$^d$), —OR$^a$, —C(O)2R$^d$, or —O(CO)—R$^d$—; or $C_{1-6}$ alkyl, $C_{2-6}$ alkenyl, $C_{2-6}$ alkynyl, aryl, or heteroaryl, any of which groups may be optionally substituted by one or more substituents.

Generally, $R^{5b}$ represents hydrogen, hydroxy, halogen, cyano, trifluoromethyl; —NR$^b$R$^c$, —NR$^c$C(O)R$^d$, —(CO)NR$^c$R$^d$, —NHS(O)$_2R^e$, —S—R$^a$, —(SO)—R$^a$, —S(O)$_2R^a$, —S(O)(N—R$^d$), —S(O)$_2$(N—R$^d$), —OR$^a$, —C(O)$_2R^d$, or —O(CO)—R$^d$—; or $C_{1-6}$ alkyl, $C_{2-6}$ alkenyl, $C_{2-6}$ alkynyl, aryl, or heteroaryl, any of which groups may be optionally substituted by one or more substituents.

Suitably, $R^{5a}$ represents hydrogen, hydroxy, halogen, cyano, trifluoromethyl, —NR$^b$R$^c$, —NR$^c$C(O)R$^d$, —(CO)NR$^c$R$^d$, —NHS(O)$_2R^e$, —S—R$^a$, —(SO)—R$^a$, —S(O)$_2R^a$, —S(O)(N—R$^d$), —S(O)$_2$(N—R$^d$), —OR$^a$, —C(O)$_2R^d$, or —O(CO)—R$^d$—; or $C_{1-6}$ alkyl, $C_{2-6}$ alkenyl, $C_{2-6}$ alkynyl, aryl, heteroaryl, any of which groups may be optionally substituted by one or more substituents; and $R^{5b}$ represents hydrogen, hydroxy, halogen, cyano, or trifluoromethyl; or $C_{1-6}$ alkyl, which group may be optionally substituted by one or more substituents.

Alternatively, $R^{5a}$ and $R^{5b}$ when taken together with the carbon to which they are attached represent a carbonyl, thiocarbonyl, or —C=N—OH.

Generally, $R^6$ represents hydrogen, hydroxy, halogen, cyano, trifluoromethyl, —NR$^b$R$^c$, —NR$^c$C(O)R$^d$, —(CO)NR$^c$R$^d$, —NHS(O)$_2R^e$, —S—R$^a$, —(SO)—R$^a$, —S(O)$_2R^a$, —S(O)(N—R$^d$), —S(O)$_2$(N—R$^d$), —OR$^a$, —C(O)$_2R^d$, or —O(CO)—R$^d$—; or $C_{1-6}$ alkyl, $C_{2-6}$ alkenyl, $C_{2-6}$ alkynyl, aryl, or heteroaryl, any of which groups may be optionally substituted by one or more substituents.

Examples of optional substituents which may be present on $R^1$, $R^2$, $R^3$, $R^4$ $R^{5a}$, $R^{5b}$ and $R^6$ include one, two or three substituents independently selected from halogen, halo-$(C_{1-6})$alkyl, cyano, cyano($C_{1-6}$)alkyl, nitro, nitro($C_{1-6}$)alkyl, $C_{1-6}$ alkyl, $(C_{3-7})$cycloalkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyl-oxy, $C_{1-3}$ alkylenedioxy, $C_{1-6}$ alkoxy$(C_{1-6})$alkyl, $C_{1-6}$ alkylthio, $C_{1-6}$ alkylsulphinyl, $C_{1-6}$ alkylsulphonyl, aryl-sulphonyl, $(C_{1-6})$alkylsulphonyl$(C_{1-6})$alkyl, oxo, amino, amino$(C_{1-6})$alkyl, $C_{1-6}$ alkyl-amino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, [$(C_{1-6})$alkoxy](hydroxy)$(C_{1-6})$alkylamino, [$(C_{1-6})$alkylthio](hydroxy)-$(C_{1-6})$alkylamino, N—[$(C_{1-6})$alkyl]-N-[hydroxy $(C_{1-6})$alkyl]amino, di$(C_{1-6})$alkylamino-$(C_{1-6})$alkylamino, N-[di$(C_{1-6})$alkylamino$(C_{1-6})$alkyl]-N-[hydroxy$(C_{1-6})$alkyl] amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkyl$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkyl-amino, $C_{2-6}$ alkylcarbonylamino, N—[$(C_{1-6})$alkyl]-N—[$(C_{2-6})$alkylcarbonyl]amino, $(C_{2-6})$alkyl-carbonylamino$(C_{1-6})$alkyl, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, $C_{2-6}$ alkoxycarbonylamino, $C_{2-6}$ alkoxycarbonyl$(C_{1-6})$alkylamino, $C_{1-6}$ alkylaminocarbonylamino, $C_{1-6}$ alkylsulphonyl-amino, N—[$(C_{1-6})$alkyl]-N—[$(C_{1-6})$alkylsulphonyl] amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy-$(C_{3-7})$cycloalkyl$(C_{1-6})$alkylamino, formyl, $C_{2-6}$ alkylcarbonyl, $(C_{3-7})$cycloalkylcarbonyl, phenylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω, —$(C_{1-6})$alkyl-Ω, aminocarbonyl, $C_{1-6}$ alkylaminocarbonyl, hydroxy$(C_{1-6})$alkylamino-carbonyl, di$(C_{1-6})$alkylaminocarbonyl, aminocarbonyl$(C_{1-6})$alkyl, aminosulphonyl, di$(C_{1-6})$ alkylaminosulphonyl, $(C_{1-6})$alkylsulphoximinyl and [$(C_{1-6})$ alkyl][N—$(C_{1-6})$alkyl]-sulphoximinyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.,* 2012, 3, 574-578. Typical examples of suitable carboxylic acid isostere or prodrug moieties represented by Ω include the functional groups of formula (i) to (xliii):
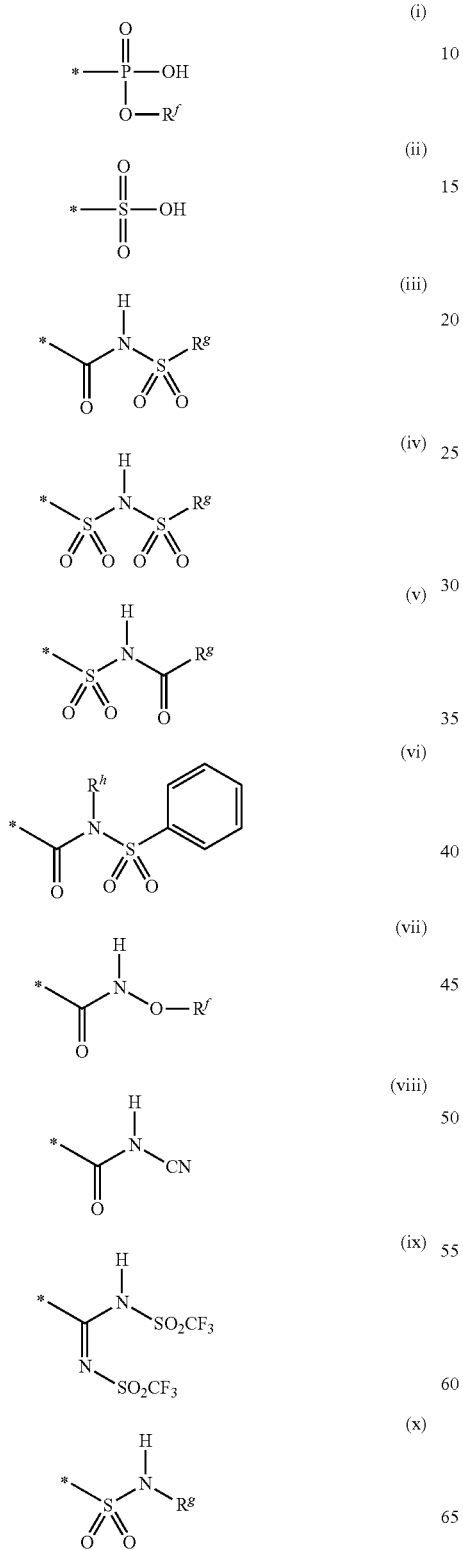
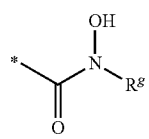
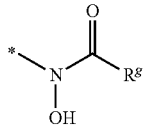
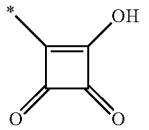
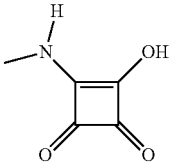
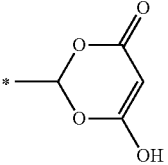
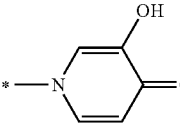
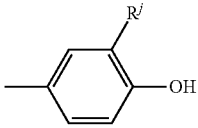
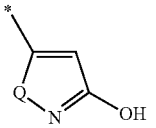
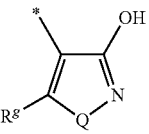
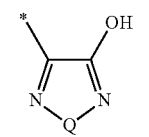

-continued
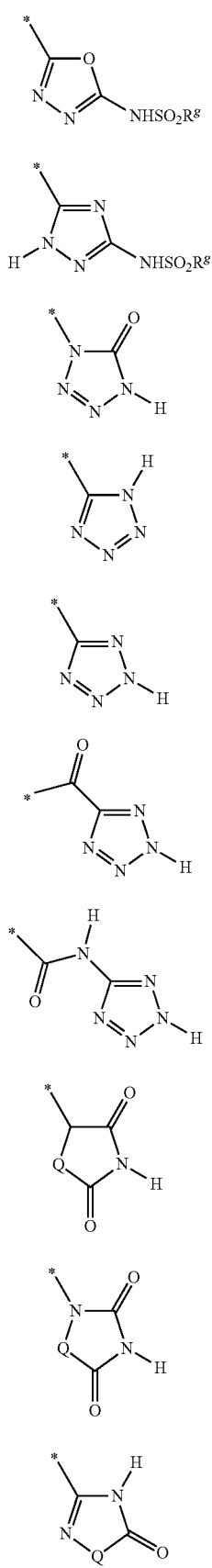
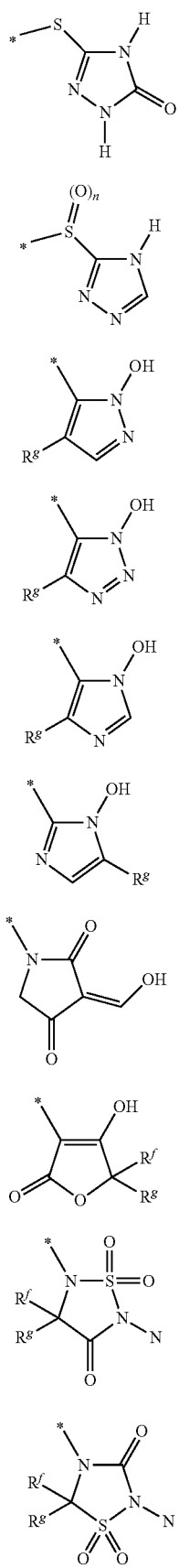

(xli)
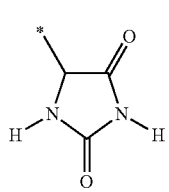

(xlii)
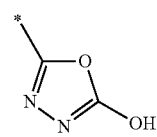

(xliii)
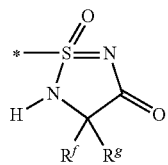

wherein
the asterisk (*) represents the site of attachment to the remainder of the molecule;
n is zero, 1 or 2;
Q represents oxygen or sulphur;
$R^f$ represents hydrogen, $C_{1-6}$ alkyl or —$CH_2CH(OH)CH_2OH$;
$R^g$ represents $C_{1-6}$ alkyl, trifluoromethyl, —$CH_2CH_2F$, —$CH_2CHF_2$, —$CH_2CF_3$ or —$CF_2CF_3$;
$R^h$ represents hydrogen, cyano or —$CO_2R^d$, in which $R^d$ is as defined above; and
$R^j$ represents hydrogen or halogen.

In one embodiment, n is zero. In another embodiment, n is 1. In a further embodiment, n is 2.

In one embodiment, Q represents oxygen. In another embodiment, Q represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$. In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents $(C_{1-6})$alkylcarbonylaminosulphonyl, i.e. a moiety of formula (v) as depicted above wherein $R^g$ represents $C_{1-6}$ alkyl.

Examples of particular substituents on $R^1$, $R^2$, $R^3$, $R^4$ $R^{5a}$, $R^{5b}$ and $R^6$ include fluoro, chloro, bromo, fluoromethyl, fluoroisopropyl, cyano, cyanoethyl, nitro, nitromethyl, methyl, ethyl, isopropyl, isobutyl, tert-butyl, cyclobutyl, cyclopropyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethyl-amino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylamino carbonyl, hydroxyethylamino carbonyl, dimethylaminocarbonyl, aminocarbonylmethyl, aminosulphonyl, methylaminosulphonyl, dimethylaminosulphonyl, phenylsulphonyl, methylsulphoximinyl and (methyl)(N-methyl)sulphoximinyl. Additional examples of particular substituents on $R^1$, $R^2$, $R^3$, $R^4$ $R^{5a}$, $R^{5b}$ and $R^6$ include cyanoisopropyl.

Selected examples of particular substituents on $R^1$, $R^2$, $R^3$, $R^4$, $R^{5a}$, $R^{5b}$, and $R^6$ include fluoro, hydroxy, phenylsulphonyl, methylsulphonyl, methyl, trifluoromethyl, cyclopropyl, cyclobutyl, isopropyl, methoxy, ethoxycarbonyl, oxo, carboxy, acetyl, methylsulphoximinyl, hydroxyisopropyl, fluroroisopropyl and cyanoisopropyl.

Typical examples of particular substituents on $R^1$, $R^2$, $R^3$, $R^4$, $R^{5a}$, $R^{5b}$, and $R^6$ include fluoro, hydroxy, phenylsulphonyl, methylsulphonyl, methyl, trifluoromethyl, cyclopropyl, cyclobutyl, isopropyl, methoxy, ethoxycarbonyl, oxo, carboxy, acetyl and methylsulphoximinyl.

Typically, $R^1$ represents hydrogen, halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl-, $(C_{4-9})$spiroheterocycloalkyl-heteroaryl- or heteroaryl-aryl, any of which groups may be optionally substituted by one or more substituents.

Suitably, $R^1$ represents halogen, cyano or $—CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl, $(C_{4-9})$spiroheterocycloalkyl-heteroaryl-, or heteroaryl-aryl, any of which groups may be optionally substituted by one or more substituents.

Generally, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl-, $(C_{4-9})$spiroheterocycloalkyl-heteroaryl-, or heteroaryl-aryl, any of which groups may be optionally substituted by one or more substituents.

More generally, $R^1$ represents halogen, $(C_{3-7})$heterocycloalkenyl, aryl, heteroaryl, $(C_{3-7})$cycloalkyl-heteroaryl-, $(C_{3-7})$heterocycloalkyl-heteroaryl-, or heteroraryl-aryl, either of which groups may be optionally substituted by one or more substituents.

Apositely, $R^1$ represents halogen, aryl, heteroaryl, $(C_{3-7})$cycloalkyl-heteroaryl-, $(C_{3-7})$heterocycloalkyl-heteroaryl-, or heteroraryl-aryl, either of which groups may be optionally substituted by one or more substituents.

In a first embodiment, $R^1$ represents hydrogen.

In a second embodiment, $R^1$ represents halogen. In one aspect of that embodiment, $R^1$ represents bromo. In a second aspect, $R^1$ is chloro.

In a third embodiment, $R^1$ represents cyano.

In a fourth embodiment, $R^1$ represents $—CO_2R^d$.

In a fifth embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl. In one aspect of this embodiment, $R^1$ represents optionally substituted 2,3-dihydro-1H-isoindole. In another aspect of this embodiment, $R^1$ represents optionally substituted azetidinyl. In another aspect of this embodiment, $R^1$ represents optionally substituted pyrrolidinyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, isoindolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-. In an eighth aspect of that embodiment, $R^1$ represents optionally substituted cyclopropylpyridinyl. In ninth aspect of that embodiment, $R^1$ represents optionally substituted cyclopropylpyrazolyl.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranylpyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In a twenty-fourth aspect of this embodiment, $R^1$ represents tetrahydro-thiopyranylpyrimidinyl. In a twenty-fifth aspect of this embodiment, $R^1$ represents tetrahydro-thiophenyl-pyrazolyl. In a twenty-sixth aspect of this embodiment, $R^1$ represents (imino)(oxo)thiazinanyl-pyrimidinyl. In a twenty-seventh aspect of this embodiment, $R^1$ represents (oxo)thiazinanyl-pyrimidinyl. In a twenty-eighth aspect of this embodiment, $R^1$ represents (dioxo)thiazinanyl-pyrimidinyl.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

In a twenty-second embodiment, $R^1$ represents optionally substituted $(C_{4-9})$-bicycloalkenyl-heteroaryl-.

In a twenty-third embodiment, $R^1$ represents optionally substituted heteroaryl-aryl. In one aspect of this embodiment, $R^1$ represents triazolyl-phenyl.

Appositely, $R^1$ represents hydrogen, chloro, bromo, cyano or —$CO_2R^d$; or ethyl, butynyl, phenyl, triazolyl-phenyl, azetidinyl, pyrrolidinyl, piperidinyl, piperazinyl, morpholinyl, 1,2,3,6-tetrahydropyridinyl, 3,6-dihydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclopropylpyridinyl, cyclopropylpyrazolyl, cyclohexenylpyrimidinyl, bicyclo[3.1.0]hexanylpyridinyl, bicyclo[3.1.0]hexanyl-pyrimidinyl, bicyclo[3.1.0]hexenyl-pyrimidinyl bicyclo[4.1.0]heptanylpyrimidinyl, bicyclo[2.2.2]octanylpyrimidinyl, pyrrolidinylpyridinyl, tetrahydropyranylpyridinyl, tetrahydrothiopyranylpyrimidinyl, piperidinylpyridinyl, piperazinylpyridinyl, morpholinylpyridinyl, thiomorpholinylpyridinyl, diazepanylpyridinyl, oxetanylpyridinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, piperazinyl)hexahydro-[1,2,5]thiadiazolo[2,3-c]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 1,1-(dioxidotetrahydrothiophenyl)pyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo[3.3.1]-nonanylpyrimidinyl, 3,7-dioxa-9-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, 2,4,8-triazaspiro[4.5]decanyl-pyrimidinyl, 3,6-epiminofuro[3.2-b]furanyl-pyrimidinyl, (imino)(oxo)thiazinanyl-pyrimidinyl, (oxo)thiazinanyl-pyrimidinyl, (dioxo)thiazinanyl-pyrimidinyl, or cyclobutylpyrimidinyl, any of which groups may be optionally substituted by one or more substituents.

Appropriately, $R^1$ represents chloro, bromo, phenyl, triazolyl-phenyl, azetidinyl, pyrrolidinyl, piperidinyl, piperazinyl, indolyl, pyrazolyl, pyridinyl, cyclopropylpyrimidinyl, cyclopropylpyridinyl, cyclopropylpyrazolyl, tetrahydropyranylpyridinyl, piperazinyl-pyridinyl, piperidinylpyrimidinyl, morpholinyl-pyrimidinyl, 1,1-(dioxidotetrahydrothiophenyl)pyrazolyl, (imino)(oxo)thiazinanyl-pyrimidinyl, (oxo)thiazinanyl-pyrimidinyl, (dioxo)thiazinanyl-pyrimidinyl, or cyclobutylpyrimidinyl.

Illustratively, $R^1$ represents phenyl, triazolyl-phenyl, azetidinyl, pyrrolidinyl, piperidinyl, piperazinyl, indolyl, pyrazolyl, pyridinyl, cyclopropylpyrimidinyl, cyclopropylpyridinyl, cyclopropylpyrazolyl, tetrahydropyranylpyridinyl, piperazinyl-pyridinyl, piperidinylpyrimidinyl, morpholinyl-pyrimidinyl, 1,1-(dioxidotetrahydrothiophenyl)pyrazolyl, (imino)(oxo)thiazinanyl-pyrimidinyl, (oxo)thiazinanyl-pyrimidinyl, (dioxo)thiazinanyl-pyrimidinyl, or cyclobutylpyrimidinyl.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, aryl-sulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkyl-sulphonyl]amino, N—[$(C_{1-6})$alkyl]-N-[carboxy$(C_{1-6})$alkyl]amino, carboxy$(C_{3-7})$cycloalkyl-amino, carboxy$(C_{3-7})$cycloalkyl$(C_{1-6})$alkylamino, formyl, $C_{2-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, aminocarbonyl, di$(C_{1-6})$alkylaminocarbonyl, aminosulphonyl, $(C_{1-6})$alkylsulphoximinyl and [$(C_{1-6})$alkyl][N—$(C_{1-6})$alkyl]sulphoximinyl.

Selected examples of optional substituents on $R^1$ include one, two or three substituents independently selected from halogen, hydroxy, trifluoromethyl, $C_{1-6}$ alkyl, halo ($C_{1-6}$) alkyl, $C_{1-6}$ alkoxy, $C_{2-6}$ alkylcarbonyl, $C_{2-6}$ alkylcarbonylamino($C_{1-6}$)alkyl, oxycarbonyl, $C_{2-6}$ alkyloxycarbonyl, (hydroxy)$C_{1-6}$ alkyl, ($C_{3-7}$)cycloalkyl, $C_{1-6}$ alkylsulphonyl, arylsulphonyl, ($C_{1-6}$)alkylsulphonyl($C_{1-6}$)alkyl, di($C_{1-6}$) alkylaminocarbonyl, oxo, carboxy, ($C_{1-6}$)alkylsulphoximinyl and (cyano)$C_{1-6}$ alkyl.

Suitable examples of optional substituents on $R^1$ include one, two or three substituents independently selected from halogen, hydroxy, trifluoromethyl, $C_{1-6}$ alkyl, halo ($C_{1-6}$) alkyl, $C_{1-6}$ alkoxy, $C_{2-6}$ alkylcarbonyl, $C_{2-6}$ alkylcarbonylamino($C_{1-6}$)alkyl, oxycarbonyl, $C_{2-6}$ alkyloxycarbonyl, (hydroxy)$C_{1-6}$ alkyl, ($C_{3-7}$)cycloalkyl, $C_{1-6}$ alkylsulphonyl, arylsulphonyl, ($C_{1-6}$)alkylsulphonyl($C_{1-6}$)alkyl, di($C_{1-6}$) alkylaminocarbonyl, oxo, carboxy and ($C_{1-6}$)alkylsulphoximinyl.

Typical examples of particular substituents on $R^1$ include one, two or three substituents independently selected from fluoro, chloro, chloromethyl, fluoromethyl, fluoroisopropyl, cyano, cyanoethyl, nitromethyl, methyl, ethyl, isopropyl, isopropylmethyl, cyclobutyl, cyclopropyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, phenylsulphonyl, methylsulphonyl, methylsulphonylmethyl, methylsulphonylethyl, oxo, amino, aminomethyl, amino isopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

Selected examples of substituents on $R^1$ include one, two or three substituents independently selected from hydroxy, methyl, chloromethyl, hydroxymethyl, hydroxyisopropyl, methoxy, cyclopropyl, cyclobutyl, phenylsulphonyl, methylsulphonyl, methylsulphonylmethyl, methylsulphonylethyl, acetylaminomethyl, carboxy, methoxycarbonyl, tert-butoxycarbonyl, ethoxycarbonyl, methylsulphoximinyl, cyanoisopropyl and fluoroisopropyl.

Particular examples of substituents on $R^1$ include one, two or three substituents hydroxyl, methyl, chloromethyl, hydroxymethyl, hydroxyisopropyl, methoxy, cyclopropyl, cyclobutyl, phenylsulphonyl, methylsulphonyl, methylsulphonylmethyl, methylsulphonylethyl, acetylaminomethyl, carboxy, methoxycarbonyl, tert-butoxycarbonyl, ethoxycarbonyl and methylsulphoximinyl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In a second particular embodiment, $R^1$ is substituted by $C_{1-6}$ alkylsulphonyl. In one aspect of this embodiment, $R^1$ is substituted by methylsulphonyl.

In a third particular embodiment $R^1$ is substituted by a halogen. In one aspect of this embodiment, $R^1$ is substituted by a fluoro.

In a fourth particular embodiment, $R^1$ is substituted by ($C_{1-6}$)alkylsulphoximinyl. In one aspect of this embodiment, $R^1$ is substituted by a methylsulphoximinyl.

In a fifth particular embodiment, $R^1$ is substituted by halo($C_{1-6}$) alkyl. In one aspect of this embodiment, $R^1$ is substituted by fluoroisopropyl.

In a sixth particular embodiment, $R^1$ is substituted by cyano($C_{1-6}$)alkyl. In one aspect of this embodiment, $R^1$ is substituted by a cyanoisopropyl.

Typical values of $R^1$ include hydrogen, bromo, chloro, cyano, —$CO_2R^d$, methoxycarbonyl-ethyl, ethoxycarbonylethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (di-(trifluoromethyl))(hydroxy)phenyl, methoxyazetidinyl, methoxypyrrolidinyl, (methoxycarbonyl)(methyl)pyrrolidinyl, (methoxymethyl)pyrrolidinyl, chloropyridinyl, (chloromethyl)pyridinyl, oxopiperidinyl, (carboxy)piperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, methylsulphonylpyrazolyl, methylsulphonylethylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoro-pyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo)pyridinyl, aminopyridinyl, methylaminopyridinyl, dimethyl-aminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, cyclopropylpyrimidinyl, fluoromethylcyclopropylpyrimidinyl, acetylaminomethylcyclopropylpyrimidinyl, hydroxymethylpyrimidinyl, hydroxycyclobutylpyrimidinyl, (methyl)cyclobutyldiol-pyrimidinyl, carboxy-cyclopentylpyrimidinyl, carboxycyclohexylpyrimidinyl, (carboxy)(methyl)cyclohexyl-pyrimidinyl, (carboxy)(hydroxy)cyclohexylpyrimidinyl, carboxymethylcyclohexyl-pyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]

hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methyl-sulphonylethylpiperazinylpyridinyl, oxopiperazinylpyridinyl, acetylpiperazinylpyridinyl, (tert-butoxycarbonylpiperazinyl)pyridinyl, (tert-butoxycarbonylpiperazinyl)(methyppyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinyl-pyridinyl, (tert-butoxycarbonyl)-3,6-dihydropyridine, oxothiomorpholinylpyridinyl, dioxothiomorpholinylpyridinyl, oxodiazepanyl-pyridinyl, tetrahydropyranylpyrimidinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxy-pyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinyl-pyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methyl-sulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxy-methylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinyl-pyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxothiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinyl-pyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]-octanylpyrimidinyl, 3-(dimethylaminocarbonyl)-8-azabicyclo-[3.2.1]octanylpyrimidinyl,oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanyl-pyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro[3.2-b]furanyl-pyrimidinyl, 5-(methyl-1H-1,2,4-triazol-3yl)phenyl, dihydroisoindolyl, (methylsulphonyl)dihydroisoindolyl (tetrahydrothiopenyl)pyrazolyl, methylsulphoximinylphenyl, (imino)(oxo)thiazinanyl-pyrimidinyl, (oxo)thiazinanyl-pyrimidinyl and (dioxo)thiazinanyl-pyrimidinyl. Additional values of $R^1$ include cyanoisopropylphenyl.

Definitive values of $R^1$ hydrogen, bromo, chloro, methylsulphonylphenyl, methoxyazetidinyl, methoxypyrrolidinyl, (methoxymethyl)pyrrolidinyl, (chloromethyl)pyridinyl, (carboxy)piperidinyl, methylsulphonylpiperazinyl, pyrazolyl, methylsulphonylpyrazolyl, methylsulphonylethylpyrazolyl, hydroxymethylpyridinyl, methoxypyridinyl, methylsulphonylpyridinyl, methylsulphonylmethylpyridinyl, piperazinylpyridinyl, (tert-butoxycarbonylpiperazinyl) pyridinyl, (tetrahydropyranylpyrimidinyl, (carboxy)(methyl)piperidinylpyrimidinyl, methoxycarbonylpiperidinylpyrimidinyl, (ethoxycarbonyl)-(methyl)piperidinylpyrimidinyl, morpholinylpyrimidinyl, 5-(methyl-1H-1,2,4-triazol-3yl)phenyl, dihydroisoindolyl, (methylsulphonyl)dihydroisoindolyl, (tetrahydrothiophenyl) pyrazolyl, methylsulphoximinylphenyl, (imino)(oxo)thiazinanyl-pyrimidinyl, (oxo)thiazinanyl-pyrimidinyl, (dioxo) thiazinanyl-pyrimidinyl, sulphoximinomorpholinylpyrimidinyl, fluoroisopropylpyrimidinyl, hydroxyisopropylpyrimidinyl, and cyanoisopropylphenyl. Selected values of $R^1$ include hydrogen, bromo, chloro, methyl-sulphonylphenyl, methoxyazetidinyl, methoxypyrrolidinyl, (methoxymethyl)pyrrolidinyl, (chloromethyl)pyridinyl, (carboxy)piperidinyl, methylsulphonylpiperazinyl, pyrazolyl, methylsulphonylpyrazolyl, methylsulphonylethylpyrazolyl, hydroxymethylpyridinyl, methoxypyridinyl, methylsulphonylpyridinyl, methylsulphonylmethylpyridinyl, piperazinylpyridinyl, (tert-butoxycarbonylpiperazinyl)pyridinyl, (tetrahydropyranylpyrimidinyl, (carboxy)(methyl)piperidinylpyrimidinyl, methoxycarbonylpiperidinylpyrimidinyl, (ethoxycarbonyl)-(methyl)piperidinylpyrimidinyl, morpholinylpyrimidinyl, 5-(methyl-1H-1,2,4-triazol-3yl)phenyl, dihydroisoindolyl, (methylsulphonyl)dihydroisoindolyl and (tetrahydrothiophenyl)pyrazolyl.

Typically, $R^2$ represents hydrogen, halogen, cyano, nitro, hydroxy, trifluoromethyl, trifluoromethoxy; or —$OR^a$; or an optionally substituted $C_{1-6}$ alkyl.

Particularly, $R^2$ represents hydrogen or halogen.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, trifluoromethoxy, —$OR^a$, methyl and ethoxycarbonylethyl.

Particular values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro.

In a third embodiment, $R^3$ represents $C_{1-6}$ alkyl. In one aspect of that embodiment, $R^3$ represents unsubstituted $C_{1-6}$ alkyl. In a second aspect of that embodiment, $R^3$ represents substituted $C_{1-6}$ alkyl. In a particular aspect of this embodiment, $R^3$ represents methyl. In another particular aspect of that embodiment, $R^3$ represents ethyl.

In a particular embodiment, $R^3$ represents hydrogen.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents $C_{1-6}$ alkyl. In one aspect of that embodiment, $R^4$ represents unsubstituted $C_{1-6}$ alkyl. In a second aspect of that embodiment, $R^4$ represents substituted $C_{1-6}$ alkyl. In a particular aspect of this embodiment, $R^4$ represents methyl. In another particular aspect of that embodiment, $R^4$ represents ethyl.

In a particular embodiment, $R^4$ represents hydrogen.

Generally, $R^{5a}$ represents hydrogen, hydroxy, halogen, cyano, trifluoromethyl —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N$—$R^d)$, —$S(O)_2(N$—$R^d)$, —$OR^a$, —$C(O)2R^d$, or —$O(CO)$—$R^d$—; or $C_{1-6}$ alkyl, $C_{2-6}$ alkenyl, $C_{2-6}$ alkynyl, aryl, heteroaryl, any of which groups may be optionally substituted by one or more substituents.

Typically, $R^{5a}$ represents hydrogen, hydroxy, halogen, trifluoromethyl, —$NR^bR^c$, $S(O)_2R^a$, —$OR^a$, or —O—(CO)_$R^d$; or $C_{1-6}$ alkyl which group may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylamino carbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, amino isopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —$NR^bR^c$. In one aspect of that embodiment, $R^{5a}$ represents —$NH_2$. In a sixth embodiment, $R^{5a}$ represents —$NR^cC(O)R^d$. In a seventh embodiment, $R^{5a}$ represents —$C(O)$—$NR^cR^d$. In an eighth embodiment, $R^{5a}$ represents —$NHS(O)_2R^e$. In a ninth embodiment, $R^{5a}$ represents —S—$R^a$. In a tenth embodiment, $R^{5a}$ represents —$S(O)$—$R^a$. In an eleventh embodiment, $R^{5a}$ represents —$S(O)_2R^a$. In a particular aspect of this embodiment, $R^{5a}$ represents —$S(O)_2$—CH3. In a twelfth embodiment, $R^{5a}$ represents —$S(O)(N$—$R^d)R^a$. In a thirteenth embodiment, $R^{5a}$ represents —$S(O)_2(N$—$R^d)$. In a fourteenth embodiment, $R^{5a}$ represents —OR$^a$. In one aspect of this embodiment, R$^a$ is a C$_{1-6}$ alkyl. In second aspect of this embodiment R$^a$ is an aryl. In a third aspect of this embodiment, R$^a$ is an heteroaryl. In a fifteenth embodiment, R$^{5a}$ represents —O—(CO)—R$^d$. In a particular aspect of this embodiment, R$^{5a}$ represents —O—(CO)—CH$_3$. In a sixteenth embodiment, —C(O)—OR$^d$. In a seventeenth embodiment, R$^{5a}$ represents optionally substituted C$_{1-6}$ alkyl. In one aspect of that embodiment, R$^{5a}$ represents substituted C$_{1-6}$ alkyl. In a second aspect of this embodiment, R$^{5a}$ represents unsubstituted C$_{1-6}$ alkyl. In a particular aspect of this embodiment, R$^{5a}$ represents methyl. In an eighteenth embodiment, R$^{5a}$ represents an optionally substituted C$_{2-6}$ alkynyl. In a nineteenth embodiment, R$^{5a}$ represents an optionally substituted heteroaryl.

In a twentieth embodiment R$^{5a}$ represents an optionally substituted aryl. In a twenty-first embodiment, R$^{5a}$ represents an optionally substituted C$_{2-6}$ alkenyl.

In a twenty-second embodiment, R$^{5a}$ represents cyano.

Generally, R$^{5b}$ represents hydrogen, hydroxy, halogen, cyano, trifluoromethyl, —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)2R$^d$, or —O(CO)—R$^d$—; or C$_{1-6}$ alkyl, C$_{2-6}$ alkenyl, C$_{2-6}$ alkynyl, aryl, or heteroaryl, any of which groups may be optionally substituted by one or more substituents.

Typically, R$^{5b}$ represents hydrogen, hydroxy, halogen, trifluoromethyl, —NR$^b$R$^c$, S(O)$_2$R$^a$, —OR$^a$, or —O—(CO)_R$^d$; or C$_{1-6}$ alkyl which group may be optionally substituted.

Suitably, R$^{5b}$ represents hydrogen, hydroxy, halogen, cyano, or trifluoromethyl; or C$_{1-6}$ alkyl, which group may be optionally substituted by one or more substituents.

Suitable examples of optional substituents on R$^{5b}$ include one, two or three substituents independently selected from halogen, hydroxy, trifluoromethyl, C$_{1-6}$ alkyl, C$_{1-6}$ alkoxy, C$_{2-6}$ alkylcarbonyl, C$_{2-6}$ alkyloxycarbonyl, (hydroxy)C$_{1-6}$ alkyl, (C$_{3-7}$)cycloalkyl, C$_{1-6}$ alkylsulphonyl, (C$_{1-6}$)alkylsulphonyl(C$_{1-6}$)alkyl, di(C$_{1-6}$)alkylaminocarbonyl, oxo, and carboxy.

Typical examples of particular substituents on R$^{5b}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, R$^{5b}$ represents hydrogen. In a second embodiment, R$^{5b}$ represents hydroxy. In a third embodiment, R$^{5b}$ represents halogen. In one aspect of this embodiment, R$^{5b}$ represents fluoro. In a fourth embodiment, R$^{5b}$ represents trifluoromethyl. In a fifth embodiment, R$^{5b}$ represents —NR$^b$R$^c$. In one aspect of that embodiment, R$^{5b}$ represents —NH$_2$. In a sixth embodiment, R$^{5b}$ represents —NR$^c$C(O)R$^d$. In a seventh embodiment, R$^{5b}$ represents —C(O)—NR$^c$R$^d$. In an eighth embodiment, R$^{5b}$ represents —NHS(O)$_2$R$^e$. In a ninth embodiment, R$^{5a}$ represents —S—R$^a$. In a tenth embodiment, R$^{5b}$ represents —S(O)—R$^a$. In an eleventh embodiment, R$^{5b}$ represents —S(O)$_2$R$^a$. In a particular aspect of this embodiment, R$^{5b}$ represents —S(O)$_2$—CH3. In a twelfth embodiment, R$^{5b}$ represents —S(O)(N—R$^d$)R$^a$. In a thirteenth embodiment, R$^{5b}$ represents —S(O)$_2$(N—R$^d$). In a fourteenth embodiment, R$^{5b}$ represents —OR$^a$. In one aspect of this embodiment, R$^a$ is a C$_{1-6}$ alkyl. In second aspect of this embodiment R$^a$ is an aryl. In a third aspect of this embodiment, R$^a$ is an heteroaryl. In a fifteenth embodiment, R$^{5b}$ represents —O—(CO)—R$^d$. In a particular aspect of this embodiment, R$^{5a}$ represents —O—(CO)—CH$_3$. In a sixteenth embodiment, —C(O)—OR$^d$. In a seventeenth embodiment, R$^{5b}$ represents optionally substituted C$_{1-6}$ alkyl. In one aspect of that embodiment, R$^{5b}$ represents substituted C$_{1-6}$ alkyl. In a second aspect of this embodiment, R$^{5b}$ represents unsubstituted C$_{1-6}$ alkyl. In a particular aspect of this embodiment, R$^{5b}$ represents methyl. In an eighteenth embodiment, R$^{5b}$ represents an optionally substituted C$_{2-6}$ alkynyl. In a nineteenth embodiment, R$^{5b}$ represents an optionally substituted heteroaryl. In a twentieth embodiment R$^{5b}$ represents an optionally substituted aryl. In a twenty-first embodiment, R$^{5b}$ represents an optionally substituted C$_{2-6}$ alkenyl. In a twenty-second embodiment, R$^{5b}$ represents cyano.

Particularly, R$^{5b}$ represents hydrogen or methyl.

In an alternative embodiment, R$^{5a}$ and R$^{5b}$ when taken together with the carbon to which they are attached represent a carbonyl, thiocarbonyl or —C=N—OH.

In one aspect of that alternative embodiment, R$^{5a}$ and R$^{5b}$ when taken together with the carbon to which they are attached represent a carbonyl.

In a second aspect of that alternative embodiment, R$^{5a}$ and R$^{5b}$ when taken together with the carbon to which they are attached represent a thiocarbonyl.

In another aspect of that alternative embodiment, R$^{5a}$ and R$^{5b}$ when taken together with the carbon to which they are attached represent —C=N—OH.

Selected values of R$^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

Selected values of R$^{5b}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

In a particular embodiment, R$^{5a}$ is as defined above and R$^{5b}$ represents hydrogen. In a particular aspect of this embodiment, R$^{5a}$ is hydroxy.

In another particular embodiment R$^{5a}$ is as defined above and R$^{5b}$ represents C$_{1-4}$ alkyl, preferably methyl. In a particular aspect of this embodiment, R$^{5a}$ is hydroxy.

Generally, R$^6$ represents hydrogen, hydroxy, halogen, trifluoromethyl, —NR$^b$R$^c$, —NR$^c$C(O)R$^d$, —NHS(O)$_2$R$^e$, —S(O)$_2$R$^a$, —S(O)(N—R$^d$)R$^a$ or —O—(CO)R$^d$; or C$_{1-6}$ alkoxy, C$_{1-6}$ alkyl, C$_{2-6}$ alkynyl, heteroaryl, any of which groups may be optionally substituted by one or more substituents.

Typically, R$^6$ represents hydrogen, hydroxy, halogen, or trifluoromethyl.

In a particular embodiment, R$^6$ represents hydrogen.

In an alternative embodiment, R$^6$ and Y together with the carbon to which they are attached form a C$_{3-7}$ cycloalkyl.

In another alternative embodiment, $R^6$ and Y together with the carbon to which they are attached form a $C_{3-7}$ heterocycloalkyl. In one particular aspect according to this embodiment, $R^6$ and Y together with the carbon to which they are attached form a dihydrobenzofuran. In a second particular aspect according to this embodiment, $R^6$ and Y together with the carbon to which they are attached form a 3H-benzofuranone. In a third particular aspect according to this embodiment, $R^6$ and Y together with the carbon to which they are attached form a dihydroisoindole. In a fourth particular aspect according to this embodiment, $R^6$ and Y together with the carbon to which they are attached form a dihydroisoindolone.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylamino carbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents $C_{3-7}$ cycloalkyl. In another further embodiment, $R^a$ represents $C_{3-7}$ heterocycloalkyl, Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl or (dioxo)thiazinan-4-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl.

In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl.

In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl.

In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Particular examples of selected values for $R^d$ include hydrogen and methyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds of formula (I) according to the invention is represented by the compounds of formula (IIA) and N-oxides thereof, and pharmaceutically acceptable salts and solvates thereof, and glucuronide derivatives thereof, and co-crystals thereof:

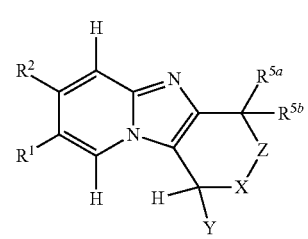

(IIA)

Wherein $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl($C_{3-7}$)heterocycloalkyl-, $(C_{3-7})$cycloalkyl-heteroaryl-, $(C_{3-7})$cycloalkyl-($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl-, heteroaryl-aryl, or $(C_{4-9})$spiroheterocycloalkyl-heteroaryl-, any of which groups may be optionally substituted by one or more substituents.

$R^2$ represents hydrogen, halogen, trifluoromethyl, or cyano; or an optionally substituted $C_{1-6}$ alkyl.

X and Z represent independently an oxygen atom, a sulphur atom; —S(O), or —N(R$^d$); or an optionally substituted straight or branched $C_{1-4}$ alkylene chain.

R$^{5a}$ represents hydrogen, hydroxy, halogen, cyano, or trifluoromethyl; or —NR$^b$R$^c$, —NR$^c$C(O)R$^d$, —(CO) NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)2R$^d$, —O(CO)—R$^d$—; $C_{1-6}$ alkyl, $C_{2-6}$ alkenyl, $C_{2-6}$ alkynyl, aryl, heteroaryl, any of which groups may be optionally substituted by one or more substituents; and R$^{5b}$ represents hydrogen, hydroxy, halogen, cyano, or trifluoromethyl; or $C_{1-6}$ alkyl, any of which groups may be optionally substituted by one or more substituents; or R$^{5a}$ and R$^{5b}$ when taken together with the carbon to which they are attached represent a carbonyl, thiocarbonyl, or —C=N—OH; and Y, R$^a$, R$^b$, R$^c$ and R$^d$ are as defined above for compounds of formula (I).

In a particular embodiment, X represents an optionally substituted straight or branched $C_{1-4}$ alkylene chain; and Z represent independently an oxygen atom, a sulphur atom; —S(O), or —N(R$^d$).

In another particular embodiment, Z represents an optionally substituted straight or branched $C_{1-4}$ alkylene chain; and X represents an oxygen atom, a sulphur atom; —S(O), or —N(R$^d$).

Examples of optional substituents which may be present on R$^1$, R$^2$, R$^{5a}$ and R$^{5b}$ include one, two or three substituents independently selected from halogen, halo-($C_{1-6}$)alkyl, cyano, cyano($C_{1-6}$)alkyl, nitro, nitro($C_{1-6}$)alkyl, $C_{1-6}$ alkyl, ($C_{3-7}$)cycloalkyl, difluoromethyl, trifluoromethyl, difluoroethyl, trifluoroethyl, $C_{2-6}$ alkenyl, hydroxy, hydroxy($C_{1-6}$) alkyl, $C_{1-6}$ alkoxy, difluoromethoxy, trifluoromethoxy, trifluoroethoxy, carboxy($C_{3-7}$)cycloalkyl-oxy, $C_{1-3}$ alkylenedioxy, $C_{1-6}$ alkoxy($C_{1-6}$)alkyl, $C_{1-6}$ alkylthio, $C_{1-6}$ alkylsulphinyl, $C_{1-6}$ alkylsulphonyl, aryl-sulphonyl, ($C_{1-6}$) alkylsulphonyl($C_{1-6}$)alkyl, oxo, amino, amino($C_{1-6}$)alkyl, $C_{1-6}$ alkyl-amino, di($C_{1-6}$)alkylamino, hydroxy($C_{1-6}$)alkylamino, $C_{1-6}$ alkoxyamino, ($C_{1-6}$)alkoxy-($C_{1-6}$)alkylamino, [($C_{1-6}$)alkoxy](hydroxy)($C_{1-6}$)alkylamino, [($C_{1-6}$)alkylthio] (hydroxy)-($C_{1-6}$)alkylamino, N—[($C_{1-6}$)alkyl]-N-[hydroxy ($C_{1-6}$)alkyl]amino, di($C_{1-6}$)alkylamino-($C_{1-6}$)alkylamino, N-[di($C_{1-6}$)alkylamino($C_{1-6}$)alkyl]-N-[hydroxy($C_{1-6}$)alkyl] amino, hydroxy($C_{1-6}$)alkyl($C_{3-7}$)cycloalkylamino, (hydroxy)[($C_{3-7}$)cycloalkyl($C_{1-6}$)alkyl]amino, ($C_{3-7}$)heterocycloalkyl($C_{1-6}$)alkylamino, oxo($C_{3-7}$)heterocycloalkyl($C_{1-6}$) alkylamino, ($C_{1-6}$)alkylheteroarylamino, heteroaryl($C_{1-6}$) alkylamino, ($C_{1-6}$)alkylheteroaryl($C_{1-6}$)alkyl-amino, $C_{2-6}$ alkylcarbonylamino, N—[($C_{1-6}$)alkyl]-N—[($C_{2-6}$)alkylcarbonyl]amino, ($C_{2-6}$)alkyl-carbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonyl-amino, N—[($C_{1-6}$)alkyl]-N—[)$C_{1-6}$)alkylsulphonyl] amino, bis[($C_{1-6}$)alkylsulphonyl]amino, N—[($C_{1-6}$)alkyl]-N-[carboxy($C_{1-6}$)alkyl]amino, carboxy($C_{3-7}$) cycloalkylamino, carboxy-($C_{3-7}$)cycloalkyl($C_{1-6}$) alkylamino, formyl, $C_{2-6}$ alkylcarbonyl, ($C_{3-7}$) cycloalkylcarbonyl, phenylcarbonyl, ($C_{2-6}$) alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω as defined herein, —($C_{1-6}$)alkyl-Ω, amino carbonyl, $C_{1-6}$ alkylamino carbonyl, hydroxy($C_{1-6}$)alkylamino-carbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Examples of particular substituents on R$^1$, R$^2$, R$^{5a}$ and R$^{5b}$ include fluoro, chloro, chloromethyl, bromo, fluoromethyl, fluoroisopropyl, cyano, cyanoethyl, nitro, nitromethyl, methyl, ethyl, isopropyl, cyclopropyl, cyclobutyl, isobutyl, tert-butyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, phenylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy) propylamino, morpholinylethyl-amino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylamino carbonyl, hydroxyethylamino carbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl. Additional example of particular substituents, R$^2$, R$^{5a}$ and R$^{5b}$ include cyanoisopropyl. Selected examples of particular substituents on R$^1$, R$^2$, R$^{5a}$ and R$^{5b}$ include fluoro, hydroxy, phenylsulphonyl, methylsulphonyl, methyl, trifluoromethyl, cyclopropyl, cyclobutyl, isopropyl, methoxy, ethoxycarbonyl, oxo, carboxy, acetyl, methylsulphoximinyl, hydroxyisopropyl, fluroroisopropyl and cyanoisopropyl.

Generally, R$^1$ represents halogen, ($C_{3-7}$)heterocycloalkenyl, aryl, heteroaryl, ($C_{3-7}$)cycloalkyl-heteroaryl-, ($C_{3-7}$) heterocycloalkyl-heteroaryl-, or heteroraryl-aryl, either of which groups may be optionally substituted by one or more substituents.

Typically, R$^1$ represents aryl, heteroaryl, heteroaryl-aryl, ($C_{3-7}$)cycloalkyl-heteroaryl or ($C_{3-7}$)heterocycloalkyl-heteroaryl-, either of which groups may be optionally substituted by one or more substituents.

In a first embodiment, $R^1$ represents halogen. In one aspect of that embodiment, $R^1$ represents bromo. In a second aspect, $R^1$ is chloro.

In a second embodiment, $R^1$ represents cyano.

In a third embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl.

In a fourth embodiment, $R^1$ represents optionally substituted $C_{2-6}$ alkynyl. In one aspect of that embodiment, $R^1$ represents optionally substituted butynyl.

In a fifth embodiment, $R^1$ represents optionally substituted aryl. In one aspect of that embodiment, $R^1$ represents optionally substituted phenyl.

In an sixth embodiment, $R^1$ represents optionally substituted $C_{3-7}$ heterocycloalkyl. In one aspect of this embodiment, $R^1$ represents optionally substituted 2,3-dihydro-1H-isoindole. In another aspect of this embodiment, $R^1$ represents optionally substituted azetidinyl. In another aspect of this embodiment, $R^1$ represents optionally substituted pyrrolidinyl.

In a seventh embodiment, $R^1$ represents optionally substituted $C_{3-7}$ heterocycloalkenyl.

In an eighth embodiment, $R^1$ represents optionally substituted heteroaryl. In selected aspects of that embodiment, $R^1$ represents benzofuryl, thienyl, indolyl, isoindolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In a ninth embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a tenth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In an eleventh embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-. In an eighth aspect of that embodiment, $R^1$ represents optionally substituted cyclopropylpyridinyl. In ninth aspect of that embodiment, $R^1$ represents optionally substituted cyclopropylpyrazolyl.

In a twelfth embodiment, $R^1$ represents optionally substituted $(C_{4-7})$-cycloalkenyl-heteroaryl-.

In a thirteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranylpyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In a twenty-fourth aspect of this embodiment, $R^1$ represents tetrahydro-thiopyranylpyrimidinyl. In a twenty-fifth aspect of this embodiment, $R^1$ represents tetrahydro-thiophenyl-pyrazolyl. In a twenty-sixth aspect, $R^1$ represents (imino)(oxo)thiazinanyl-pyrimidinyl. In twenty-seventh aspect of that embodiment, $R^1$ represents (oxo)thiazinanyl-pyrimidinyl. In twenty-eighth aspect of that embodiment, $R^1$ represents and (dioxo)thiazinanyl-pyrimidinyl.

In a fourteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a fifteenth embodiment, $R^1$ represents optionally substituted $(C_{3-7})$-heterocycloalkenyl-heteroaryl-.

In a sixteenth embodiment, $R^1$ represents optionally substituted $(C_{4-9})$-heterobicycloalkyl-heteroaryl-.

In a seventeenth embodiment, $R^1$ represents optionally substituted $(C_{4-9})$-spiroheterocycloalkyl-heteroaryl-.

In an eighteenth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a nineteenth embodiment, $R^1$ represents optionally substituted $(C_{4-9})$-bicycloalkyl-heteroaryl-.

In a twentieth embodiment, $R^1$ represents optionally substituted heteroaryl-aryl. In one aspect of this embodiment, $R^1$ represents triazolyl-phenyl.

Appositely, $R^1$ represents chloro, bromo, cyano; or ethyl, butynyl, phenyl, triazolyl-phenyl, azetidinyl, pyrrolidinyl, piperidinyl, piperazinyl, morpholinyl, 1,2,3,6-tetrahydropyridinyl, 3,6-dihydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexyl-pyrimidinyl, cyclohexylpyrazinyl, cyclohexylmethylpyrimidinyl, cyclohexenylpyridinyl, cyclopropylpyridinyl, cyclopropylpyrazolyl, cyclohexenylpyrimidinyl, bicyclo[3.1.0]hexanylpyridinyl, bicyclo[3.1.0]hexanyl-pyrimidinyl, bicyclo[3.1.0]hexenyl-pyrimidinyl bicyclo[4.1.0]heptanylpyrimidinyl, bicyclo[2.2.2]octanylpyrimidinyl, pyrrolidinylpyridinyl, tetrahydropyranylpyridinyl, tetrahydrothiopyranylpyrimidinyl, piperidinylpyridinyl, piperazinyl-pyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, hexahydro-[1,2,5]thiadiazolo[2,3-c]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 1,1-(dioxidotetrahydrothiophenyl)pyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo[3.3.1]-nonanylpyrimidinyl, 3,7-dioxa-9-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, 2,4,8-triazaspiro[4.5]decanyl-pyrimidinyl, 3,6-epiminofuro[3.2-b]furanyl-pyrimidinyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents.

Appropriately, $R^1$ represents chloro, bromo, phenyl, triazolyl-phenyl, azetidinyl, pyrrolidinyl, piperidinyl, piperazinyl, indolyl, pyrazolyl, pyridinyl, cyclopropylpyrimidinyl, cyclobutypyrimidinyl, cyclopropylpyridinyl, cyclopropylpyrazolyl, tetrahydropyranylpyridinyl, piperazinyl-pyridinyl, piperidinylpyrimidinyl, morpholinyl-pyrimidinyl, 1,1-(dioxidotetrahydrothiophenyl)pyrazolyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents Illustratively, $R^1$ represents phenyl, triazolyl-phenyl, azetidinyl, pyrrolidinyl, piperidinyl, piperazinyl, indolyl, pyrazolyl, pyridinyl, cyclopropylpyrimidinyl, cyclopropylpyridinyl, cyclobutypyrimidinyl, cyclopropylpyrazolyl, tetrahydropyranylpyridinyl, piperazinyl-pyridinyl, piperidinylpyrimidinyl, morpholinyl-pyrimidinyl, 1,1-(dioxidotetrahydrothiophenyl)pyrazolyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro($C_{1-6}$)alkyl, $C_{1-6}$ alkyl, $C_{3-7}$ cycloalkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, aryl-sulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, di($C_{1-6}$)alkylaminocarbonyl, amino sulphonyl, ($C_{1-6}$)alkylsulphoximinyl and [($C_{1-6}$)alkyl][N—($C_{1-6}$)alkyl]sulphoximinyl.

Suitable examples of optional substituents on $R^1$ include one, two or three substituents independently selected from halogen, hydroxy, trifluoromethyl, $C_{1-6}$ alkyl, cyclopropyl, halo ($C_{1-6}$)alkyl, $C_{1-6}$ alkoxy, $C_{2-6}$ alkylcarbonyl, $C_{2-6}$ alkylcarbonylamino($C_{1-6}$)alkyl, oxycarbonyl, $C_{2-6}$ alkyloxycarbonyl, (hydroxy)$C_{1-6}$ alkyl, ($C_{3-7}$)cycloalkyl, $C_{1-6}$ alkylsulphonyl, arylsulphonyl, ($C_{1-6}$)alkylsulphonyl($C_{1-6}$)alkyl, di($C_{1-6}$)alkylaminocarbonyl, oxo, carboxy and cyano($C_{1-6}$)alkyl.

Suitable examples of optional substituents on $R^1$ include one, two or three substituents independently selected from halogen, hydroxy, trifluoromethyl, $C_{1-6}$ alkyl, cyclopropyl, halo ($C_{1-6}$)alkyl, $C_{1-6}$ alkoxy, $C_{2-6}$ alkylcarbonyl, $C_{2-6}$ alkylcarbonylamino($C_{1-6}$)alkyl, oxycarbonyl, $C_{2-6}$ alkyloxycarbonyl, (hydroxy)$C_{1-6}$ alkyl, ($C_{3-7}$)cycloalkyl, $C_{1-6}$ alkylsulphonyl, arylsulphonyl, ($C_{1-6}$)alkylsulphonyl($C_{1-6}$)alkyl, di($C_{1-6}$)alkylaminocarbonyl, oxo, and carboxy.

Typical examples of particular substituents on $R^1$ include one, two or three substituents independently selected from fluoro, chloro, chloromethyl, fluoromethyl, fluoroisopropyl, cyano, cyanoethyl, nitromethyl, methyl, ethyl, isopropyl, cyclopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, phenylsulphonyl, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

Selected examples of substituents on $R^1$ include one, two or three substituents selected from hydroxy, methyl, chloromethyl, hydroxymethyl, hydroxyisopropyl, methoxy, cyclopropyl, cyclobutyl, phenylsulphonyl, methylsulphonyl, methylsulphonylmethyl, methylsulphonylethyl, acetylaminomethyl, carboxy, methoxycarbonyl, tert-butoxycarbonyl, ethoxycarbonyl, methylsulphoximinyl, fluoroisopropyl and cyanoisopropyl.

Particular examples of substituents on $R^1$ include one, two or three substituents hydroxy, methyl, chloromethyl, hydroxymethyl, hydroxyisopropyl, methoxy, phenylsulphonyl, methylsulphonyl, methylsulphonylmethyl, methylsulphonylethyl, methylsulphoximinyl, acetylaminomethyl, carboxy, methoxycarbonyl, tert-butoxycarbonyl and ethoxycarbonyl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In second particular embodiment, $R^1$ is substituted by $C_{1-6}$ alkylsulphonyl. In one aspect of this embodiment, $R^1$ is substituted by methylsulphonyl.

In a third particular embodiment $R^1$ is substituted by a halogen. In one aspect of this embodiment, $R^1$ is substituted by a fluoro.

In a fourth particular embodiment, $R^1$ is substituted by ($C_{1-6}$)alkylsulphoximinyl. In one aspect of this particular embodiment, $R^1$ is substituted by methylsulphoximinyl.

In fifth particular embodiment, $R^1$ is substituted by halo ($C_{1-6}$) alkyl. In one aspect of this embodiment, $R^1$ is substituted by fluoroisopropyl.

In a sixth particular embodiment, $R^1$ is substituted by cyano($C_{1-6}$). In one aspect of this embodiment, $R^1$ is substituted by a cyanoisopropyl.

Selected values of $R^1$ include bromo, chloro, cyano, methoxycarbonyl-ethyl, ethoxycarbonylethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (di-(trifluoromethyl))(hydroxy)phenyl, methoxyazetidinyl, methoxypyrrolidinyl, (methoxycarbonyl)(methyl)pyrrolidinyl, (methoxymethyl)pyrrolidinyl, chloropyridinyl, (chloromethyl)pyridinyl, oxopiperidinyl, (carboxy)piperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, methylsulphonylpyrazolyl, methylsulphonylethylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoro-pyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)pyridinyl, (dimethyl)(oxo)pyridinyl, aminopyridinyl, methylaminopyridinyl, dimethyl-aminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, cyclopropylpyrimidinyl, fluoromethylcyclopropylpyrimidinyl, acetylaminomethylcyclopropylpyrimidinyl, hydroxymethylpyrimidinyl, hydroxycyclobutylpyrimidinyl, (methyl)cylobutyldiol-pyrimidinyl, carboxy-cyclopentylpyrimidinyl, carboxycyclohexylpyrimidinyl, (carboxy)(methyl)cyclohexyl-pyrimidinyl, (carboxy)(hydroxy)cyclohexylpyrimidinyl, carboxymethylcyclohexyl-pyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methyl-sulphonylethylpiperazinylpyridinyl, oxopiperazinylpyridinyl, acetylpiperazinylpyridinyl, (tert-butoxycarbonylpiperazinyl)pyridinyl, (tert-butoxycarbonylpiperazinyl)(methyl)pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinyl-pyridinyl, (tert-butoxycarbonyl)-3,6-dihydropyridine, oxothiomorpholinylpyridinyl, dioxothiomorpholinylpyridinyl, oxodiazepanyl-pyridinyl, tetrahydropyranylpyrimidinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxy-pyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinylpyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methyl-sulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxy-methylpiperidinylpyrimidinyl, methoxycarbonylpiperidinylpyrimidinyl, ethoxycarbonyl-piperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinyl-pyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxo-thiomorpholinylpyrimidinyl, dioxo-thiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinyl-pyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]-octanylpyrimidinyl, 3-(dimethylamino carbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanyl-pyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro[3.2-b]furanyl-pyrimidinyl, 5-(methyl-1H-1,2,4-triazol-3yl)phenyl, dihydroisoindolyl, (methylsulphonyl)dihydroisoindolyl, (tetrahydrothiopenyl)pyrazolyl, methylsulphoximinylphenyl, (imino)(oxo)thiazinanyl-pyrimidinyl, (oxo)thiazinanyl-pyrimidinyl and (dioxo)thiazinanyl-pyrimidinyl. Additional values of $R^1$ include cyanoisopropylphenyl.

Definitive values of $R^1$ include hydrogen, bromo, chloro, methyl-sulphonylphenyl, methoxyazetidinyl, methoxypyrrolidinyl, (methoxymethyl)pyrrolidinyl, (chloromethyl)pyridinyl, (carboxy)piperidinyl, methylsulphonylpiperazinyl, pyrazolyl, methylsulphonylpyrazolyl, methylsulphonylethylpyrazolyl, hydroxymethylpyridinyl, methoxypyridinyl, methylsulphonylpyridinyl, methylsulphonylmethylpyridinyl, piperazinylpyridinyl, (tert-butoxycarbonylpiperazinyl)pyridinyl, (tetrahydropyranylpyrimidinyl, (carboxy)(methyl)piperidinylpyrimidinyl, methoxycarbonylpiperidinylpyrimidinyl, (ethoxycarbonyl)-(methyl)piperidinylpyrimidinyl, morpholinylpyrimidinyl, 5-(methyl-1H-1,2,4-triazol-3yl)phenyl, dihydroisoindolyl, (methylsulphonyl)dihydroisoindolyl, (tetrahydrothiopenyl)pyrazolyl, methylsulphoximinylphenyl, (imino)(oxo)thiazinanyl-pyrimidinyl, (oxo)thiazinanyl-pyrimidinyl, (dioxo)thiazinanyl-pyrimidinyl, sulphoximinomorpholinylpyrimidinyl, fluoroisopropylpyrimidinyl, hydroxyisopropylpyrimidinyl, and cyanoisopropylphenyl.

Selected values of $R^1$ include hydrogen, bromo, chloro, methyl-sulphonylphenyl, methoxyazetidinyl, methoxypyrrolidinyl, (methoxymethyl)pyrrolidinyl, (chloromethyl)pyridinyl, (carboxy)piperidinyl, methylsulphonylpiperazinyl, pyrazolyl, methylsulphonylpyrazolyl, methylsulphonylethylpyrazolyl, hydroxymethylpyridinyl, methoxypyridinyl, methylsulphonylpyridinyl, methylsulphonylmethylpyridinyl, piperazinylpyridinyl, (tert-butoxycarbonylpiperazinyl)pyridinyl, (tetrahydropyranylpyrimidinyl, (carboxy)(methyl)piperidinylpyrimidinyl, methoxycarbonylpiperidinylpyrimidinyl, (ethoxycarbonyl)-(methyl)piperidinylpyrimidinyl, morpholinylpyrimidinyl, 5-(methyl-1H-1,2,4-triazol-3yl)phenyl, dihydroisoindolyl, (methylsulphonyl)dihydroisoindolyl, (tetrahydrothiopenyl)pyrazolyl, methylsulphoximinylphenyl, (imino)(oxo)thiazinanyl-pyrimidinyl, (oxo)thiazinanyl-pyrimidinyl, (dioxo)thiazinanyl-pyrimidinyl and sulphoximinomorpholinylpyrimidinyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl. In a fifth embodiment, $R^2$ represents cyano.

Typical values of $R^2$ include hydrogen, fluoro, chloro, trifluoromethyl, methyl and ethoxycarbonylethyl.

Particular values of $R^2$ include hydrogen and fluoro.

In a first embodiment, X represents an heteroatom. In one aspect of that embodiment X is an oxygen atom. In a second aspect of that embodiment, X is a sulphur atom.

In a second embodiment, X represents —S(O).

In a third embodiment X represents —N($R^d$). In one aspect of this embodiment X represents —NH.

In a fourth embodiment, X represents an optionally substituted straight or branched $C_{1-4}$ alkylene chain. Typical values of X according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment X represents an unsubstituted straight or branched $C_{1-4}$ alkylene chain. In a second aspect of this embodiment, X represents a monosubstituted straight or branched $C_{1-4}$ alkylene chain. In a third aspect of this embodiment, X represents a disubstituted straight or branched $C_{1-4}$ alkylene chain. In a particular aspect of this embodiment, X represents an unsubstituted methylene.

Examples of typical substituents on the alkylene chain which may be present in a compound in accordance with the invention include halogen, hydroxy, $C_{1-6}$ alkoxy, aryl, —C(O)$R^d$, —$CO_2R^d$, —CONR$^b$R$^c$—S(O)(N—$R^d$)$R^a$, or —$SO_2NR^bR^c$.

Particular values of X include oxygen, —NH and methylene.

In a particular embodiment, X is oxygen. In another particular embodiment X is —NH.

In a first embodiment, Z represents an heteroatom. In one aspect of that embodiment Z is an oxygen atom. In a second aspect of that embodiment, Z is a sulphur atom.

In a second embodiment, Z represents —S(O).

In a third embodiment Z represents —N($R^d$). In one aspect of this embodiment Z represents —NH.

In a fourth embodiment, Z represents an optionally substituted straight or branched $C_{1-4}$ alkylene chain. Typical values of Z according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment Z represents an unsubstituted straight or branched $C_{1-4}$ alkylene chain. In a second aspect of this embodiment, Z represents a monosubstituted straight or branched $C_{1-4}$ alkylene chain. In a third aspect of this embodiment, Z represents a disubstituted straight or branched $C_{1-4}$ alkylene chain. In a particular aspect of this embodiment, Z represents an unsubstituted methylene.

Examples of typical substituents on the alkylene chain which may be present in a compound in accordance with the invention include halogen, hydroxy, oxo, $C_{1-6}$ alkoxy, aryl, —C(O)$R^d$, —$CO_2R^d$, —CONR$^b$R$^c$—S(O)(N—$R^d$)$R^a$, or —$SO_2NR^bR^c$.

Particular values of Z include oxygen, —NH and methylene.

In a particular embodiment, Z is methylene.

In a particular embodiment, X is oxygen or NH and Z is methylene.

Typically, $R^{5a}$ represents hydrogen, hydroxy, halogen, trifluoromethyl, —NR$^b$R$^c$, S(O)$_2$R$^a$, —OR$^a$, or —O—(CO)_$R^d$; or $C_{1-6}$ alkyl which group may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, amino isopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —NR$^b$R$^c$. In one aspect of that embodiment, $R^{5a}$ represents —NH$_2$. In a sixth embodiment, $R^{5a}$ represents —NR$^c$C(O)R$^d$. In a seventh embodiment, $R^{5a}$ represents —C(O)—NR$^c$R$^d$. In an eighth embodiment, $R^{5a}$ represents —NHS(O)$_2$R$^e$. In a ninth embodiment, $R^{5a}$ represents —S—R$^a$. In a tenth embodiment, $R^{5a}$ represents —S(O)—R$^a$. In an eleventh embodiment, $R^{5a}$ represents —S(O)$_2$R$^a$. In a particular aspect of this embodiment, $R^{5a}$ represents —S(O)$_2$—CH3. In a twelfth embodiment, $R^{5a}$ represents —S(O)(N—R$^d$)R$^a$. In a thirteenth embodiment, $R^{5a}$ represents —S(O)$_2$(N—R$^d$). In a fourteenth embodiment, $R^{5a}$ represents —OR$^a$. In one aspect of this embodiment, $R^a$ is a $C_{1-6}$ alkyl. In second aspect of this embodiment $R^a$ is an aryl. In a third aspect of this embodiment, $R^a$ is an heteroaryl. In a fifteenth embodiment, $R^{5a}$ represents —O—(CO)—R$^d$. In a particular aspect of this embodiment, $R^{5a}$ represents —O—(CO)—CH$_3$. In a sixteenth embodiment, —C(O)—OR$^d$. In a seventeenth embodiment, $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, $R^{5a}$ represents an optionally substituted $C_{2-6}$ alkenyl.

In a twenty-second embodiment, $R^{5a}$ represents cyano.

Typically, $R^{5b}$ represents hydrogen or hydroxy; $C_{1-6}$ alkyl or $C_{1-6}$alkoxy, either of which groups may be optionally substituted.

In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5a}$ represents fluoro. In a fourth embodiment, $R^{5b}$ represents trifluoromethyl. In fifth embodiment, $R^{5b}$ represents substituted or unsubstituted $C_{1-6}$ alkyl. In one aspect of that embodiment $R^{5b}$ is methyl. In a sixth embodiment, $R^{5b}$ represents cyano.

Particular values of $R^{5b}$ include hydrogen and methyl.

In a particular alternative embodiment, $R^{5a}$ and $R^{5b}$ when taken together with the carbon to which they are attached represent a carbonyl.

In second particular alternative embodiment, $R^{5a}$ and $R^{5b}$ when taken together with the carbon to which they are attached represent a thiocarbonyl.

In third particular alternative embodiment, $R^{5a}$ and $R^{5b}$ when taken together with the carbon to which they are attached represent —C=N—OH.

Selected values of $R^{5a}$ include hydrogen, hydroxy, fluoro, trifluoromethyl, —N(CH$_3$)$_2$, —NH(CO)CH$_3$, —SO$_2$—CH$_3$, —CO$_2$—CH$_3$, methyl and methoxy.

Selected values of $R^{5b}$ include hydrogen, hydroxy, fluoro, trifluoromethyl and methyl.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

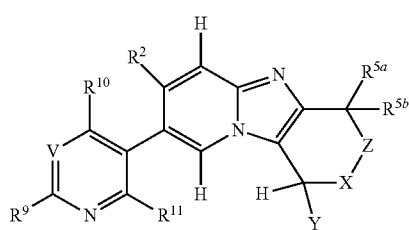

(IIB)

wherein

V represents C—$R^{12}$ or N;

$R^9$ represents hydrogen, halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, aryl-sulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N—[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, di($C_{1-6}$)alkylaminocarbonyl, aminosulphonyl, ($C_{1-6}$)alkylsulphoximinyl or [($C_{1-6}$)alkyl][N—($C_{1-6}$)alkyl] sulphoximinyl; or $R^9$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{4-9}$)bicyclo alkylene, ($C_{3-7}$)heterocycloalkyl, ($C_{3-7}$)heterocycloalkyl($C_{1-6}$)alkyl, ($C_{3-7}$)heterocycloalkenyl, ($C_{4-9}$)heterobicycloalkyl or ($C_{4-9}$)spiroheterocycloalkyl, or heteroaryl, any of which groups may be optionally substituted by one or more substituents;

$R^{10}$ and $R^{11}$ independently represents hydrogen, halogen, cyano, trifluoromethyl, hydroxy, —NR$^b$R$^c$, or —OR$^a$; or $C_{1-6}$ alkyl or $C_{1-6}$ alkylsulphonyl;

$R^{12}$ represents hydrogen, halogen or $C_{1-6}$ alkyl; and

X, Z, Y, R$^2$, R$^{5a}$ and R$^{5b}$ are as defined above for compounds of formula (IIA).

In one embodiment, V represents C—$R^{12}$. In another embodiment, V represents N.

Typically, $R^9$ represents hydrogen, halogen, halo($C_{1-6}$)alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, arylsulphonyl, ($C_{1-6}$)alkylsulphonyl($C_{1-6}$)alkyl, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl ($C_{1-6}$)alkoxycarbonyl, $C_{2-6}$ alkoxycarbonyl($C_{1-6}$)alkyl, $C_{2-6}$ alkoxycarbonylmethylidenyl, di($C_{1-6}$)alkylaminocarbonyl, or ($C_{1-6}$)alkylsulphoximinyl; or $R^9$ represents ($C_{3-7}$)cycloalkyl, ($C_{3-7}$)cycloalkyl-($C_{1-6}$)alkyl, ($C_{4-7}$)cycloalkenyl, ($C_{4-9}$) bicycloalkyl, ($C_{3-7}$)heterocycloalkyl, ($C_{4-9}$)heterobicycloalkyl ($C_{4-9}$)spiroheterocycloalkyl, ($C_{4-9}$)bicycloalkylene or heteroaryl, any of which groups may be optionally substituted by one or more substituents.

Typically, $R^9$ represents ($C_{1-6}$)alkyl, halo($C_{1-6}$)alkyl, (hydroxy) $C_{1-6}$ alkyl, $C_{1-6}$ alkoxy, arylsulphonyl, $C_{1-6}$ alkylsulphonyl, ($C_{1-6}$)alkylsulphonyl($C_{1-6}$)alkyl, $C_{2-6}$ alkylcarbonylamino($C_{1-6}$)alkyl, ($C_{1-6}$)alkylsulphoximinyl, carboxy, oxo, or $C_{2-6}$ alkyloxycarbonyl; or $R^9$ represents ($C_{3-7}$)cycloalkyl, ($C_{3-7}$)heterocycloalkyl, or heteroaryl, any of which groups may be optionally substituted by one or more substituents.

Where $R^9$ represents an optionally substituted ($C_{3-7}$)cycloalkyl group, typical values include cyclopropyl, cyclobutyl, cyclopentyl, cyclohexyl and cycloheptyl, any of which groups may be optionally substituted by one or more substituents.

Where $R^9$ represents an optionally substituted ($C_{3-7}$)cycloalkyl($C_{1-6}$)alkyl group, a typical value is cyclohexylmethyl, which group may be optionally substituted by one or more substituents.

Where $R^9$ represents an optionally substituted ($C_{4-7}$)cycloalkenyl group, typical values include cyclobutenyl, cyclopentenyl, cyclohexenyl and cycloheptenyl, any of which groups may be optionally substituted by one or more substituents.

Where $R^9$ represents an optionally substituted ($C_{4-9}$)bicycloalkyl group, typical values include bicyclo[3.1.0]hexanyl, bicyclo[4.1.0]heptanyl and bicyclo[2.2.2]octanyl, any of which groups may be optionally substituted by one or more substituents.

Where $R^9$ represents an optionally substituted ($C_{4-9}$)bicycloalkenyl group, a typical value is bicyclo[3.1.0]hexenyl.

Where $R^9$ represents an optionally substituted ($C_{3-7}$)heterocycloalkyl group, typical values include oxetanyl, azetidinyl, tetrahydrofuranyl, pyrrolidinyl, tetrahydropyranyl, piperidinyl, piperazinyl, hexahydro-[1,2,5]thiadiazolo[2,3-c]pyrazinyl, morpholinyl, thiomorpholinyl, azepanyl, oxazepanyl, diazepanyl, thiadiazepanyl, (imino)(oxo)thiazinanyl, (oxo)thiazinanyl or (dioxo)thiazinanyl, any of which groups may be optionally substituted by one or more substituents.

Where $R^9$ represents an optionally substituted ($C_{3-7}$)heterocycloalkenyl group, a typical value is optionally substituted 1,2,3,6-tetrahydropyridinyl or 3,6-dihydropyridine.

Where $R^9$ represents an optionally substituted ($C_{4-9}$)heterobicycloalkyl group, typical values include 3-azabicyclo[3.1.0]hexanyl, 2-oxa-5-azabicyclo[2.2.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,9-diazabicyclo-[4.2.1]nonanyl and 3,6-epimino[3,2b]-furanyl, any of which groups may be optionally substituted by one or more substituents.

Where $R^9$ represents an optionally substituted ($C_{4-9}$)spiroheterocycloalkyl group, typical values include 5-azaspiro[2.3]hexanyl, 5-azaspiro[2.4]heptanyl, 2-azaspiro[3.3]-heptanyl, 2-oxa-6-azaspiro[3.3]heptanyl, 2-oxa-6-azaspiro[3.4]octanyl, 2-oxa-6-azaspiro-[3.5]nonanyl, 2-oxa-7-azaspiro[3.5]nonanyl and 2,4,8-triazaspiro[4.5]-decanyl, any of which groups may be optionally substituted by one or more substituents.

When $R^9$ represents an optionally substituted heteroaryl, typical values include triazolyl and (methyl)triazolyl.

Illustratively, $R^9$ represents hydrogen, isopropyl, isopropylmethyl, hydroxy, hydroxymethyl, hydroxyisopropyl, chloromethyl, methoxy, carboxy-cyclobutyloxy, methylthio, methylsulphonyl, methylsulphonylmethyl, methylamino, N-[carboxyethyl]-N-methyl-amino, carboxycyclopentylamino, carboxycyclopropylmethylamino, methylsulfoximinyl, or ethoxycarbonyl-ethyl; or $R^9$ represents cyclopropyl, cyclobutyl, cyclopentyl, cyclohexyl, cyclohexyl-methyl, cyclohexenyl, bicyclo[3.1.0]hexanyl, bicyclo[3.1.0]hexenyl bicyclo[4.1.0]heptanyl, bicyclo[2.2.2]-octanyl, oxetanyl, azetidinyl, tetrahydrofuranyl, pyrrolidinyl, tetrahydropyranyl, tetrahydro-thiopyranylpyrimidinyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 3-azabicyclo-[4.1.0]heptanyl, 2-oxabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,6-diazabicyclo[3.2.2]nonanyl, 3-oxa-7-azabicyclo[3.3.1]nonanyl, 5-azaspiro[2.3]hexanyl, 5-azaspiro[2.4]heptanyl, 2-azaspiro-[3.3]heptanyl, 3,7-dioxa-9-azabicyclo[3.3.1]-nonanyl, epiminofuro[3.2-b]furanyl (imino)(oxo)thiazinanyl, (oxo)thiazinanyl, (dioxo)thiazinanyl or triazolyl, any of which groups may be optionally substituted by one or more substituents.

Apositely, $R^9$ represents chloromethyl, hydroxymethyl, methoxy, methylsulphonyl, methylsulphonylmethyl, methylsulphonylethyl, phenylsulphonyl; or cyclopropyl, piperazinyl, piperidinyl, morpholinyl, tetrahydropyranyl, or triazolyl, any of which groups may be optionally substituted by one or more substituents.

Examples of optional substituents which may be present on $R^9$ include one, two or three substituents independently selected from halogen, halo($C_{1-6}$)alkyl, cyano, cyano-($C_{1-6}$) alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$) alkylamino, $C_{2-6}$ alkylcarbonylamino, ($C_{2-6}$) alkylcarbonylamino-($C_{1-6}$)alkyl, $C_{2-6}$ alkoxycarbonylamino, $C_{1-6}$ alkylsulphonylamino, formyl, $C_{1-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, amino-carbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$) alkyl]-sulphoximinyl.

Selected examples of optional substituents on $R^9$ include one, two or three substituents independently selected from halogen, cyano, trifluoromethyl, hydroxy, $C_{1-6}$ alkyl, $C_{1-6}$ alkoxy, $C_{1-6}$ alkylsulphonyl, ($C_{1-6}$)alkylsulphoximinyl, $C_{1-6}$ alkylcarbonyl, $C_{1-6}$ alkoxycarbonyl, oxo and carboxy.

Suitable examples of particular substituents on $R^9$ include one, two or three substituents independently selected from fluoro, fluoromethyl, chloro, bromo, cyano, cyanomethyl, cyanoethyl, nitro, nitromethyl, methyl, ethyl, isopropyl, cyclopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetyl-aminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinyl-ethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethyl-aminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Selected examples of particular substituents on $R^9$ include one, two or three substituents independently selected from hydroxyl, methyl, trifluoromethyl, tert-butoxycarbonyl, ethoxycarbonyl, methoxycarbonyl, methylsulphonyl, methylsulphonylmethyl, methylsulphonylethyl, methylsulphoximinyl, oxo and carboxy.

Typically, $R^9$ represents hydrogen, fluoro, fluoroisopropyl, cyano, methyl, chloromethyl, isopropyl, trifluoromethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, amino, methylamino, dimethylamino, methoxyethylamino, N-(hydroxyethyl)-N-(methyl)amino, N-[carboxy-ethyl]-N-methylamino, carboxycyclopentylamino, carboxycyclopropylmethylamino, methylsulphonylamino, acetoxyisopropyl, carboxy, ethoxycarbonylethyl, cyclopropyl, fluoromethyl-cyclopropyl, acetylaminomethylcyclopropyl, hydroxycyclobutyl, carboxycyclopentyl, carboxycyclohexyl, (carboxy)(methyl)cyclohexyl, (carboxy)(hydroxy)cyclohexyl, carboxymethylcyclohexyl, ethoxycarbonylcyclohexyl, (methoxycarbonyl)(methyl)-cyclohexyl, (ethoxycarbonyl)(methyl)cyclohexyl, carboxycyclohexylmethyl, carboxycyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolyl-azetidinyl, hydroxytetrahydrofuranyl, pyrrolidinyl, hydroxypyrrolidinyl, carboxy-pyrrolidinyl, (carboxy)(methyl)pyrrolidinyl, carboxymethylpyrrolidinyl, ethoxycarbonyl-pyrrolidinyl, fluorotetrahydropyranyl, tetrahydropyranyl, hydroxytetrahydropyranyl, piperidinyl, difluoro-piperidinyl, (cyano)(methyl)piperidinyl, (hydroxy)(nitromethyl)piperidinyl, (hydroxy)-(methyl)piperidinyl, (hydroxy)(trifluoromethyl)piperidinyl, (hydroxymethyl)(methyl)-piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)-piperidinyl, (carboxy)(ethyl)piperidinyl, (carboxy)(trifluoromethyl)piperidinyl, (carboxy)-(hydroxy)piperidinyl, (carboxy)(hydroxymethyl)piperidinyl, (carboxy)(methoxy)-piperidinyl, (amino)(carboxy)piperidinyl, carboxymethylpiperidinyl, methoxycarbonylpiperidinyl, (methoxycarbonyl)(methyl)piperidinyl, (ethyl)(methoxycarbonyl)piperidinyl, (isopropyl)(methoxycarbonyl)piperidinyl, (methoxy)(methoxycarbonyl)piperidinyl, (carboxy)(methoxycarbonyl)piperidinyl, ethoxycarbonylpiperidinyl, (ethoxycarbonyl)-(fluoro)piperidinyl, (ethoxycarbonyl)(methyl)piperidinyl, (ethoxycarbonyl)(trifluoro-methyl)piperidinyl, (ethoxycarbonyl)(hydroxymethyl)piperidinyl, (n-butoxycarbonyl)-(methyl)piperidinyl, (methyl)(morpholinylethoxycarbonyl)piperidinyl, ethoxycarbonylmethylpiperidinyl, methylsulphonylaminocarbonylpiperidinyl, acetylaminosulphonyl-piperidinyl, methoxyaminocarbonylpiperidinyl, tetrazolylpiperidinyl, hydroxyoxadiazolyl-piperidinyl, aminosulphonylpiperidinyl, piperazinyl, methylpiperazinyl, cyanoethylpiperazinyl, trifluoroethyl-piperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, (tert-butoxycarbonyl)piperazinyl, tetrazolylmethylpiperazinyl, trioxohexahydro-[1,2,5]thiadiazolo[2,3-a]pyrazinyl, morpholinyl, dimethylmorpholinyl, hydroxymethylmorpholinyl, carboxymorpholinyl, (carboxy)(methyl)morpholinyl, carboxymethyl-morpholinyl, thiomorpholinyl, oxothiomorpholinyl, dioxothiomorpholinyl, carboxy-azepanyl, carboxyoxazepanyl, oxodiazepanyl, (methyl)(oxo)diazepanyl, dioxo-thiadiazepanyl, carboxy-3-azabicyclo[3.1.0]hexanyl, (carboxy)(methyl)-3-azabicyclo-[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, 3,7-dioxa-9-azabicyclo[3.3.1]nonanyl, carboxy-5-azaspiro[2.3]hexanyl, (carboxy)(methyl)-5-azaspiro-[2.3]hexanyl, carboxy-5-azaspiro[2.4]heptanyl, carboxy-2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl, (dioxo)(methyl)-2,4,8-triazaspiro[4.5]decanyl, 3,6-epiminofuro[3.2-b]furanyl-pyrimidinyl, methylsulphoximinyl, (methyl)cyclobutyldiol, (imino)(oxo)thiazinanyl, (oxo)thiazinanyl, (dioxo)thiazinanyl or (methyl)triazolyl.

Selected values of $R^9$ include chloromethyl, hydroxymethyl, methoxy, methylsulphonyl, methylsulphonylmethyl, piperazinyl, (tert-butoxycarbonylpiperazinyl), tetrahydropyranyl, (carboxy)(methyl)piperidinyl, methoxycarbonylpiperidinyl, (ethoxycarbonyl)-(methyl)piperidinyl, morpholinyl, 5-methyl-1H-1,2,4-triazolyl, methylsulphoximinyl, hydroxyisopropyl, fluoroisopropyl and cyanoisopropyl.

Illustrative values of $R^9$ include chloromethyl, hydroxymethyl, methoxy, methylsulphonyl, methylsulphonylmethyl, piperazinyl, (tert-butoxycarbonylpiperazinyl), tetrahydropyranyl, (carboxy)(methyl)piperidinyl, methoxycarbonylpiperidinyl, (ethoxycarbonyl)-(methyl)piperidinyl, morpholinyl, 5-methyl-1H-1,2,4-triazolyl and methylsulphoximinyl.

In one embodiment $R^{10}$ represents hydrogen. In a second embodiment, $R^{10}$ represents halogen. In a third embodiment, $R^{10}$ represents cyano. In a fourth embodiment, $R^{10}$ represents trifluoromethyl. In a fifth embodiment, $R^{10}$ represents hydroxy. In a sixth embodiment, $R^{10}$ represents —$NR^bR^c$. In one aspect of this embodiment $R^{10}$ represents $NH_2$. In a seventh embodiment, $R^{10}$ represents —$OR^a$. In one aspect of that embodiment, $R^{10}$ represents methoxy. In an eighth embodiment, $R^{10}$ represents $C_{1-6}$ alkyl. In one aspect of that embodiment, $R^{10}$ represents methyl. In a ninth embodiment, $R^{10}$ represents $C_{1-6}$ alkylsulphonyl. In one aspect of that embodiment, $R^{10}$ represents methylsulphonyl.

In one embodiment $R^{11}$ represents hydrogen. In a second embodiment, $R^{11}$ represents halogen. In a third embodiment, $R^{11}$ represents cyano. In a fourth embodiment, $R^{11}$ represents trifluormethyl. In a fifth embodiment, $R^{11}$ represents hydroxy. In a sixth embodiment, $R^{11}$ represents —$NR^bR^c$. In one aspect of this embodiment $R^{11}$ represents $NH_2$. In a seventh embodiment, $R^{11}$ represents —$OR^a$. In one aspect of that embodiment, $R^{11}$ represents methoxy. In an eighth embodiment, $R^{11}$ represents $C_{1-6}$ alkyl. In one aspect of that embodiment, $R^{11}$ represents methyl. In a ninth embodiment, $R^{11}$ represents $C_{1-6}$ alkylsulphonyl. In one aspect of that embodiment, $R^{11}$ represents methylsulphonyl.

Particular values of $R^{10}$ and $R^{11}$ include hydrogen, methyl and methylsulphonyl.

Generally, $R^{12}$ is hydrogen or $C_{1-6}$ alkyl.

Particular values of $R^{12}$ include hydrogen and methyl.

Particular sub-groups of the compounds of formula (IIB) above are represented by the compounds of formula (IIC), (IID), (IIE), (IIF), (IIG), (IIH), (III), (IIK), (IIL), (IIM) and N-oxides thereof, and pharmaceutically acceptable salts and solvates thereof, and glucuronide derivatives thereof, and co-crystals thereof:

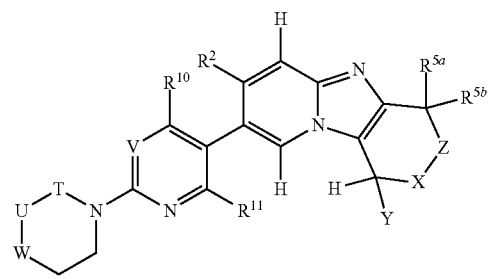
(IIC)

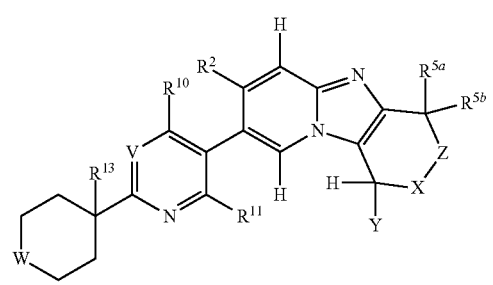
(IID)

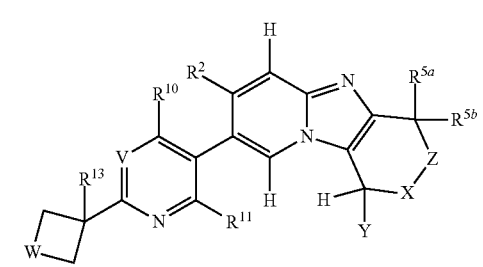
(IIE)

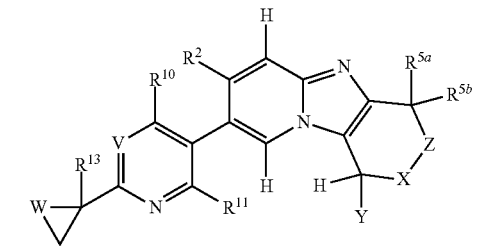
(IIF)

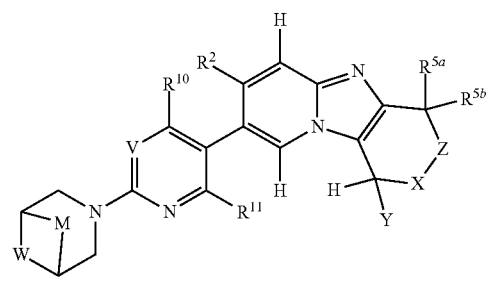
(IIG)

-continued

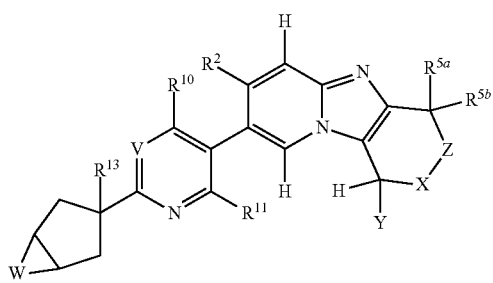
(IIH)

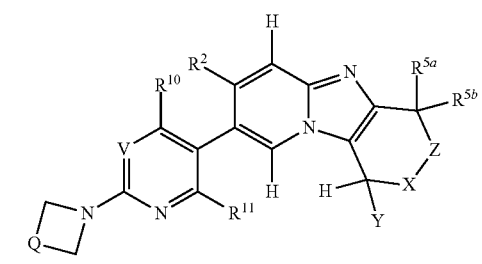
(IIJ)

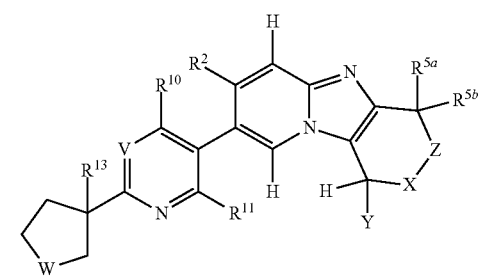
(IIK)

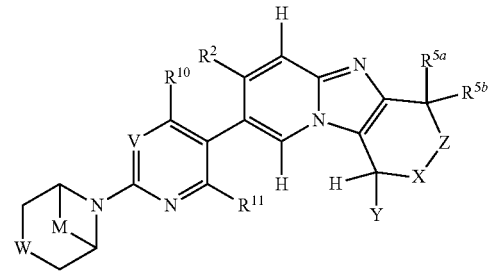
(IIL)

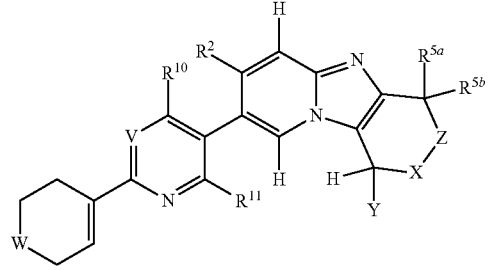
(IIM)

wherein

T represents —CH$_2$— or —CH$_2$CH$_2$—;

U represents C(O) or S(O)$_2$;

W represents O, S, S(O), S(O)$_2$, N(R$^{14}$), S(O)(N—R$^d$) or C(R$^{15}$)(R$^{16}$);

-M- represents —CH$_2$—, —CH$_2$CH$_2$— or CH$_2$—W—CH$_2$—;

Q represents C(R$^{15}$)(R$^{16}$);

R$^{13}$ represents hydrogen, halogen, cyano, halo(C$_{1-6}$)alkyl, hydroxy, C$_{1-6}$ alkoxy, C$_{1-6}$ alkylthio, C$_{1-6}$ alkylsulphinyl, $C_{1-6}$ alkylsulphonyl, amino, $C_{1-6}$ alkylamino, di($C_{1-6}$)alkylamino, ($C_{2-6}$)alkylcarbonylamino, ($C_{2-6}$)alkylcarbonylamino($C_{1-6}$)alkyl, ($C_{1-6}$)alkyl-sulphonylamino or ($C_{1-6}$)alkylsulphonylamino($C_{1-6}$)alkyl;

$R^{14}$ represents hydrogen, cyano($C_{1-6}$)alkyl, $C_{1-6}$ alkyl, trifluoromethyl, trifluoro-ethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety Ω as defined herein, —($C_{1-6}$)alkyl-Ω, aminocarbonyl, $C_{1-6}$ alkylaminocarbonyl, di($C_{1-6}$)alkylaminocarbonyl, aminosulphonyl or di($C_{1-6}$)alkylamino-sulphonyl;

$R^{15}$ represents hydrogen, halogen, cyano, hydroxy, hydroxy($C_{1-6}$)alkyl, $C_{1-6}$ alkylsulphonyl, formyl, $C_{2-6}$ alkylcarbonyl, alkyl)aminocarbonyl, carboxy, carboxy($C_{1-6}$) alkyl, $C_{2-6}$ alkoxycarbonyl, $C_{2-6}$ alkoxycarbonyl($C_{1-6}$)alkyl, aminosulphonyl, ($C_{1-6}$)alkyl-sulphoximinyl, [($C_{1-6}$)alkyl][N—($C_{1-6}$)alkyl]sulphoximinyl, a carboxylic acid isostere or prodrug moiety Ω as defined herein, or —($C_{1-6}$)alkyl-Ω;

$R^{16}$ represents hydrogen, halogen, $C_{1-6}$ alkyl, $C_{3-7}$ cycloalkyl, trifluoromethyl, hydroxy, hydroxy-($C_{1-6}$)alkyl, $C_{1-6}$ alkoxy, amino or carboxy; and V, Y, X, Z, $R^2$, $R^{5a}$, $R^{5b}$, $R^{10}$ and $R^{11}$ are as defined above.

In one embodiment, T represents —$CH_2$—. In a second embodiment T represents —$CH_2CH_2$;

In one embodiment, U represents —C(O). In another embodiment U represents $S(O)_2$.

Generally, W represents O, $S(O)_2$, $S(O)(N—R^d)$, $N(R^{14})$ or $C(R^{15})(R^{16})$.

Typically, W represents O, $N(R^{14})$ or $C(R^{15})(R^{16})$.

In a first embodiment, W represents O. In a second embodiment, W represents S. In a third embodiment, W represents S(O). In a fourth embodiment, W represents $S(O)_2$. In a fifth embodiment, W represents $N(R^{14})$. In a particular aspect of this embodiment, W represents —NH. In a sixth embodiment, W represents $C(R^{15})(R^{16})$. In a seventh embodiment W represents $S(O)(N—R^d)$. In a particular aspect of that embodiment, W represents S(O)(NH).

In one embodiment, -M- represents —$CH_2$—. In a second embodiment, -M- represents —$CH_2CH_2$—. In a third embodiment M represents $CH_2$—W—$CH_2$. In one aspect of that embodiment, M represents $CH_2$—O—$CH_2$. In a second aspect of that embodiment, M represents $CH_2$—S(O)(N—$R^d$)—$CH_2$. In a third aspect of that embodiment, M represents $CH_2$—S—$CH_2$. In a fourth aspect of that embodiment, M represents $CH_2$—S(O)—$CH_2$. In a fifth aspect of that embodiment, M represents $CH_2$—$S(O)_2$—$CH_2$. In a sixth aspect of that embodiment, M represents $CH_2$—$N(R^{14})$—$CH_2$. In a seventh aspect of that embodiment, M represents $CH_2$—$C(R^{15})(R^{16})$—$CH_2$.

In a first embodiment, $R^{13}$ represents hydrogen. In a second embodiment, $R^{13}$ represents halogen. In one aspect of that embodiment, $R^{13}$ represents fluoro. In a third embodiment, $R^{13}$ represents halo($C_{1-6}$)alkyl. In one aspect of that embodiment, $R^{13}$ represents fluoromethyl. In another aspect of that embodiment $R^{13}$ represents trifluoromethyl. In a fourth embodiment, $R^{13}$ represents hydroxy. In a fifth embodiment, $R^{13}$ represents $C_{1-6}$ alkoxy. In a particular aspect of that embodiment, $R^{13}$ represents methoxy. In a sixth embodiment, $R^{13}$ represents $C_{1-6}$ alkylthio. In a particular aspect of that embodiment, $R^{13}$ represents methylthio. In a seventh embodiment, $R^{13}$ represents $C_{1-6}$ alkylsulphinyl. In a particular aspect of that embodiment, $R^{13}$ represents methylsulphinyl. In an eighth embodiment, $R^{13}$ represents $C_{1-6}$ alkylsulphonyl. In a particular aspect of that embodiment, $R^{13}$ represents methylsulphonyl. In a ninth embodiment, $R^{13}$ represents amino. In a tenth embodiment, $R^{13}$ represents $C_{1-6}$ alkylamino. In a particular aspect of that embodiment, $R^{13}$ represents methylamino. In an eleventh embodiment, $R^{13}$ represents di($C_{1-6}$)alkylamino. In a particular aspect of that embodiment, $R^{13}$ represents dimethylamino. In a twelfth embodiment, $R^{13}$ represents ($C_{2-6}$) alkylcarbonylamino. In a particular aspect of that embodiment, $R^{13}$ represents acetylamino. In a thirteenth embodiment, $R^{13}$ represents ($C_{2-6}$)alkylcarbonylamino ($C_{1-6}$)alkyl. In a particular aspect of that embodiment, $R^{13}$ represents acetylaminomethyl. In a fourteenth embodiment, $R^{13}$ represents ($C_{1-6}$)alkylsulphonyl-amino. In a particular aspect of that embodiment, $R^{13}$ represents methylsulphonylamino. In a fifteenth embodiment, le represents ($C_{1-6}$) alkylsulphonylamino($C_{1-6}$)alkyl. In a particular aspect of that embodiment, le represents methylsulphonylaminomethyl. In a sixteenth embodiment, $R^{13}$ represents cyano.

Typically, $R^{13}$ represents hydrogen, halogen, halo($C_{1-6}$) alkyl, hydroxy or ($C_{2-6}$)alkylcarbonylamino($C_{1-6}$)alkyl.

Selected values of $R^{13}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{13}$ include hydrogen, fluoro, fluoromethyl, hydroxy and acetylaminomethyl.

Suitably, $R^{13}$ represents hydrogen, hydroxy or fluoro.

Typically, $R^{14}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl-($C_{1-6}$)alkyl, tetrazolyl($C_{1-6}$)alkyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylamino-sulphonyl.

Suitably, $R^{14}$ represents hydrogen, $C_{1-6}$ alkyl or $C_{2-6}$ alkylcarbonyl.

Typical values of $R^{14}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylamino-carbonyl, dimethylaminocarbonyl, aminosulphonyl, methylaminosulphonyl and dimethylaminosulphonyl.

Particular values of $R^{14}$ include hydrogen, methyl and acetyl.

In a particular embodiment $R^{14}$ represents hydrogen.

In a selected embodiment, $R^{14}$ represents $C_{1-6}$ alkyl.

In yet another particular embodiment, $R^{14}$ represents $C_{2-6}$ alkylcarbonyl.

Generally, $R^{15}$ represents halogen, carboxy, carboxy ($C_{1-6}$)alkyl, $C_{2-6}$ alkoxycarbonyl, di($C_{1-6}$ alkyl)aminocarbonyl, $C_{2-6}$ alkoxycarbonyl($C_{1-6}$)alkyl, a carboxylic acid isostere or prodrug moiety Ω as defined herein, or —($C_{1-6}$)alkyl-Ω.

Typically, $R^{15}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylaminosulphonyl, ($C_{1-6}$)alkoxyaminocarbonyl, tetrazolyl or hydroxyoxadiazolyl.

Typical values of $R^{15}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, dimethylaminocarbonyl, acetylaminosulphonyl, methoxyaminocarbonyl, tetrazolyl and hydroxyoxadiazolyl.

In a selected embodiment, $R^{15}$ represents carboxy.

Generally, $R^{16}$ represents hydrogen, halogen or $C_{1-6}$ alkyl.

Suitably, $R^{16}$ represents hydrogen or $C_{1-6}$ alkyl.

Selected values of $R^{16}$ include hydrogen, fluoro, methyl, ethyl, isopropyl, cyclopropyl, trifluoromethyl, hydroxy, hydroxymethyl, methoxy, amino and carboxy.

Particular values of $R^{16}$ include hydrogen and methyl.

In a first embodiment, $R^{16}$ represents hydrogen.

In a second embodiment, $R^{16}$ represents halogen. In one aspect of that embodiment, $R^{16}$ represents fluoro. In a third embodiment, $R^{16}$ represents $C_{1-6}$ alkyl. In a first aspect of that embodiment, $R^{16}$ represents methyl. In a second aspect of that embodiment, $R^{16}$ represents ethyl. In a third aspect of that embodiment, $R^{16}$ represents isopropyl. In a fourth embodiment, $R^{16}$ represents trifluoromethyl. In a fifth embodiment, $R^{16}$ represents hydroxy. In a sixth embodiment, $R^{16}$ represents hydroxy($C_{1-6}$)alkyl. In one aspect of that embodiment, $R^{16}$ represents hydroxymethyl. In a seventh embodiment, $R^{16}$ represents $C_{1-6}$ alkoxy. In one aspect of that embodiment, le represents methoxy. In an eighth embodiment, $R^{16}$ represents amino. In a ninth embodiment, $R^{16}$ represents carboxy. In a tenth embodiment, $R^{16}$ represents a $C_{3-7}$ cycloalkyl. In one aspect of this embodiment, $R^{16}$ represents cyclopropyl.

Alternative sub-groups of compounds of formula (IIA) are represented by the compounds of formula (IIN), (IIP), (IIQ), (IIS), (IIT), and N-oxides thereof, and pharmaceutically acceptable salts and solvates thereof, and glucuronide derivatives thereof, and co-crystals thereof:

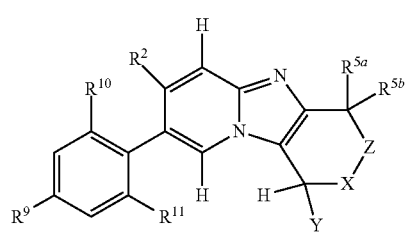

(IIN)

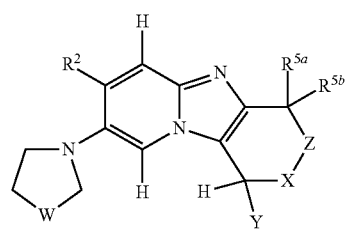

(IIP)

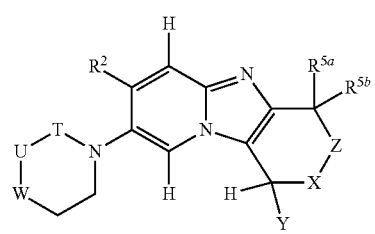

(IIQ)

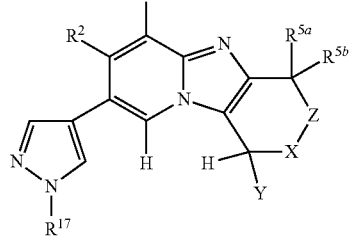

(IIS)

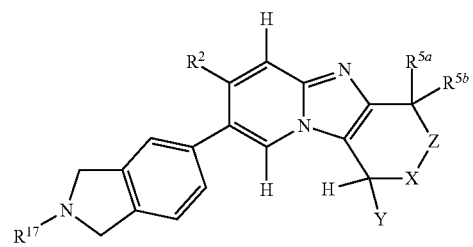

(IIT)

Wherein
$R^{17}$ independently represents hydrogen, $C_{1-6}$ alkyl, $C_{1-6}$ alkylsulphonyl, $C_{1-6}$ alkylsulphonylalkyl, trifluoromethyl or $C_{2-6}$ alkoxycarbonyl; and
X, Z, U, T, W, Y, $R^2$, $R^{5a}$, $R^{5b}$, $R^9$, $R^{10}$ and $R^{11}$ are as defined above.

In one embodiment $R^{17}$ represents hydrogen. In a second embodiment $R^{17}$ represents $C_{1-6}$ alkyl. In a particular aspect of this embodiment, $R^{17}$ represents methyl. In a third embodiment, $R^{17}$ represents $C_{1-6}$ alkylsulphonyl. In one aspect of this embodiment $R^{17}$ represents methylsulphonyl. In a fourth embodiment, $R^{17}$ represents $C_{1-6}$ alkylsulphonylalkyl. In one aspect of that embodiment, $R^{17}$ represents methylsulphonylmethyl. In another aspect of that embodiment, $R^{17}$ represents methylsulphonylethyl. In a fifth embodiment, $R^{17}$ represents trifluoromethyl. In a sixth embodiment, $R^{17}$ represents C2-6alkoxycarbonyl. In one aspect of that embodiment, $R^{17}$ represents tert-butoxycarbonyl.

An alternative sub-class of compounds according to the invention is represented by the compounds of formula (IIW) and N-oxides thereof, and pharmaceutically acceptable salts and solvates thereof, and glucuronide derivatives thereof, and co-crystals thereof:

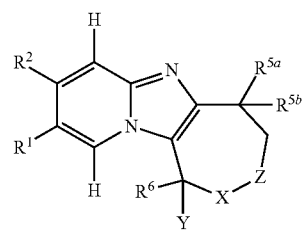

(IIW)

X, Z, Y, $R^1$, $R^2$, $R^{5a}$, $R^{5b}$ and $R^6$ are as defined above.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

The compounds of formula (I) above, in particular subclass of compounds (IIA) above wherein Z is a methylene, may be prepared by a process which comprises reacting a compound of formula (III) with a compound of formula (IV), to afford a compound of formula (V), wherein $R^d$, $R^1$, $R^2$, $R^3$ $R^4$, $R^{5a}$ and $R^{5b}$ are as defined above. $L^1$ represents a suitable leaving group.

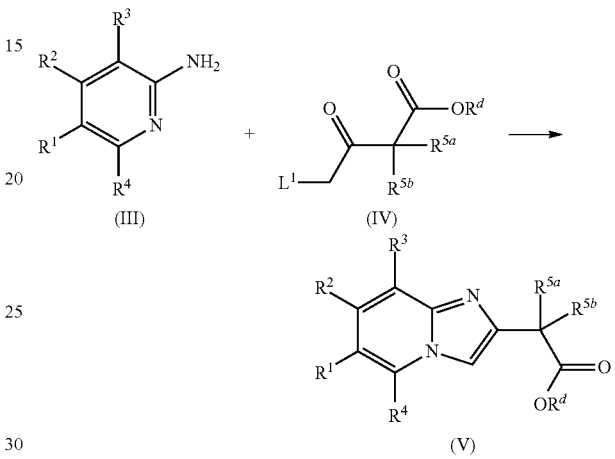

The leaving group $L^1$ is typically a halogen atom, e.g. bromine.

The reaction is conveniently effected at an elevated temperature in a suitable solvent, e.g. a $C_{1-4}$ alkanol such as ethanol, or an ether such as 1,4-dioxane or dimethoxyethane.

An intermediate of formula (III) wherein $R^1$ is hydrogen may be transformed into the corresponding intermediate wherein $R^1$ is a bromine or a chlorine, by treatment with N-Chloro or N-Bromo succinimide in a suitable solvent, e.g. acetonitrile.

Compound of formula (V) may be transformed into compound of formula (VI) below, wherein E is —OH or E is —NH$_2$, m represents an integer equal to 1 and $R^d$, $R^1$, $R^2$, $R^3$ $R^4$, $R^{5a}$ and $R^{5b}$ are as defined above.

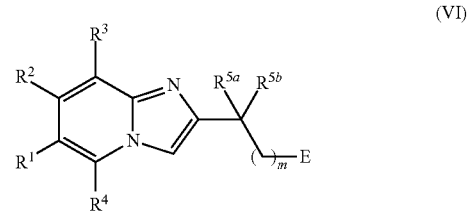

When E is —OH, transformation of compound of formula (V) into compound of formula (VI) is conveniently effected by treatment with a reducing agent, e.g. di-isobutyl-aluminiumlithium hydride, in a suitable solvent, e.g. THF.

Compound of formula (VI) wherein E is —NH$_2$ is obtained in two steps from compound of formula (VI) wherein E is —OH. First step is performed by treating compound of formula (VI) wherein E is —OH by with phtalimide, triphenylphosphine, and diisopropyldiazadicarboxylate in a suitable solvent, e.g. THF. The compound thereby obtained, is further treated with hydrazine in a suitable solvent, e.g. methanol, at elevated temperature, to afford compound of formula (VI) wherein E is —NH$_2$.

The compounds of formula (I) above, in particular sub-class of compounds (IIA) above wherein X is a methylene and R$^{5a}$ and R$^{5b}$ are hydrogen, may be prepared by a process which comprises reacting a compound of formula (III) with a compound of formula (VII), to afford a compound of formula (VIII), according to the following scheme, wherein L$^1$, R$^d$, R$^1$, R$^2$, R$^3$ and R$^4$ are as defined above.

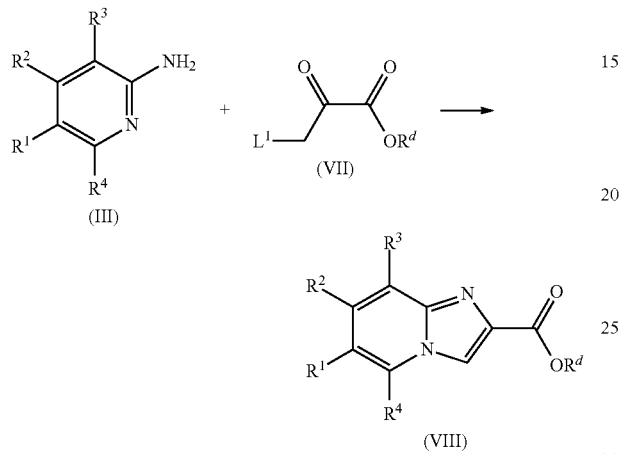

The reaction is conveniently effected at an elevated temperature in a suitable solvent, e.g. a C$_{1-4}$ alkanol such as ethanol, or an ether such as 1,4-dioxane or dimethoxyethane.

Compound of formula (VIII) may be transformed into compound of formula (VI) wherein m represents an integer equal to 0, R$^{5a}$ and R$^{5b}$ are hydrogen and E is —OH, in an analogous method to the one described here above for the transformation of compound of formula (V).

Compound of formula (VI) wherein E is —OH may be transformed into corresponding compound of formula (VI) wherein E is halogen according to methods known to the one skilled in the art.

In particular, when E is chloro, compounds of formula (VI) wherein E is —OH are treated with thionyl chloride in a suitable solvent, e.g. dichloromethane, to afford corresponding compounds of formula (VI) wherein E represents chloro.

Compound of formula (VI) wherein m represents an integer equal to 0, R$^{5a}$ and R$^{5b}$ are hydrogen and E represents chloro may be conveniently transformed into a compounds of formula (VI) wherein E is —O—CH$_2$—C(OH)—Y, by treatment with the stannylene acetal of Y—(CHOH)—CH$_2$OH in the presence of Cesium fluoride in a suitable solvent, e.g. dimethylformamide.

Compounds of formula (VI) above may generally be cyclized into compounds of formula (I), in particular compounds of sub-class (IIA), according to the following procedures:

(i) When m represents an integer equal to 1, R$^{5a}$ and R$^{5b}$ are hydrogen, E is —NH$_2$, the transformation may be performed with Y—(CO)—H or its corresponding acetal, in the presence respectively of an acid, e.g. para-toluenesulfonic acid, or in the presence of a slat, e.g. magnesium chloride, in a suitable solvent e.g. toluene or acetonitrile, at elevated temperature, to afford compound of formula (I), in particular sub-class of compounds of formula (IIA) wherein X is —NH and Z is methylene.

(ii) A similar transformation may be performed when E is —OH thereby affording compound of formula (I), in particular sub-class of compounds of formula (IIA) wherein X is oxygen and Z is methylene.

(iii) As an alternative to the method under (i) and (ii) above, compound of formula (I), in particular sub-class of compounds of formula (IIA) wherein X is oxygen or —NH, Z is methylene and R$^{5a}$ and R$^{5b}$ are hydrogen may be prepared by reacting the acetal of Y—(CO)—H with pyridinium-para-toluenesulphonate in a suitable solvent, e.g. acetonitrile, using Microwave according to the Oxa-Pictet-Spengler reaction. The acetal of Y—(CO)—H may, for example, be conveniently prepared by reacting Y—(CO)—H with trimethylorthoformate in the presence of ammonium chloride in a suitable solvent, e.g. methanol.

(iv) When m represents an integer equal to 0, R$^{5a}$ and R$^{5b}$ are hydrogen, E is —O—CH$_2$—C(OH)—Y, compound of formula (VI) may be transformed into compound of formula (I), in particular sub-class of compounds of formula (IIA), wherein X is methylene, Z is oxygen, and R$^{5a}$ and R$^{5b}$ are hydrogen, by reaction with triethylamine and trifluoromethanesulphonic anhydride, at low temperature, in a suitable solvent, e.g. dichloromethane.

Alternatively, process of preparation of compounds of formula (I), in particular sub-class of compounds of formula (IIA), wherein X is oxygen, Z is methylene, R$^{5a}$ is hydroxy and R$^{5b}$ is hydrogen may include reaction of an intermediate compound of formula (IX) with an intermediate compound of formula (X) wherein L$^2$ is a halogen atom, e.g. chloro.

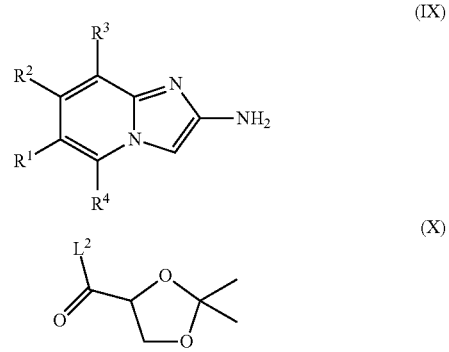

The reaction is conveniently performed in the presence of potassium iodide in a suitable solvent, e.g. methanol, at elevated temperature to afford corresponding compound of formula (VI) wherein R$^{5a}$ is hydroxy, R$^{5b}$ is hydrogen, m represents an integer equal to 1 and E is —OH.

Said compound of formula (VI) is further cyclized into the corresponding compound of formula (I), in particular sub-class of compounds of formula (IIA), wherein X is oxygen, Z is methylene, R$^{5a}$ is hydroxy and R$^{5b}$ is hydrogen, by treatment with the acetal of Y—(CO)—H in analogous conditions as those described above for other compounds of formula (VI), as will be apparent to the one skilled in the art.

A compound of formula (I) wherein n equals 1, X is methylene, Z is NH, R$^6$ is hydrogen, and R$^{5a}$ and R$^{5b}$ together with the carbon to which they are attached form a carbonyl, may be prepared by reacting intermediate of formula (XII) with sodium azide The reaction is conveniently effected at low temperature, e.g., 0° C., in a suitable solvent, e.g., tetrahydrofuran.

(XII)

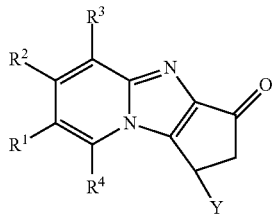

Intermediate of formula (XII) can be prepared by intramolecular cyclization of intermediate of formula (XIII), in the presence of a suitable, e.g. potassium tert-butanolate, base, in a suitable solvent, e.g. terahydrofuran.

(XIII)

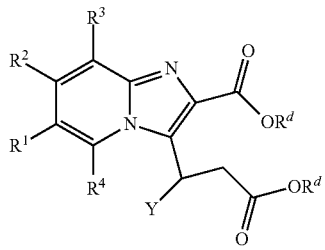

Intermediate of formula (XIII) can be prepared by reacting intermediate of formula (XIV) with potassium hexamethyldisilazane (KHMDS), in a suitable solvent, e.g. tetrahydrofuran, at low temperature, in the presence of $L^1$-$CH_2$—$COOR^d$, wherein $L^1$ and $R^d$ are as defined herein.

(XIV)

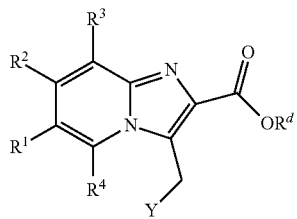

Intermediate of formula (XIV) may be prepared by reacting intermediate (III) as defined herein with corresponding intermediate (XV), in conditions analogous as those described to make intermediate of formula (VIII).

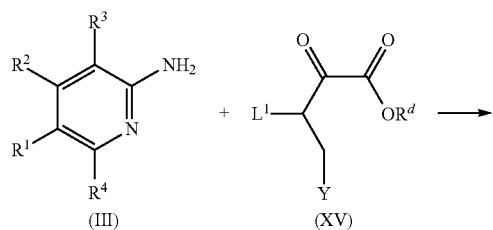

(XIV)

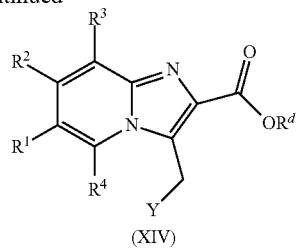

Compound of formula (I), in particular sub-class of compounds (IIW) may be prepared according to a process which includes reacting a compound of formula (IX) with a compound of formula (XI):

(XI)

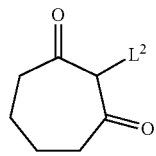

It will be understood that any compound of formula (I) initially obtained from any of the above processes may, where appropriate, subsequently be elaborated into a further compound of formula (I) by techniques known in the art.

References to compound of formula (I) below will be understood as including all potential subclasses and subgroups mentioned here above.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a hydroxy group and $R^{5b}$ is a hydrogen using for example lithium-tri-sec-butyl-borohydride or sodium borohydride in a suitable solvent e.g. THF.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a trifluoromethyl and $R^{5b}$ is a hydroxy by treatment with trifluormethylsilane at room temperature in a suitable solvent e.g. dimethoxyethane.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a ($C_{1-6}$ alkyl)sulphonylaryloxy trifluoromethyl and $R^{5b}$ is a hydrogen by treatment with ($C_{1-6}$ alkyl)sulphonylphenol, in the presence of Disiopropyl ϵ-1,2-diazenedicarboxylate, in a suitable solvent, e.g THF.

A compound of formula (I) which contains a carbonyl group, in particular a compound of formula (I) wherein $R^{5a}$ and $R^{5b}$ with the carbon atom to which they are attached form a carbonyl may transformed into the corresponding compound wherein $R^{5a}$ and $R^{5b}$ together with the carbon to which they are attached form a-C=N—OH, by treatment, for example with hydroxylamine chloride in the presence of pyridine in the presence of a suitable solvent such as ethanol.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ and $R^{5b}$ are hydrogen for example by treatment with iodotrimethylsilane in a suitable solvent, e.g. acetonitrile.

A compound of formula (I) which contains a hydroxy group, in particular a compound of formula (I) wherein $R^{5a}$ is a hydroxy group and $R^{5b}$ is a hydrogen, may be transformed in a two step reaction into corresponding compound wherein $R^{5a}$ is $NH_2$ and $R^{5b}$ is hydrogen for example by (i) treatment with diphenylphosphorylazide and 1,8-diazabicyclo[5.4.0]undec-7-ene. This reaction is conveniently performed at 0° C. in THF; (ii) subsequent aza-wittig reaction using $PPh_3$ in a suitable solvent, e.g. a mixture of water and toluene.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ is F and $R^{5b}$ is hydrogen by treatment with diethylaminosulfur trifluoride in a suitable solvent, e.g. THF.

A compound of formula (I) which contains a hydroxy group, in particular a compound of formula (I) wherein $R^{5a}$ is a hydroxy group and $R^{5b}$ is a hydrogen, may be transformed into the corresponding compound of formula (I) wherein $R^{5a}$ is a $C_{1-4}$ alkyl, e.g. methyl, and $R^{5b}$ is a hydrogen by treatment for example with an alkylmagnesium bromide in a suitable solvent, for example diethylether.

A compound of formula (I) which contains a hydroxy group, in particular a compound of formula (I) wherein $R^{5a}$ is a hydroxy group and $R^{5b}$ is a hydrogen may be transformed into the corresponding compound wherein $R^{5a}$ is a $C_{1-4}$ alkoxy, e.g. methoxy, and $R^{5b}$ is a hydrogen by treatment with a base e.g. sodium hydride, in a suitable solvent, e.g. THF, in the presence of a suitable alkylation agent, such as an alkylhalide, e.g. methyliodide.

A compound of formula (I) which contains a hydroxy group may be alkylated by treatment with the appropriate alkyl halide in the presence of a base, e.g. sodium hydride, or silver oxide. A compound of formula (I) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be methylated by treatment with formaldehyde in the presence of a reducing agent, e.g. sodium triacetoxyborohydride.

A compound of formula (I) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkyl-sulphonyl halide, e.g. a $C_{1-6}$ alkylsulphonyl chloride such as methanesulphonyl chloride.

A compound of formula (I) containing the moiety —S— may be converted into the corresponding compound containing the moiety —S(O)— by treatment with 3-chloroperoxybenzoic acid. Likewise, a compound of formula (I) containing the moiety —S(O)— may be converted into the corresponding compound containing the moiety —S(O)$_2$— by treatment with 3-chloroperoxybenzoic acid. Alternatively, a compound of formula (I) containing the moiety —S— may be converted into the corresponding compound containing the moiety —S(O)$_2$— by treatment with Oxone® (potassium peroxymonosulfate).

A compound of formula (I) containing an aromatic nitrogen atom may be converted into the corresponding N-oxide derivative by treatment with 3-chloroperoxybenzoic acid.

A compound of formula (I) which contains a carbonyl may be converted into the corresponding alcohol by treatment with a suitable borohydride, e.g. lithium-tri-sec-butylborohydride or sodium borohydride, in a suitable solvent e.g. THF.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(O), bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate. This reaction may conveniently be performed in a 1,4-dioxane with or without the use of micro wave technology. Alternatively, the above reaction can be effected in the presence of tris(dibenzylideneacetone)dipalladium(0)-chloroform and dicyclo hexyl-[2-(2,4,6-triisopropylphenyl)phenyl]phosphane, in a polar solvent, e.g., n-butanol, at high temperature.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato) diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(O), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine) palladium(O), typically in the presence of copper(I) iodide and a base, e.g. an organic base such as triethylamine.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(O), and a reagent such as tri(ortho-tolyl)phosphine.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) wherein $R^1$ represents 6-methoxypyridin-3-yl may be converted into the corresponding compound wherein $R^1$ represents 2-oxo-1,2-dihydropyridin-5-yl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5-methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—CO$_2$H) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —C(CH$_3$)(OH)— moiety by treatment with methylmagnesium bromide. Similarly, a compound of formula (I) containing a carbonyl (C=O) moiety may be converted into the corresponding compound containing a —C(CF$_3$)(OH)— moiety by treatment with (trifluoromethyl)trimethylsilane and cesium fluoride. A compound of formula (I) containing a carbonyl (C=O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropyl-biphenyl (XPhos) or 2,2'-bis(diphenylphosphino)-1,1'-binaphthalene (BINAP) or Xantphos and a base, e.g. an inorganic base such as sodium tert-butoxide or cesium fluoride. Alternatively, the reaction may be effected using palladium diacetate, in the presence of a reagent such as [2',6'-bis(propan-2-yloxy)biphenyl-2-yl](dicyclohexyl)phosphane and a base, e.g. an inorganic base such as cesium carbonate.

A compound of formula (I) containing an oxo moiety can be converted into the corresponding compound containing an ethoxycarbonylmethylidene moiety by treatment with triethyl phosphonoacetate in the presence of a base such as sodium hydride.

A compound of formula (I) containing a C—OH moiety may be converted into the corresponding compound containing a C—F moiety by treatment with difluoro(morpholino)sulfonium tetrafluoroborate, in a suitable solvent, e.g. dichloromethane, at low temperature.

A compounds of formula (IIB) or (IIN) wherein $R^9$ represents ethenyl may be prepared by reacting a compound of formula (IIB) or (IIN) wherein $R^9$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium(II), and a base, e.g. an organic base such as triethylamine.

A compound of formula (IIB) or (IIN) wherein $R^9$ represents halogen, e.g. chloro, may be converted into the corresponding compound wherein $R^9$ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound of formula (IIB) or (IIN) wherein $R^9$ represents a substituent containing at least one nitrogen atom, which substituent is linked to the remainder of the molecule via a nitrogen atom, may be prepared by reacting a compound of formula (IIB) or (IIN) wherein $R^9$ represents halogen, e.g. chloro, with the appropriate compound of formula $R^9$—H [e.g. 2-methoxyethylamine, N-methyl-L-alanine, 2-amino cyclopentanecarboxylic acid, 3-amino cyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole hereinafter referred to as "Compound (A)" can be prepared by the procedure described in Example 499 of WO 2013/186229 (published 19 Dec. 2013); or by a procedure analogous thereto.

Preparation of Fluorescence Conjugate

Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 µL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxy-fluorescein succinimyl ester. The peak areas were 22.0%, 39.6% and 31.4% for the three signals, indicating a 61.6% conversion to the two isomers of the desired fluorescence conjugate at that time-point. Further 20 µL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 µM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 µL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 µM or better.

Reporter Gene Assay
Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g., 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 µM or better.

EXAMPLES

Nomenclature

Compounds were named with the aid of ACD/Name Batch (Network) ver. 12.0 or Accelyrs Draw 4.0

Abbreviations
DCM: Dichloromethane EtOAc: Ethyl acetate
DMF: N,N-Dimethylformamide MeOH: Methanol
DMSO: Dimethylsulfoxide SiO$_2$: Silica
Et$_2$O: Diethyl ether h: H
THF: Tetrahydrofuran AcOH: Acetic acid
r.t.: Room temperature br.: Broad
M: Mass
Brine: Saturated aqueous sodium chloride solution
HPLC: High Performance Liquid Chromatography
LCMS: Liquid Chromatography Mass Spectrometry
ES+: Electrospray Positive Ionisation
TEA: Triethylamine
DIPEA: N,N-di-iso-propylethylamine
DIAD: Diisopropyl (E)-1,2-diazenedicarboxylate
RT: retention time
TBAF tetrabutyl ammonium fluoride
KHMDS: potassium hexamethyldisilazane
Pd$_2$dba$_3$ Tris(dibenzylideneaceton)dipalladium(0)

The methanolic ammonia solution is made by mixing 100 mL of an aq. solution of 37% w/w of NH$_4$OH in 900 mL of MeOH.

Analytical Conditions

All NMRs were obtained either at 300 MHz or 400 MHz.

Compounds were named with the aid of ACD/Name Batch (Network) ver. 12.0 or Accelyrs Draw 4.0

All reactions involving air- or moisture-sensitive reagents were performed under a nitrogen atmosphere using dried solvents and glassware.

All compound GCMS data was determined by using the method below:

ITQ 900 Ion Trap Finnigan mass spectrometer is used for GC-MS analysis. This spectrometer is equipped with a gas chromatograph model Trace GC ultra (Finnigan) fitted with a split/splitless injector. The separation is carried on a FactorFOUR fused-silica column (VF-5MS 15 m×0.25 33 I.D., 1 µm) from Varian. Helium (purity 99.999%) is used as carried gas. Sample (1 µl) is injected in splitless mode and the oven temperature is programmed as follows: 50° C. for 5 min, increasing to 280° C. (23° C./min) and holding for 10 min. The ITQ 900 spectrometer operates in electron impact (EI) or chemical ionization (CI—CH4). The source temperature is set at 150° C.

All compound LCMS data was determined by using the method below:
Waters Acquity-SQD, Waters Acquity UPLC BEH C18, 2.1×50 mm, 1.7 µm column
Mobile phase A: 10 mM Ammonium Formate+0.1% Ammonia
Mobile phase B: 95% MeCN+5% H$_2$O+0.1% Ammonia
Gradient program (Flow Rate 1.0 mL/min, Column Temperature 40° C.):

| Time | A % | B % |
| --- | --- | --- |
| 0.00 | 95 | 5 |
| 0.50 | 95 | 5 |
| 1.75 | 5 | 95 |
| 2.00 | 5 | 95 |
| 2.25 | 95 | 5 |

It will be apparent to the one skilled in the art that different retention times (RT) for GCMS and LCMS data may be obtained if different analytical conditions are used.

Method 2:

Preparative HPLC for all compounds that required it was performed at pH 2.5 using a Luna C18, 21.2 mm, 5 mm column.

Mobile phase A: 99.92% water and 0.08% formic acid.
Mobile phase B: 99.92% MeCN and 0.08% formic acid.
Gradient program (flow rate 25 mL/min), column temperature: ambient, variable gradient.

Intermediate 1

Ethyl 2-(6-chloroimidazo[1,2-a]pyridin-2-yl)acetate

To a solution of 2-amino-5-chloropyridine (10.00 g, 77.79 mmol) in EtOH (100 mL) was added ethyl 4-chloro-3-oxobutanoate (10.58 mL, 77.79 mmol). The reaction was heated to reflux for 4 h. The reaction was cooled to r.t. and water (200 mL) was added and the mixture extracted with DCM (2×200 mL). The organic layer was separated, dried (MgSO$_4$) and concentrated in vacuo to afford the title compound as a yellow solid (5.38 g, 30%). $^1$H NMR (400 MHz, CDCl$_3$) δ 8.15 (d, J 0.8 Hz, 1H), 7.61 (s, 1H), 7.52 (d, J 9.5 Hz, 1H), 7.14 (dd, J 9.6, 1.5 Hz, 1H), 4.24 (q, J 7.1 Hz, 2H), 3.88 (s, 2H), 1.32 (t, J 7.1 Hz, 3H). LCMS (ES$^+$) 197.0/199.0 (M+H)$^+$.

Intermediate 2

2-(6-chloroimidazo[1,2-a]pyridin-2-yl)ethanol

To a solution of Intermediate 1 (2.87 g, 12.02 mmol) in THF (60 mL) at −20° C. was added DIBAL-H (30.04 mL, 30.04 mmol) drop wise. The reaction was stirred for 2 h. The reaction was treated with excess Na$_2$SO$_4$.10H$_2$O and diluted with DCM. The solid was filtered off and the filtrate was concentrated in vacuo to afford the title compound as an orange solid (1.99 g, 84%). $^1$H NMR (400 MHz, CDCl$_3$) δ 8.05 (s, 1H), 7.40 (d, J 9.7 Hz, 1H), 7.32 (s, 1H), 7.05 (m, 1H), 3.93 (m, 2H), 2.93 (t, J 5.4 Hz, 2H). LCMS (ES$^+$) 239.0/241.0 (M+H)$^+$.

Intermediate 3 (Method A)

1-(difluoromethoxy)-2-(dimethoxymethyl)benzene

To a solution of 2-(difluoromethoxy)benzaldehyde (5.51 g, 29.05 mmol) in MeOH (20 mL) was added trimethylorthoformate (4.13 mL, 37.76 mmol) and LiBF$_4$ (0.08 g, 0.87 mmol). The reaction mixture was heated to reflux for 4 h, cooled and treated with NaHCO$_3$ sat. solution (50 mL), extracted with EtOAc (50 mL), dried over MgSO$_4$ and concentrated in vacuo to afford the title compound as a yellow oil (6.30 g, 100%). $^1$H NMR (400 MHz, CDCl$_3$) δ 7.55 (dd, J 7.6, 1.5 Hz, 1H), 7.28 (m, 1H), 7.18 (m, 1H), 7.08 (d, J 8.1 Hz, 1H), 6.40 (t, J 74.6 Hz, 1H), 5.53 (s, 1H), 3.32 (s, 6H).

Intermediate 5

2-[2-(6-chloroimidazo[1,2-a]pyridin-2-yl)ethyl]isoindoline-1,3-dione

To a solution of Intermediate 2 (0.5 g, 2.54 mmol) in THF (12 mL), was added pthalimide (0.29 g, 1.96 mmol) and PPh$_3$ (1.18 g, 4.50 mmol). The reaction mixture was cooled to 0° C. and DIAD (0.51 g, 2.54 mmol) was added drop wise. The reaction mixture was allowed to warm to r.t. and stirred for 12 h. The reaction was diluted with DCM (10 mL), the organics were washed with water (10 mL) and dried over MgSO$_4$ and concentrated in vacuo. The residue was purified by column chromatography (SiO$_2$, 100 DCM to 90 DCM/10 methanolic ammonia), yielding the title compound as a yellow solid (0.60 g, 72%). $^1$H NMR (400 MHz, CDCl$_3$) δ 8.11 (d, J 1.0 Hz, 1H), 7.85 (dd, J 5.4, 3.1 Hz, 2H), 7.73 (dd, J 5.4, 3.0 Hz, 2H), 7.47 (m, 2H), 7.11 (dd, J 9.6, 1.9 Hz, 1H), 4.13 (t, J 7.2 Hz, 2H), 3.23 (t, J 7.3 Hz, 2H). LCMS (ES$^+$) 326.0/328.0 (M+H)$^+$.

Intermediate 6

2-(6-chloroimidazo[1,2-a]pyridin-2-yl)ethanamine

To a solution of Intermediate 5 (0.60 g, 1.38 mmol) in MeOH (3 mL), hydrazine (0.51 mL, 35% solution in H$_2$O, 5.53 mmol) was added and the mixture was heated to reflux for 4 h. The reaction mixture was diluted in EtOH (10 mL) 3 times and concentrated in vacuo. The residue was triturated in DCM yielding the title compound as an orange solid (0.16 g, 44%). LCMS (ES$^+$) 196.0/198.0 (M+H)$^+$.

Intermediate 7 (Method C)

2-[2-[6-(6-methoxy-3-pyridyl)imidazo[1,2-a]pyridin-2-yl]ethyl]isoindoline-1,3-dione and 2-[2-[6-(6-methoxy-3-pyridyl)imidazo[1,2-a]pyridin-2-yl]ethylcarbamoyl]benzoic acid To a solution of Intermediate 5 (0.85 g, 2.61 mmol) in n-butanol (8.5 mL), 6-methoxy pyridine 3-yl boronic acid (0.60 g, 3.91 mmol), tris(dibenzylideneacetone)dipalladium (0)-chloroform (0.024 g, 0.026 mmol), K$_3$PO$_4$ (1.11 g, 5.22 mmol) and dicyclohexyl-[2-(2,4,6-triisopropylphenyl)phenyl]phosphane (0.05 g, 0.10 mmol) was added, the reaction was degassed 3 times and placed under argon. The reaction mixture was heated to 100° C. for 4 h. The reaction mixture was cooled and treated with NaHCO$_3$ sat. solution (10 mL), extracted with DCM (10 mL), the organics were washed with brine (10 mL) and dried over MgSO$_4$ and concentrated in vacuo. The residue was purified by prep HPLC, yielding the title compounds (quantitative yield). LCMS (ES$^+$) 399.0, 417.0 (M+H)$^+$ respectively.

Intermediate 8

2-[6-(6-methoxy-3-pyridyl)imidazo[1,2-a]pyridin-2-yl]ethanamine

To a solution of Intermediate 8 (1.50 g, 3.77 mmol) in MeOH (6 mL), hydrazine (1.04 mL, 35% solution in H$_2$O, 11.3 mmol) was added and the mixture was heated to reflux for 4 h. The reaction mixture was diluted in EtOH (10 mL) 3 times and concentrated in vacuo. The residue was triturated in DCM yielding the title compound as an orange solid (0.40 g, 40%). $^1$H NMR (400 MHz, CDCl$_3$) δ 8.37 (d, J 2.0 Hz, 1H), 8.20 (d, J 0.7 Hz, 1H), 7.76 (dd, J 8.6, 2.5 Hz, 1H), 7.63 (d, J 9.4 Hz, 1H), 7.49 (s, 1H), 7.33 (dd, J 9.3, 1.7 Hz, 1H), 6.87 (d, J 8.6 Hz, 1H), 4.01 (m, 3H), 3.17 (t, J 6.6 Hz, 2H), 2.97 (t, J 6.5 Hz, 2H). LCMS (ES$^+$) 269.0 (M+H)$^+$.

Intermediate 9

Ethyl 2-(6-bromoimidazo[1,2-a]pyridin-2-yl)acetate

To a solution of 2-amino-5-bromopyridine (25.65 g, 147.41 mmol) in EtOH (400 mL) was added ethyl 4-chloro-3-oxo-butanoate (22.06 mL, 162.16 mmol). The reaction was heated to reflux for 4 h. The reaction was cooled to r.t. and concentrated in vacuo. The residue was triturated with diisopropyl ether and the solid was filtered off and dried in vacuo to afford the title compound (42.0 g, quantitative yield). $^1$H NMR (400 MHz, DMSO-d$_6$) δ 9.32 (s, 1H), 8.20 (s, 1H), 8.01 (m, 1H), 7.90 (d, J 9.4 Hz, 1H), 4.16 (m, 4H), 1.24 (t, J 6.8 Hz, 3H). LCMS (ES$^+$) 283.0/285.0 (M+H)$^+$.

Intermediate 10

2-(6-bromoimidazo[1,2-a]pyridin-2-yl)ethanol

To a solution of Intermediate 10 (10.0 g, 35.32 mmol) in THF (500 mL) at −70° C., lithium triethylborohydride (105.96 mmol, 63.0 mL) was added drop wise and the reaction mixture was stirred at −70° C. for 1 h. The reaction mixture was warmed to 0° C. and treated with NH$_4$Cl sat. (100 mL) and EtOAc (100 mL). The organic layer was separated, dried (MgSO$_4$) and concentrated in vacuo. The residue was purified by column chromatography (SiO$_2$, 100 DCM to 97 DCM/3 methanolic ammonia), yielding the title compound (1.30 g, 15%). $^1$H NMR (400 MHz, CDCl$_3$) δ 8.13 (s, 1H), 7.32 (m, 2H), 7.12 (dd, J 9.5, 1.5 Hz, 1H), 5.27 (s, 1H), 3.96 (t, J 6.0 Hz, 2H), 2.96 (t, J 6.0 Hz, 2H). LCMS (ES$^+$) 241.0/243.0 (M+H)$^+$.

Intermediate 11

2-[2-(6-bromo-imidazo[1,2-a]pyridin-2-yl)-ethyl]-isoindole-1,3-dione

In a dried three-necked round bottom flask were placed Intermediate 10 (3.5 g, 14.5 mmol, 1.05 eq.), pthalimide (2.014 g, 13.69 mmol, 1.0 eq.) and PPh$_3$ (8.26 g, 31.49 mmol, 2.3 eq.) in anhydrous THF (85 mL). The mixture was cooled to 0° C. Diisopropyl azadicarboxylate (3.6 g, 17.8 mmol, 1.3 eq.) was added drop wise. The mixture was allowed to warm-up during 2 h and then taken up in DCM, washed with water and dried over magnesium sulfate. The residue was purified by chromatography over silica gel (Eluent: 99 DCM/1 methanolic ammonia) to give the title product as a yellow solid (6.87 g, 100%). $^1$H NMR (400 MHz, CDCl$_3$) δ 7.85 (m, 2H), 7.59 (d, J 1.0 Hz, 2H), 7.42 (m, 2H), 7.20 (dd, J 9.5 Hz, J 1.7 Hz, 1H), 4.13 (t, J 7.2 Hz, 2H), 3.23 (t, J 7.2 Hz, 2H). %). LCMS (ES$^+$) 370.0/372.0 (M+H)$^+$.

Intermediate 12

2-(6-bromo-imidazo[1,2-a]pyridin-2-yl)-ethylamine

To a solution of Intermediate 11 (6.87 g, 18.56 mmol, 1.0 eq.) in MeOH (30 mL) was added hydrazine (5.1 ml solution 35% in H$_2$O, 55.7 mmol, 3.0 eq.) and the mixture was heated to reflux for 4 h. The reaction mixture was taken up in EtOH (3×) and concentrated under reduced pressure. The residue was purified by reversed phase chromatography to yield the title compound (900 mg, 20%). LCMS (ES$^+$) 240.2/242.2 (M+H)$^+$.

Intermediate 13

2-amino-4-fluoro-5-bromopyridine

To a solution of 2-amino-4-fluoropyridine (75.0 g, 0.67 mol) in dry acetonitrile (700 mL), N-bromosuccinimide (122.8 g, 0.69 mol) was added portion wise upon stirring and cooling in an ice-water bath. The reaction mixture was stirred at r.t. for 1 h. After evaporation under reduced pressure, the residue was thoroughly washed with water (3×300 mL), taken up by acetonitrile and evaporated under vacuum yielding the title compound as an off white solid (124 g, 97%).

Intermediate 14

(6-bromo-7-fluoro-imidazo[1,2-a]pyridin-2-yl)-acetic acid ethyl ester

To a solution of Intermediate 13 (2.014 g, 10.54 mmol, 1.0 eq.) in EtOH (25 mL) heated at 80° C. was added 4-chloro-3-oxo-butyric acid ethyl ester (1.91 g, 11.6 mmol, 1.1 eq.) drop wise. The reaction mixture was heated for 14 h, then concentrated to dryness to give a beige solid, taken up in 2×20 mL EtOAc and filtered. The solid was again taken up in 50 mL EtOAc, washed with 50 mL of an aq. sat. sol. of NaHCO$_3$. The aqueous phase was extracted with 3×50 mL EtOAc. The organic phase was washed with brine, dried over MgSO$_4$ and concentrated to yield the title compound as a black solid (2.65 g, 83%). $^1$H NMR (400 MHz, CDCl$_3$) δ 8.26 (d, J 6.4 Hz, 1H), 7.55 (s, 1H), 7.27 (m, 1H), 4.21 (m, 2H), 3.83 (s, 2H), 1.28 (m, 3H). LCMS (ES$^+$) RT 4.3 min, 301.0/303.0 (M+H)$^+$.

Intermediate 15

2-(6-bromo-7-fluoro-imidazo[1,2-a]pyridin-2-yl)-ethanol

To a solution of Intermediate 14 (2.5 g, 8.30 mmol, 1 eq.) in EtOH (20 mL) at 2° C. was added NaBH$_4$ (0.345 g, 9.1 mmol, 1.1 eq.) portion wise. The reaction mixture was then heated at 35° C. for 2 h, then quenched at 2° C. with a 2 N aq. sol. of HCl (10 mL) and extracted with DCM. The organic phase was washed with an aq. sat. solution of NaHCO$_3$, dried over MgSO$_4$ and concentrated in vacuo to yield the title compound (1.7 g) used in the next step without any further purification. LCMS (ES$^+$) RT 2.87 min, 259.1/261.1 (M+H)$^+$.

Intermediate 16

Ethyl 6-bromo-7-fluoro-imidazo[1,2-a]pyridine-2-carboxylate

To a solution of Intermediate 13 (87.6 g, 0.459 mol) in DME (750 mL), ethyl bromopyruvate (116.3 g, 0.596 mol, 1.3 eq.) was added upon stirring. The reaction mixture was stirred at r.t. overnight. The resulting white precipitate was filtered, washed with DME (150 mL), $Et_2O$ (150 mL) and air dried at r.t. A suspension of the resulting white solid in i-PrOH (1000 mL) was stirred at 90° C. for 3 h. The solvent was distilled off under reduced pressure, the residue was stirred with a solution of $KHCO_3$ (75.0 g, 0.75 mol) in water (500 mL) at r.t. for 1 h. The precipitate was filtered, washed with water (3×500 mL), evaporated with MeCN and dried under vacuum yielding the title compound as an off white solid (108 g, 82%). $^1H$ NMR (400 MHz, DMSO-$d_6$) δ 1.32 (t, J 7.1 Hz, 3H), 4.31 (q, J 7.1 Hz, 2H), 7.75 (d, J 9.8 Hz, 1H), 8.45 (s, 1H), 9.08 (d, J 7.1 Hz, 1H). LCMS (ES$^+$) RT 1.44 min, 287.0/289.0 (M+H)$^+$.

Intermediate 17

6-bromo-7-fluoro-imidazo[1,2-a]pyridin-2-yl)methanol

At −65° C., in an Ar-atmosphere, diisobutylaluminium hydride (74 mL, 1.5 M in toluene, 110 mmol, 2.5 equiv.) was added drop wise upon stirring to a suspension of Intermediate 16 (12.65 g, 44.1 mmol, 1 eq.) in toluene (220 mL). The reaction mixture was stirred at −20° C. for 1 h, and at r.t. for 1.5 h, before addition of water (10 mL) at 0° C. The mixture was diluted with EtOAc (300 mL), filtered through celite, washed with brine (2×100 mL), dried over sodium sulfate, filtered, and concentrated under a reduced pressure. The residue was dried under vacuum, yielding the title compound (8.44 g, 78%). $^1H$ NMR (400 MHz, DMSO-d6) 9.03 (d, J 6.9 Hz, 1H), 7.73 (s, 1H), 7.54 (d, J 10.0 Hz, 1H), 5.25 (t, J 5.6 Hz, 1H), 5.55 (d, J 5.6 Hz, 2H). LCMS (ES+) RT 0.76 min, 245.0/247.0 (M+H)+.

Intermediate 18

6-bromo-2-(chloromethyl)-7-fluoroimidazo[1,2-a]pyridine

To a suspension of Intermediate 17 (8.44 g, 34.5 mmol, 1 eq) in dry dichloromethane (200 mL), thionyl chloride (20.5 g, 172 mmol, 5.0 equiv.) was added drop wise upon stirring. The resulted thick suspension was stirred at r.t. for 2 h; the solvent was evaporated under a reduced pressure. The residue was re-evaporated with toluene and distributed between $CHCl_3$ (400 mL) and 10% aq. $KHCO_3$ (200 mL); the aqueous layer was extracted with chloroform (100 mL). The combined organic layer was dried over sodium sulfate, filtered, and concentrated under a reduced pressure. The residue was dried under vacuum, yielding the title compound (9.0 g, 100%). $^1H$ NMR (400 MHz, DMSO-d6) δ 9.08 (d, J 7.1 Hz, 1H), 7.96 (s, 1H), 7.64 (d, J 9.5 Hz, 1H), 4.82 (s, 2H). LCMS (ES+) RT 0.99 min, 263.0/265.0 (M+H)+.

Intermediate 19

2-[(6-bromo-7-fluoro-imidazo[1,2-a]pyridin-2-yl)methoxy]-1-phenylethanol

To a solution of (1,2-dihydroxyethyl)benzene (JOC 2008, 73 (6), 2273) (6.18 g, 44.9 mmol, 1 eq), di-n-butyl tin oxide (11.14 g, 44.9 mmol, 1 eq) was added. The reaction mixture was refluxed in a flask equipped by a Dean-Stark trap for 2 h, cooled to RT, and concentrated under a reduced pressure. To the crude residue, dry DMF (250 mL), Intermediate 18 (9.00 g, 34.5 mmol, 0.77 equiv.), and CsF (7.80 g, 51.3 mmol, 1.14 equiv.) were added. The reaction mixture was stirred at r.t. for 18 h in an Ar-atmosphere. The reaction mixture was filtered, and concentrated under a reduced pressure. The residue was distributed between EtOAc (500 mL) and water (250 mL); the aqueous layer was extracted with EtOAc (250 mL). The combined organic layer was dried over magnesium sulfate, filtered, and concentrated under a reduced pressure. The residue was purified over silica gel (chloroform/ethyl acetate 4/1 to 2/1), yielding the title compound (5.32 g, 43%). $^1H$ NMR (400 MHz, DMSO-d6) δ 9.03 (d, J 6.9 Hz, 1H), 7.79 (s, 1H), 7.59 (d, J 9.8 Hz, 1H), 7.20-7.38 (m, 5H), 5.41 (d, J 3.9 Hz, 1H), 4.72 (m, 1H), 4.59 (s, 2H), 3.55 (m, 2H). LCMS (ES+) RT 1.23 min, 36.0/367.0 (M+H)+.

Intermediate 20

2-chloro-1-[(4R)-2,2-dimethyl-1,3-dioxolan-4-yl]ethanone

To methyl (R)-(+)-2,2-dimethyl-1,3-dioxolane-4-carboxylate (5 g, 30.5925 mmol, 1 eq) and chloroiodomethane (5.757 mL, 13.4898 g, 76.4812 mmol, 2.5 eq) in 70 ml of dry THF, cooled at −78° C., were added lithium diisopropylamide (38.2406 mL, 76.4812 mmol, 2.5 eq) over 10 minutes and kept stirring for additional 10 minutes before addition of 20 ml a solution of acetic acid in 120 ml of THF and finally 50 ml of water. The mixture was poured in a stirred biphasic solution of 600 ml of ethyl acetate and 350 ml of sodium hydroxide 1N. The pH was basified by addition of 50 ml of sodium hydroxide 1N. Aqueous layers were extracted by 600 ml of ethyl acetate. Organic layers were washed by brine, dried (MgSO$_4$), and concentrated in vacuo. The resulting brown oil was purified two successive chromatography on silica gel (DCM 100%) yielding the title compound as a pale yellow oil (1.6 g, 30%). $^1H$ NMR δ: 4.62 (dd, J 7.8 Hz, J 5.1 Hz, 1H), 4.46 (dd, J 22.0 Hz, J 17.1 Hz, 2H), 4.26 (t, J 8.9 Hz, 1H), 4.09 (dd, J 9.0 Hz, J 5.0 Hz, 1H), 1.50 (s, 3H), 1.39 (s, 3H).

Intermediate 21

(1S)-1-(6-bromo-7-fluoro-imidazo[1,2-a]pyridin-2-yl)ethane-1,2-diol

Intermediate 20 (1.6 g, 9.0 mmol, 1 eq), 5-bromo-4-fluoro-pyridin-2-amine (1.7 g, 9.0 mmol, 1 eq) and potassium iodide (0.15 g, 0.90 mmol, 0.1 eq) were solubilized in 14 ml of absolute ethanol and refluxed for 20 hours. Solvents were evaporated and the residue was purified by reverse basic phase chromatography. yielding the title compound as a white solid (380 mg, 15%). LCMS (ES+) RT 2.00 min, 275.1/277.2 (M+H)+.

Intermediate 22

2-[7-fluoro-6-(2-morpholinopyrimidin-5-yl)imidazo[1,2-a]pyridin-2-yl]ethanol

The title compound was prepared from Intermediate 15 and -morpholinopyrimidin-5-ylboronic acid by the Method C. LCMS (ES+) RT 1.62 min, 344.0 (M+H)+.

Intermediate 23

2-Bromo-8,9-dihydro-6H-cyclohepta[4,5]imidazo[1,2-a]pyridin-10(7H)-one

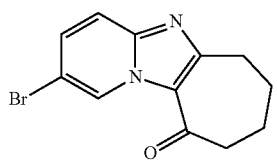 [SMILES: O=C1CCCCc2nc3ccc(Br)cn3c21]

Step 1: Preparation of 2-bromocycloheptane-1,3-dione

A solution of bromine (382 μl, 7.43 mmol, 1.05 eq.) in acetic acid (5 ml) was added over 20 min to a cooled (10° C.) mixture of 1,3-cycloheptanedione (893 mg, 7.08 mmol) and sodium acetate (639 mg, 7.79 mmol, 1.10 eq.) in AcOH (10 ml). The resulting white suspension was stirred at 10° C. for 1 h. The reaction mixture was poured into ice-water and carefully neutralised with NaHCO$_3$ (s). The aq. mixture was extracted with ether (3×), the combined organic layers were washed with sat. aqueous NaHCO$_3$ and brine, dried (Na$_2$SO$_4$) and concentrated in vacuo, yielding the title compound as a yellow oil (775 mg)

Step 2: Preparation of 2-Bromo-8,9-dihydro-6H-cyclohepta[4,5]imidazo[1,2-a]pyridin-10(7H)-one

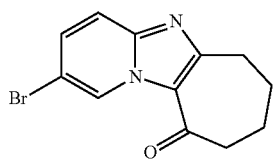 [SMILES: O=C1CCCCc2nc3ccc(Br)cn3c21]

2-bromocycloheptane-1,3-dione was combined with 2-amino-5-bromopyridine (661 mg, 3.82 mmol) in ethanol (10 mL) and heated at 100° C. for 24 h. The reaction mixture was concentrated in-vacuo, and the residue was partitioned between sat. aqueous NaHCO$_3$ soln. and EtOAc. The aqueous layer was extracted with EtOAc (2×). The combined organic layers were washed with brine, dried over Na$_2$SO$_4$ and concentrated in-vacuo. The residue was purified by column chromatography (silica gel, 75-100% EtOAc in heptane) yielding the title compound as a light brown solid (397 mg, 20%). $^1$H NMR (300 MHz, CDCl$_3$) δ 9.87 (t, J 1.4 Hz, 1H), 7.51-7.54 (m, 2H), 3.22 (dd, J 7.0, 5.5 Hz, 2H), 2.91-2.81 (m, 2H), 2.14-1.90 (m, 4H).

Intermediate 24

2-(6-Methoxypyridin-3-yl)-8,9-dihydro-6Hcyclohepta[4,5]imidazo[1,2-a]pyridin-10(7H)-one

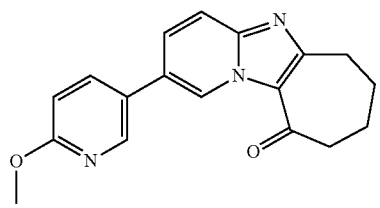 [SMILES: COc1ccc(-c2ccc3nc4c(n3c2)C(=O)CCCC4)cn1]

The title compound was prepared from Intermediate 23 (437 mg, 1.56 mmol) and 2-methoxy-5-pyridine boronic acid (287 mg, 1.88 mmol, 1.2 eq.) by the Method C (384 mg, 80%). $^1$H NMR (300 MHz, CDCl$_3$) δ 9.88 (dd, J 1.8, 1.0 Hz, 1H), 8.41 (dd, J 2.6, 0.7 Hz, 1H), 7.82 (dd, J 8.6, 2.6 Hz, 1H), 7.74-7.61 (m, 2H), 6.87 (dd, J 8.6, 0.7 Hz, 1H), 4.00 (s, 3H), 3.25 (dd, J 7.0, 5.5 Hz, 2H), 2.92-2.81 (m, 2H), 2.13-1.93 (m, 4H).

Intermediate 25

1-tert-butyl-4-ethyl 4-methylpiperidine-1,4-dicarboxylate

Ethyl N-Boc-piperidine-4-carboxylate (10.00 g, 36.92 mmol) was dissolved in THF (100 mL) and cooled to −78° C. LDA (47 mmol, 23 mL) was added and the reaction stirred for 1 h. Iodomethane (81.25 mmol, 5.08 mL) was then added and the reaction stirred for a further 1 h before removing the cold bath and allowing the reaction to warm to r.t. for 30 min. The reaction was quenched with NH$_4$Cl (sat) and partitioned with EtOAc, the organics were extracted and dried (MgSO$_4$) and concentrated in vacuo, (quantitative yield). $^1$H NMR (400 MHz, DMSO-d$_6$) δ: 4.11 (q, J 7.1 Hz, 2H), 3.61 (dt, J 13.4 Hz, J 4.5 Hz, 2H), 2.95 (d, J 0.3 Hz, 2H), 1.91 (d, J 13.6 Hz, 2H), 1.39 (s, 9H), 1.31 (m, 2H), 1.19 (m, 3H), 1.15 (s, 3H).

Intermediate 26

Ethyl 4-methylpiperidine-4-carboxylate; hydrochloride

To a solution of Intermediate 25 (11.0 g, 40.5 mmol) dissolved in 1,4-Dioxane (30.0 mL) at 0-5° C. was added HCl (15.2 mL, 4 M in 1,4-dioxane) the mixture was allowed to warm to r.t. and stirred for 18 h. The reaction mixture was concentrated in vacuo and residue washed with diethyl ether, yielding the title compound as an orange solid (5.02 g, 59.6%). $^1$H NMR (DMSO-d$_6$) δ: 9.00 (m, 1H), 4.14 (q, J 6.8 Hz, 2H), 3.16 (m, 2H), 2.82 (m, 2H), 2.08 (d, J 14.4 Hz, 2H), 1.65 (m, 2H), 1.22 (m, 6H).

Intermediate 27

[2-(4-ethoxycarbonyl-4-methyl-1-piperidyl)pyrimidin-5-yl]boronic acid

A mixture of 2-chloropyrimidine-5-boronic acid (3.95 g, 24.2 mmol), Intermediate 26 (5.03 g, 24.2 mmol) and TEA (60.6 mmol, 8.50 mL) in EtOH (50 mL) was heated at 70° C. for 5 h. The reaction was cooled and partitioned between water (100 mL) and ethyl acetate (100 mL). The aqueous layer was separated and re-extracted with further ethyl acetate (2×100 mL). The organic layers were combined and washed with brine (100 mL) before separating, drying over MgSO$_4$, filtering under reduced pressure and concentrating in vacuo, yielding the title compound as a brown foam (quantitive yield). LCMS (ES$^+$) RT 1.228 min, 294.0 (M+H)$^+$.

Intermediate 28

[2-(Morpholin-4-yl)pyrimidin-5-yl]boronic acid

A solution of (2-chloropyrimidin-5-yl)boronic acid (1 g, 6.32 mmol), morpholine (2.19 mL, 25.26 mmol) and triethylamine (0.9 mL, 6.32 mmol) in ethanol (25 mL) was stirred at 20° C. for 1 h. Water (50 mL) was slowly added to the reaction mixture to form a precipitate that was collected by filtration, to afford the title compound as a cream solid (950 mg, 70%). δH (250 MHz, DMSO-d$_6$) 8.63 (s, 2H), 8.05 (s, 2H), 3.68 (ddd, J 23.4, 5.7, 3.9 Hz, 8H). LCMS (ES$^+$) 210 (M+H)$^+$.

Intermediate 29

Enantiomer 1(1R or S)-1-[2-(difluoromethoxy)phenyl]-7-fluoro-8-{6-{(chloromethyl)methyl]pyridin-3-yl}-3,4-dihydro-1H-pyrano[4',3':4,5]imidazo[1,2-a]pyridine

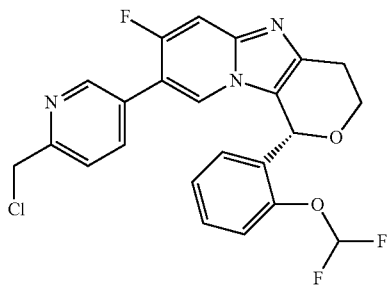 [SMILES: Fc1cc2nc3c(n2cc1-c1ccc(CCl)nc1)[C@@H](c1ccccc1OC(F)F)OCC3]

To a solution of Example 37 (60 mg, 1 eq.) in chloroform (10 mL/g), cooled at 0° C., was added drop wise thionyl chloride (5 eq.) and the mixture was heated at 60° C. for 3 h. The reaction was quenched by addition of saturated aqueous sodium bicarbonate solution and then extracted twice with DCM. The organic layer was dried (MgSO$_4$) and concentrated yielding the title compound as a brown oil (61 mg, 98% yield). LCMS (ES$^+$) RT 4.62 min, 460.2 (M+H)$^+$.

Intermediates 30 and 31

Enantiomer 1: (1S,4R or S)-6-Bromo-4-(2-difluoromethoxy-5-chloro-phenyl)-7-fluoro-1,4-dihydro-2H-3-oxa-4b,9-diaza-fluoren-1-ol; enantiomer 2 (1S,4S or R)-6-Bromo-4-(2-difluoromethoxy-5-chloro-phenyl)-7-fluoro-1,4-dihydro-2H-3-oxa-4b,9-diaza-fluoren-1-ol

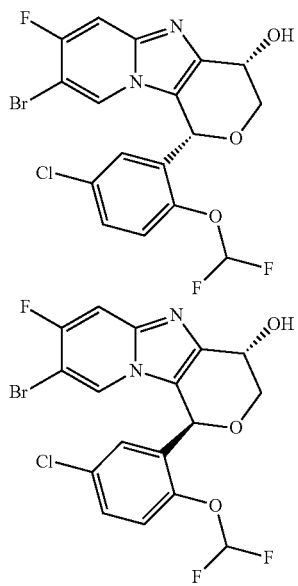

The title intermediates were prepared from Intermediate 21 and 4-chloro-1-(difluoromethoxy)-2-(dimethoxymethyl)benzene following the procedure described for Example 1 (Method B) (77 mg, 26%).

4-chloro-1-(difluoromethoxy)-2-(dimethoxymethyl)benzene was prepared from 4-chloro-1-(difluoromethoxy)-benzaldehyde following the Method A.

The title intermediates were isolated by chiral purification under SFC conditions on Chiralpak AD (50*216 mm*mm, flow 360 mL/min, 25° C., MeOH 20%, injection of 10 mL solution at a concentration of 7 g/L). The first eluting enantiomer (RT 4.87 min) was collected and the fractions were evaporated to yield Intermediate 30 (30 mg, 39%). The second eluting enantiomer (RT 7.97 min) was collected and the fractions were evaporated to yield 31 mg of Intermediate 31 (27 mg, 35%). LCMS (ES$^+$) RT 4.35 min, 463.1/465.1/467.0 (M+H)+.

Intermediate 32

(E)-Ethyl 4-[2-(difluoromethoxy)phenyl]-2-oxobut-3-enoate

A suspension of 2-(difluoromethoxy)benzaldehyde (295 g, 1714 mmol) and ethyl (triphenylphosphoranylidene)pyruvate (279.1 g, 742 mmol) was heated at 100° C. The dark red aldehyde immediately decolorized, and a yellow suspension was obtained, which slowly changed to a dark brown solution. 2-(Difluoromethoxy)benzaldehyde (52.5 g, 305 mmol) was added to the reaction mixture. Residual aldehyde was separated from the reaction mixture by distillation. The resulting mixture was stirred in heptane (500 mL) and Et$_2$O (500 mL). The brown solid precipitate was filtered off, and washed with a 1:1 mixture of heptane and Et$_2$O (3×250 mL). The filtrate was concentrated, yielding a brown oil (218.5 g).

Purification by flash column chromatography (SiO$_2$, 2-20% EtOAc in heptane) gave the title compound (91 g) as a yellow oil. 1H (CDCl$_3$, 300 MHz) 1.42 (t, J 7.1 Hz, 3H), 4.40 (q, J 7.1 Hz, 2H), 6.59 (t, J 72.9 Hz, 1H), 7.20 (dd, J 7.3, 1.0 Hz, 1H), 7.28 (br t, J 7.6 Hz, 1H), 7.38 (d, J 16.3 Hz, 1H), 7.46 (dt, J 7.8, 1.7 Hz, 1H), 7.75 (dt, J 7.8, 1.6 Hz, 1H), 8.13 (d, J 16.3 Hz, 1H). LCMS (ES$^+$) 271 (M+H)$^+$.

Intermediate 33

Ethyl 4-[2-(difluoromethoxy)phenyl]-2-[(triethylsilyl)oxy]but-2-enoate

To a nitrogen-flushed solution of Intermediate 32 (50 g, 185 mmol) in DCM (500 mL) was added rhodium(II) acetate dimer (0.818 g, 1.85 mmol) and triethylsilane (35.5 mL, 25.8 g, 222 mmol). The resulting mixture was stirred at reflux. Additional triethylsilane (10 mL, 7.28 g, 62.6 mmol) and rhodium(II) acetate dimer (0.2 g, 0.453 mmol) were added after 4 h. Heating at reflux was continued for 15 h. The reaction mixture was cooled to r.t. and filtered over a tight pad of kieselguhr. The resulting material was rinsed with DCM and concentrated in vacuo to yield the title compound (61 g) as a clear yellow oil that was employed in subsequent steps with no further purification. 4:1 mixture of E/Z-isomers. Major isomer: 1H (CDCl$_3$, 300 MHz) 7.33-7.02 (m, 4H), 6.51 (t, J 74.1 Hz, 1H), 6.11 (t, J 7.4 Hz, 1H), 4.21 (q, J 7.1 Hz, 2H), 3.57 (d, J 7.4 Hz, 2H), 1.30 (t, J 7.1 Hz, 3H), 1.07-0.91 (m, 9H), 0.83-0.64 (m, 6H). Minor isomer: 1H (CDCl$_3$, 300 MHz) δ 7.33-7.02 (m, 4H), 6.51 (t, J 74.1 Hz, 1H), 5.58 (t, J 8.0 Hz, 1H), 4.25 (q, J 7.1 Hz, 2H), 3.86 (d, J 8.0 Hz, 2H), 1.30 (t, J 7.1 Hz, 3H), 1.07-0.91 (m, 9H), 0.83-0.64 (m, 6H).

Intermediate 34

Ethyl 3-bromo-4-[2-(difluoromethoxy)phenyl]-2-oxobutanoate

To a stirred solution of Intermediate 33 (69 g, 179 mmol) in THF (700 mL) at r.t. was added N-bromosuccinimide (35.0 g, 196 mmol). The resulting mixture was stirred at reflux for 2 h before being cooled to r.t. The reaction mixture was concentrated to approximately one-third of its original volume. DCM (500 mL) was added and the resulting mixture was washed with a sat. aq. sodium bicarbonate solution (700 mL), then extracted with DCM (250 mL), dried over sodium sulfate and concentrated in vacuo, to yield a crude yellow oil (97 g). After storage overnight at r.t. under nitrogen, the product had partly solidified. The resulting material was triturated in diisopropyl ether (300 mL) for 1 h at r.t. The precipitate was removed by filtration. The filtrate was concentrated in vacuo yielding clear yellow-brown oil (88 g). Purification by flash column chromatography (SiO$_2$, 2-20% EtOAc in heptane) afforded the title compound (58.3 g) as a light brown oil. 1H (CDCl$_3$, 300 MHz) 1.38 (t, J 7.1 Hz, 3H), 3.32 (dd, J 14.5, 7.8 Hz, 1H), 3.55 (dd, J 14.5, 7.1 Hz, 1H), 4.36 (q, J 7.1 Hz, 2H), 5.37 (dd, J 7.8, 7.1 Hz, 1H), 6.58 (t, J 73.5 Hz, 1H), 7.09-7.19 (m, 2H), 7.26-7.33 (m, 2H). LCMS (ES$^+$) 271 (M+H)$^+$.

Intermediate 35

Ethyl 6-bromo-3-[[2-(difluoromethoxy)phenyl]methyl]imidazo[1,2-a]pyridine-2-carboxylate 5-Bromopyridin-2-amine (43.5 g, 251.0 mmol), Intermediate 34 (40.0 g, 140 mmol) and magnesium sulphate (50.0 g, 419.0 mmol) were suspended in 1,4-dioxane (1 L) and heated at 60° C. for 18 h. The reaction was cooled and the solids were filtered-off and washed with EtOAc. The filtrate was concentrated redissolved in EtOAc and washed with sat. sodium bicarbonate solution. The organic layer was washed with brine, dried over sodium sulfate and concentrated in vacuo to afford a brown oil. The oil was triturated with Et$_2$O for 1 h, filtered-off and dried in vacuo yielding the title compound (27.16 g, 44.9%). δH (CDCl$_3$, 300 MHz) 8.07 (dd, J 1.8, 0.9 Hz, 1H), 7.58 (dd, J 9.6, 0.9 Hz, 1H), 7.32-7.21 (m, 2H), 7.19-7.12 (m, 1H), 7.07 (td, J 7.4, 1.3 Hz, 1H), 7.00 (dd, J 7.7, 1.6 Hz, 1H), 6.66 (t, J 73.6 Hz, 1H), 4.73 (s, 2H), 4.47 (q, J 7.1 Hz, 2H), 1.44 (t, J 7.1 Hz, 3H). LCMS (ES$^+$) RT 3.10 min, 425.0/427.0 (M+H)$^+$.

Intermediate 36

Ethyl 6-bromo-3-[1-[2-(difluoromethoxy)phenyl]-3-ethoxy-3-oxo-propyl]imidazo[1,2-a]pyridine-2-carboxylate

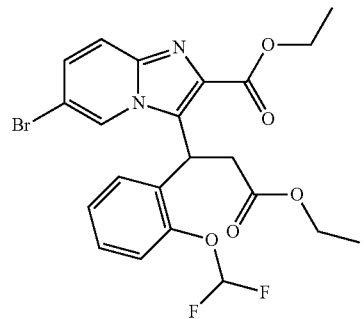 [SMILES: CCOC(=O)CC(c1ccccc1OC(F)F)c1c(C(=O)OCC)nc2ccc(Br)cn12]

Intermediate 35 (13.0 g, 30.6 mmol) was dissolved in THF (600 ml) and the mixture was cooled to −100° C. 1M KHMDS in THF (34 mL, 34.0 mmol) was added drop wise and the resulting mixture was stirred at −95° C. for 15 min. Ethyl 2-bromoacetate (7.55 g, 45.2 mmol) was added and the resulting mixture was stirred at −95° C. for 30 min. EtOAc was added and the mixture was washed with water, the organics washed with brine, dried with sodium sulfate and concentrated in vacuo to afford a yellow oil. The residue was triturated with Et$_2$O and filtered yielding the title compound as a beige solid (10.8 g, 54%). 1H (CDCl3, 300 MHz) 8.56 (s, 1H), 7.73 (dd, J 7.2, 2.2 Hz, 1H), 7.53 (dd, J 9.6, 0.8 Hz, 1H), 7.29 (dd, J 9.6, 1.8 Hz, 1H), 7.26-7.15 (m, 2H), 7.01-6.94 (m, 1H), 6.37 (t, J 73.5 Hz, 1H), 5.39 (dd, J 9.8, 5.8 Hz, 1H), 4.38 (qd, J 7.1, 0.8 Hz, 2H), 4.01 (qd, J 7.1, 3.4 Hz, 2H), 3.82 (dd, J 16.8, 9.8 Hz, 1H), 3.34 (dd, J 16.8, 5.8 Hz, 1H), 1.38 (t, J 7.1 Hz, 3H), 1.11 (t, J 7.1 Hz, 3H). LCMS (ES$^+$) RT 2.13 min, 511.0/513.0 (M+H)$^+$.

Intermediate 37

7-Bromo-1-(2-difluoromethoxy-phenyl)-3-oxo-2,3-dihydro-1H-cyclopenta[4,5]imidazo[1,2-a]pyridine-2-carboxylic acid ethyl ester

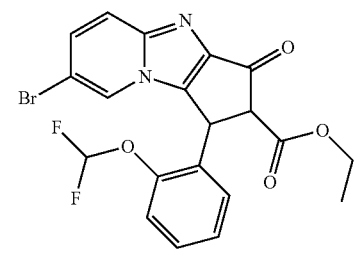 [SMILES: CCOC(=O)C1C(=O)c2nc3ccc(Br)cn3c2C1c1ccccc1OC(F)F]

Under an argon atmosphere, Intermediate 36 (4.0 g, 7.7 mmol) was dissolved in dry THF (150 mL). Potassium tert-butoxide (1.6 g, 14.26 mmol) was added and the mixture was stirred at r.t for 30 min. EtOAc was added and the reaction partitioned with water. The aq. layer was extracted with EtOAc (2×). The combined organic layers were washed with brine (×2), dried with sodium sulfate and concentrated in vacuo to yield a black oil. The residue was triturated with diisopropyl ether/DCM 7:3 and the solids were filtered off. The filtrate was concentrated in vacuo, and purified by preparative HPLC to afford the title compound as a yellow solid (792 mg, 22.7%). 15:1 mixture of diastereoisomers, major isomer: 1H (CDCl$_3$, 300 MHz) 7.76 (dd, J 1.8, 1.0 Hz, 1H), 7.63 (dd, J 9.8, 1.0 Hz, 1H), 7.43-7.33 (m, 2H), 7.30-7.22 (m, 1H), 7.16 (td, J 7.5, 1.2 Hz, 1H), 6.85-6.78 (m, 1H), 6.58 (t, J 70.0 Hz, 1H), 5.48 (d, J 2.6 Hz, 1H), 4.27 (q, J 7.1 Hz, 2H), 3.88 (d, J 2.6 Hz, 1H), 1.31 (t, J 7.1 Hz, 3H). LCMS (ES$^+$) RT 2.07 min, 465.0/467.0 (M+H)$^+$.

Intermediate 38

7-bromo-1-[2-(difluoromethoxy)phenyl]-1,2-di-hydro-3H-cyclopenta[4,5]imidazo[,2-a]pyridin-3-one

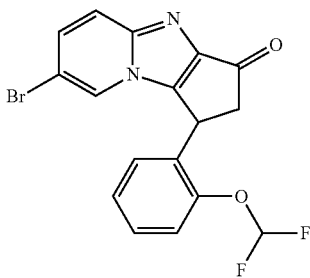 [SMILES: O=C1CC(c2ccccc2OC(F)F)c2c1nc1ccc(Br)cn21]

A solution of Intermediate 37 (10.0 g, 21.5 mmol) in DMSO (50 mL) and water (10 mL) was stirred at 100° C. for 48 h. The reaction mixture was cooled and poured onto iced water. The precipitate was then filtered off and dried in vacuo to yield the title compound as a cream solid (8.2 g, 97%). $^1$H (DMSO-d$_6$, 400 MHz) 8.27 (d, J 0.7 Hz, 1H), 7.73 (d, J 9.8 Hz, 1H), 7.55 (dd, J 9.8 Hz, 1.9 Hz, 1H), 7.40 (m, 1H), 7.26 (m, 2H), 7.17 (t, J 7.6 Hz, 1H), 6.92 (d, J 7.4 Hz, 1H), 5.14 (dd, J 7.0 Hz, 1.9 Hz, 1H), 3.60 (dd, J 18.2 Hz, 7.1 Hz, 1H), 2.75 (dd, J 18.2 Hz, 2.1 Hz, 1H). LCMS (ES$^+$) RT 1.42 min, 393.0/395.0 (M+H)$^+$.

Intermediate 39

1-(2-Difluoromethoxy-phenyl)-7-(6-methanesulfo-nyl-pyridin-3-yl)-1,2-dihydro-cyclopenta[4,5]imi-dazo[1,2-a]pyridin-3-one

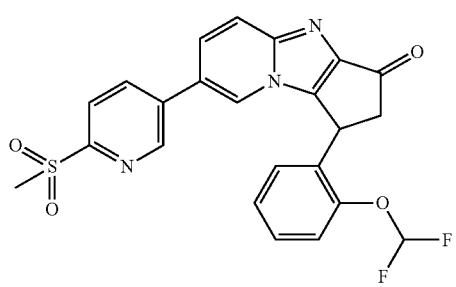 [SMILES: CS(=O)(=O)c1ccc(-c2ccc3nc4c(n3c2)C(c2ccccc2OC(F)F)CC4=O)cn1]

The title compound was prepared from Intermediate 38 and (6-methylsulfonyl-3-pyridyl)boronic acid by the Method C.
LCMS (ES$^+$) RT 1.15 min 470.0 (M+H)$^+$.

Example 1 (Method B)

8-chloro-1-[2-(difluoromethoxy)phenyl]-3,4-di-hydro-1H-pyrano[4',3':4,5]imidazo[1,2-a]pyridine

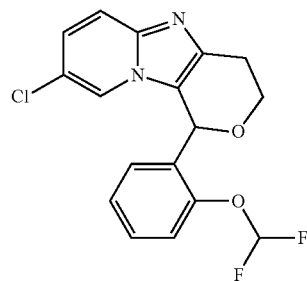 [SMILES: FC(F)Oc1ccccc1C1OCCc2nc3ccc(Cl)cn3c21]

To a solution of Intermediate 2 (1.20 g, 4.98 mmol) in acetonitrile (24 mL), para-toluenesulfonic acid (0.08 g, 0.49 mmol) and Intermediate 3 (2.17 g, 9.96 mmol) were added and the reaction mixture was heated to 90° C. for 4 h. The reaction mixture was cooled and treated with NaHCO$_3$ sat. solution (50 mL), extracted with DCM (50 mL), the organics were washed with brine (50 mL) and dried over MgSO$_4$ and concentrated in vacuo. The residue was purified by column chromatography (SiO$_2$, 100 DCM to 97 DCM/3 methanolic ammonia), yielding the title compound as a brown solid (1.30 g, 66%). $^1$H NMR (400 MHz, CDCl$_3$) δ 7.56 (d, J 9.6 Hz, 1H), 7.44 (m, 3H), 7.31 (m, 2H), 7.26 (d, J 1.1 Hz, 1H), 7.12 (dd, J 9.6, 2.0 Hz, 1H), 5.91 (s, 1H), 4.25 (m, 1H), 4.03 (m, 1H), 3.20 (m, 1H), 3.03 (m, 1H). LCMS (ES$^+$) 351.0/353.0 (M+H)$^+$.

Example 2

8-Chloro-1-(2-difluoromethoxy-phenyl)-1,2,3,4-tetrahydro-dipyrido[1,2-a; 4',3'-d]imidazole

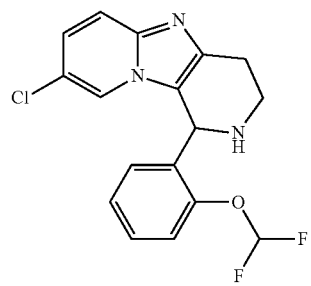 [SMILES: FC(F)Oc1ccccc1C1NCCc2nc3ccc(Cl)cn3c21]

The title compound was prepared from Intermediate 6 (0.51 g, 2.60 mmol), para-toluenesulfonic acid (0.04 g, 0.26 mmol) and 2-(difluoromethoxy)benzaldehyde (0.26 mL, 2.60 mmol) by the Method B (0.02 g, 10%). $^1$H NMR (400 MHz, CDCl$_3$) δ 7.56 (d, J 9.6 Hz, 1H), 7.40 (m, 2H), 7.32 (m, 1H), 7.12 (m, 2H), 6.79 (m, 2H), 5.70 (s, 1H), 3.18 (m, 2H), 3.01 (t, J 5.5 Hz, 2H). LCMS (ES$^+$) 350.0/352.0 (M+H)$^+$.

Example 3

8-bromo-1-[2-(difluoromethoxy)phenyl]-3,4-di-hydro-1H-pyrano[4',3':4,5]imidazo[1,2-a]pyridine

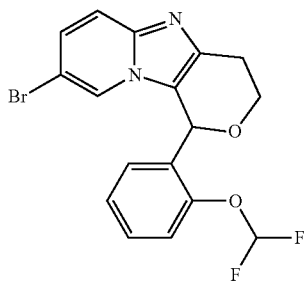

The title compound was prepared from Intermediate 10, (900 mg, 1 eq.) and Intermediate 3 (1 eq.) by the Method B, yielding the title compound as a yellow oil (976 mg, 67%). LCMS (ES+) RT 4.98 min, 395.0/397.0 (M+H)+.

Example 4

8-bromo-1-(2-difluoromethoxy-phenyl)-1,2,3,4-tetrahydro-dipyrido[1,2-a; 4',3'-d]imidazole

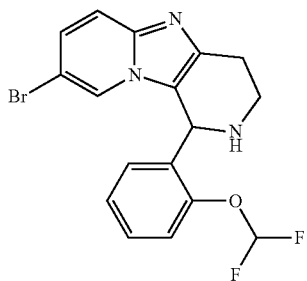

The title compound was prepared from Intermediate 12 (900 mg, 3.75 mmol, 1.0 eq.), p-toluene sulfonic acid (65 mg, 0.375 mmol, 0.1 eq.) and 2-difluoromethoxy-benzaldehyde (0.398 g, 3.748 mmol, 1 eq.) by the Method B (0.69 mg, 47%). LCMS (ES+) RT 3.9 min, 394.0/396.0 (M+H)+.

Example 5

7-bromo-4-[2-(difluoromethoxy)phenyl]-8-fluoro-3,4-dihydro-1H-[1,4]oxazino[4,3-a]benzimidazole

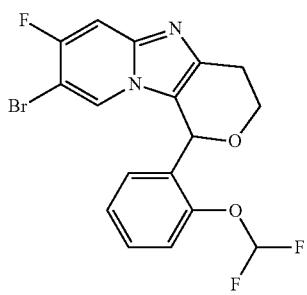 [SMILES: Fc1cc2nc3c(n2cc1Br)C(c1ccccc1OC(F)F)OCC3]

The title compound was prepared from Intermediate 15 (1.74 g, 6.77 mmol, 1.0 eq.) and Intermediate 3 (2.21 g, 10.15 mmol, 1.5 eq.) by the Method B, to yield the title compound (32%). LCMS (ES+) RT 4.3 min, 413.0/415.0 (M+H)+.

Example 6 and 7

Enantiomer 1: (4S or R)-7-bromo-4-[2-(difluoromethoxy)phenyl]-8-fluoro-3,4-dihydro-1H-[1,4]oxazino[4,3-a]benzimidazole; enantiomer 2 (4R or S)-7-bromo-4-[(difluoromethoxy)phenyl]-8-fluoro-3,4-dihydro-1H-[1,4]oxazino[4,3-a]benzimidazole

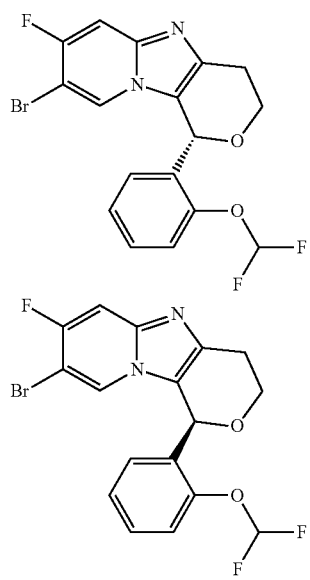

The title compounds were isolated by chiral purification of Example 5 under SFC conditions on Chiralpak AD (50*216 mm*mm, flow 360 mL/min, 25° C., CO₂+35% i-PrOH, injection of 10 mL solution at a concentration of 40 g/L). The first eluting enantiomer (RT 1.7 min) was collected and the fractions were evaporated to yield Example 6. $^1$H NMR (400 MHz, CDCl$_3$) δ 7.45 (m, 1H), 7.39 (d, J 6.3 Hz, 1H), 7.33 (d, J 8.9 Hz, 2H), 7.19 (m, 1H), 6.96 (m, 1H), 6.68 (dd, J 76.4 Hz, J 71.6 Hz, 1H), 6.32 (s, 1H), 4.16 (m, 1H), 4.00 (m, 1H), 3.13 (m, 1H), 3.00 (m, 1H). LCMS (ES+) RT 4.09 min, 413.0/415.0 (M+H)+. The second eluting enantiomer (RT 3.5 min) was collected and the fractions were evaporated to yield Example 7. $^1$H NMR (400 MHz, CDCl$_3$) δ: 7.45 (m, 1H), 7.39 (d, J 6.3 Hz, 1H), 7.33 (d, J 8.9 Hz, 2H), 7.19 (m, 1H), 6.96 (m, 1H), 6.68 (m, 1H), 6.32 (s, 1H), 4.16 (m, 1H), 4.00 (m, 1H), 3.13 (m, 1H), 3.00 (m, 1H). LCMS (ES+) RT 4.09 min, 413.0/415.0 (M+H)+.

Example 8

7-bromo-8-fluoro-4-phenyl-3,4-dihydro-1H-pyrano[3',4':4,5]imidazo[1,2-a]pyridine

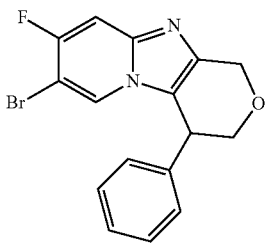 [SMILES: Fc1cc2nc3c(n2cc1Br)C(c1ccccc1)COC3]

To a solution of Intermediate 19 (4.97 g, 13.50 mmol, 1 eq) and TEA (1.79 g, 17.6 mmol, 1.3 equiv.) in dry dichloromethane (60 mL), in an Ar-atmosphere, trifluoromethanesulfonic anhydride (4.99 g, 17.6 mmol, 1.3 equiv.) was quickly added upon vigorous stirring and cooling to −45° C. (internal thermometer). The reaction mixture was spontaneously warmed up to 0° C. during 1 h, then additional amounts of TEA (1.79 g, 17.6 mmol, 1.3 equiv.) and trifluoromethanesulfonic anhydride (4.99 g, 17.6 mmol, 1.3 equiv.) were added. The reaction mixture was stirred at 0° C. for 30 min and quenched by adding 10% aq. NaHCO3 (60 mL) and chloroform (60 mL). The organic layer was separated, dried over magnesium sulfate, and filtered through a short pad of silica gel (followed by washing with chloroform/ethyl acetate 1:1) to remove a large amount of tarring products. The resulted solution was concentrated in-vacuo, and the residue was purified over silica gel (tetra chloromethane/ethyl acetate 2:1 to 1:1), yielding to the title compound (186 mg, 4%). $^1$H NMR (400 MHz, DMSO-d6) δ 8.08 (d, J 6.8 Hz, 1H). 7.70 (d, J 9.8 Hz, 1H), 7.25-7.36 (m, 3H), 7.17 (m, 2H), 4.89 (d, J 14.7 Hz, 1H), 4.8 (d, J 14.7 Hz, 1H), 4.52 (m, 1H), 4.18 (dd, J 11.3 Hz, J 2.4 Hz, 1H), 3.89 (dd, J 11.3 Hz, J 3.9 Hz, 1H). LCMS (ES$^+$) RT 1.38 min, 347.0, 349.0 (M+H)$^+$.

Examples 9 and 10

Enantiomer 1: (1R or S)-7-bromo-8-fluoro-4-phenyl-3,4-dihydro-1H-pyrano[3',4':4,5]imidazo[1,2-a]pyridine; enantiomer 2 (1S or R)-7-bromo-8-fluoro-4-phenyl-3,4-dihydro-1H-pyrano[3',4':4,5]imidazo[1,2-a]pyridine

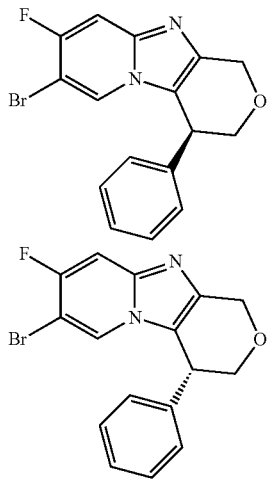

The title compounds were isolated by chiral purification of Example 8 under LC conditions on Chiralpak AD (80*475 mm*mm, flow 200 mL/min, 30° C., MeOH 100%, injection of 20 mL solution at a concentration of 10 g/L). The first eluting enantiomer (RT 25 min) was collected and the fractions were evaporated to yield Example 9. The second eluting enantiomer (RT 34 min) was collected and the fractions were evaporated to yield Example 10.

Examples 11 and 12

Enantiomer 1: (1S,4S or R)-6-Bromo-4-(2-difluoromethoxy-phenyl)-7-fluoro-1,4-dihydro-2H-3-oxa-4b,9-diaza-fluoren-1-ol; enantiomer 2 (1S,4R or S)-6-Bromo-4-(2-difluoromethoxy-phenyl)-7-fluoro-1,4-dihydro-2H-3-oxa-4b,9-diaza-fluoren-1-ol

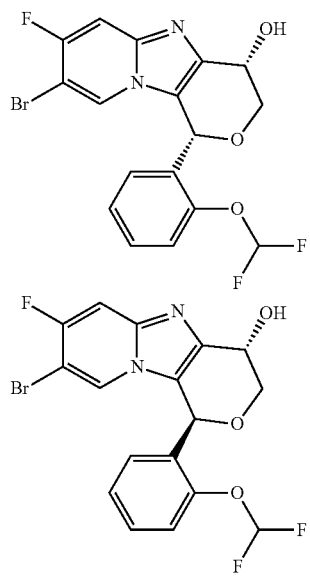

Intermediate 21 (0.15 g, 0.56 mmol, 1 eq) was suspended in acetonitrile, Intermediate 3 (0.37 g, 1.69 mmol, 3 eq) was added and finally magnesium chloride (0.11 g, 1.12 mmol, 2 eq) was added in one portion. The mixture was heated at 75° C. (in a pre-heated oil bath) for 2 h. The slurry become yellow clear liquid after 15 minutes and slowly turned to red solution. The reaction was concentrated in vacuo and the crude was taken up in ethyl acetate/water (10 mL/10 mL). Organic layer was washed by water until neutral pH (3×10 mL). Aqueous layer was basified by addition of NaOH (0.1 M) and extracted by ethyl acetate (2×10 mL). Combined organic layers were washed by NaOH (0.1 M, 3×5 ml). NaOH phases were extracted by ethyl acetate (3×10 ml). Combined organic layers were dried over sodium sulfate and ethyl acetate was evaporated. The crude was purified by reverse acid phase chromatography. The title compounds were isolated by chiral purification of 6-Bromo-4-(2-difluoromethoxy-phenyl)-7-fluoro-1,4-dihydro-2H-3-oxa-4b,9-diaza-fluoren-1-ol under SFC conditions on Chiralpak AD (50*213 mm*mm, flow 360 mL/min, 25° C., EtOH 20%, injection of 10 mL solution at a concentration of 11.3 g/L). The first eluting enantiomer (RT 2.8 min) was collected and the fractions were evaporated to yield Example 11 (40 mg, 16%). The second eluting enantiomer (RT 8 min) was collected and the fractions were evaporated to yield 31 mg of Example 12 ((31 mg, 13%). $^1$H NMR (400 MHz, CDCl$_3$) δ 7.42 (m, 4H), 7.19 (m, 1H), 6.82 (d, J 6.5 Hz, 1H), 6.69 (dd, J 76.3 Hz, J 71.7 Hz), 6.40 (bs, 1H), 5.55 (m, 1H), 5.12 (m, 1H), 3.94 (d, J 7.7 Hz, 1H). LCMS (ES$^+$) RT 3.99 min, 429.2/431.2 (M+H)$^+$.

Example 13

1-[2-(difluoromethoxy)phenyl]-8-(6-methoxypyridin-3-yl)-3,4-dihydro-1H-pyrano[4',3':4,5]imidazo[1,2-a]pyridine

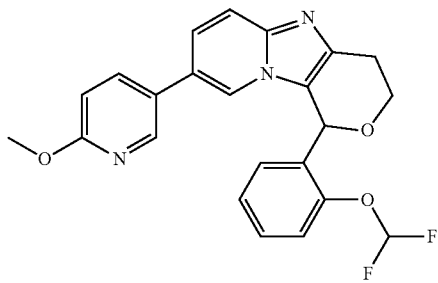 [SMILES: COc1ccc(-c2ccc3nc4c(n3c2)C(c2ccccc2OC(F)F)OCC4)cn1]

To Example 1 (0.20 g, 0.51 mmol) and 6-methoxy pyridine 3-yl boronic acid (0.09 g, 0.61 mmol) in 1,4-dioxane/water (6 mL, 10:1) was added potassium carbonate (0.21 g, 1.52 mmol). The reaction mixture was degassed for 10 minutes and Pd(PPh$_3$)$_4$ (0.06 g, 0.05 mmol) was added. The reaction mixture was heated at 100° C. for 12 h. The reaction mixture was diluted with EtOAc (10 mL), washed with water (10 mL), brine (10 mL) and the organic layer was separated, dried (Na$_2$SO$_4$) and concentrated in vacuo. The residue was purified by prep-HPLC yielding the title compound as a brown solid (0.08 g, 37%). $^1$H NMR (400 MHz, DMSO-d$_6$) δ 8.23 (d, J 2.3 Hz, 1H), 7.80 (dd, J 8.6, 2.6 Hz, 1H), 7.67 (m, 2H), 7.50 (m, 2H), 7.34 (d, J 8.1 Hz, 1H), 7.16 (m, 2H), 6.84 (m, 2H), 6.45 (s, 1H), 3.94 (t, J 5.4 Hz, 2H), 3.85 (s, 3H), 2.94 (s, 2H). LCMS (ES$^1$) RT 1.62 min, 424.0 (M+H)$^+$.

Example 14

1-[2-(difluoromethoxy)phenyl]-8-[2-(morpholin-4-yl)pyrimidin-5-yl]-3,4-dihydro-1H-pyrano[4',3':4,5]imidazo[1,2-a]pyridine

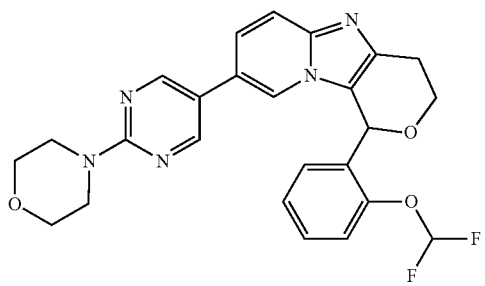 [SMILES: FC(F)Oc1ccccc1C1OCCc2nc3ccc(-c4cnc(N5CCOCC5)nc4)cn3c21]

The title compound was prepared from Example 1 and 2-morpholinopyrimidin-5-ylboronic acid by the Method C. $^1$H NMR (400 MHz, CDCl$_3$) δ 8.18 (s, 2H), 7.68 (d, J 9.2 Hz, 1H), 7.35 (m, 1H), 7.22 (m, 4H), 7.09 (t, J 7.5 Hz, 1H), 6.93 (m, 1H), 6.60 (t, J 74.0, 71.7 Hz, 1H), 6.32 (s, 1H), 4.13 (m, 1H), 3.96 (m, 1H), 3.68 (m, 8H), 3.13 (m, 1H). LCMS (ES$^+$) RT 1.45 min, 480.0 (M+H)$^+$.

Example 15

1-[2-(difluoromethoxy)phenyl]-8-[2-(morpholin-4-yl)pyrimidin-5-yl]-1,2,3,4-tetrahydroimidazo[1,2-a:5,4-c]dipyridine

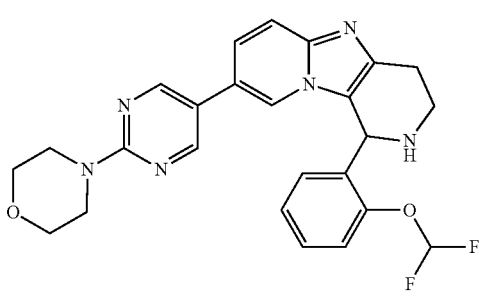 [SMILES: FC(F)Oc1ccccc1C1NCCc2nc3ccc(-c4cnc(N5CCOCC5)nc4)cn3c21]

To a solution of Example 2 (0.05 g, 0.14 mmol) in n-butanol (2 mL), 2-morpholinopyrimidin-5-ylboronic acid (0.06 g, 0.21 mmol), tris(dibenzylideneacetone)dipalladium (0)-chloroform (0.001 g, 0.0014 mmol), K$_3$PO$_4$ (0.06 g, 0.29 mmol) and dicyclohexyl-[2-(2,4,6-triisopropylphenyl)phenyl]phosphane (0.002 g, 0.006 mmol) were added, the reaction was degassed 3 times and placed under argon. The reaction mixture was heated to 100° C. for 4 h. The reaction mixture was cooled and treated with NaHCO$_3$ sat. solution (10 mL), extracted with DCM (10 mL), the organics were washed with brine (10 mL) and dried over MgSO$_4$ and concentrated in vacuo. The residue was purified by prep HPLC, yielding the title compound (0.008 g, 12%). LCMS (ES$^+$) RT 1.33 min, 479.0 (M+H)$^+$.

Example 16

1-[2-(difluoromethoxy)phenyl]-8-(6-methoxypyridin-3-yl)-1,2,3,4-tetrahydroimidazo[1,2-a:5,4-c']dipyridine

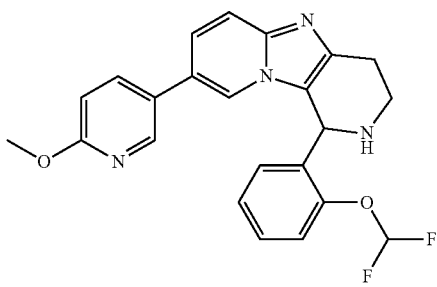 [SMILES: COc1ccc(-c2ccc3nc4c(n3c2)C(c2ccccc2OC(F)F)NCC4)cn1]

To a solution of Intermediate 8 (0.20 g, 0.74 mmol) in toluene (3 mL), para-toluenesulfonic acid (0.014 g, 0.08 mmol) and 2-(difluoromethoxy)benzaldehyde (0.133 g, 0.74 mmol) The reaction mixture was heated to 100° C. for 4 h. The reaction mixture was cooled and treated with NaHCO$_3$ sat. solution (10 mL), extracted with DCM (10 mL), the organics were washed with brine (10 mL) and dried over MgSO₄ and concentrated in vacuo. The residue was purified by column chromatography (SiO₂, 100 DCM to 90 DCM/10 methanolic ammonia), yielding the title compound (0.06 g, 20%). ¹H NMR (400 MHz, CDCl₃) δ 7.99 (d, J 2.2 Hz, 1H), 7.57 (d, J 9.2 Hz, 1H), 7.43 (dd, J 8.6, 2.4 Hz, 1H), 7.28 (m, 1H), 7.21 (m, 1H), 7.00 (t, J 74 Hz, 1H), 6.70 (m, 3H), 5.66 (s, 1H), 3.84 (s, 3H), 3.63 (q, J 7.0 Hz, 1H), 3.11 (m, 2H), 2.93 (t, J 5.3 Hz, 2H), 1.15 (t, J 7.0 Hz, 2H). LCMS (ES⁺) RT 1.38 min, 423.0 (M+H)⁺.

Example 17

8-(6-methoxypyridin-3-yl)-1-phenyl-1,2,3,4-tetrahydroimidazo[1,2-a:5,4-c']dipyridine

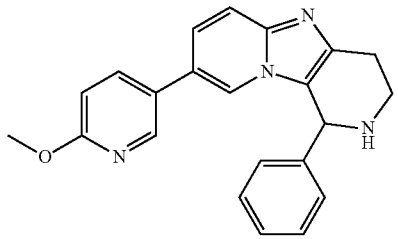 [SMILES: COc1ccc(-c2ccc3nc4c(n3c2)C(c2ccccc2)NCC4)cn1]

The title compound was prepared from Intermediate 8 (0.20 g, 0.74 mmol), para-toluenesulfonic acid (0.014 g, 0.08 mmol) and benzaldehyde (0.08 g, 0.74 mmol) by the Method B (0.05 g, 20%). LCMS (ES⁺) RT 1.33 min, 357.0 (M+H)⁺.

Example 18

8-bromo-1-[2-(difluoromethoxy)phenyl]-3,4-dihydro-1H-pyrano[4',3':4,5]imidazo[1,2-a]pyridine

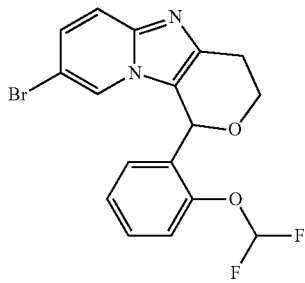

The title compound was prepared from Intermediate 10 (1.20 g, 4.98 mmol) and Intermediate 3 (2.17 g, 9.96 mmol) by the Method B (1.30 g, 66%). ¹H NMR (400 MHz, DMSO-d₆) δ 7.49 (d, J 1.0 Hz, 1H), 7.34 (d, J 9.5 Hz, 1H), 7.26 (m, 2H), 7.09 (m, 2H), 6.94 (t, J 7.5 Hz, 1H), 6.54 (dd, J 7.5, 1.2 Hz, 1H), 6.15 (s, 1H), 3.67 (td, J 5.3, 1.5 Hz, 2H), 2.68 (t, J 5.3 Hz, 2H). LCMS (ES⁺) RT 1.46 min, 395.0/397.0 (M+H)⁺.

Examples 19 and 20

Enantiomer 1: (1S or R)-8-bromo-1-[2-(difluoromethoxy)phenyl]-1,2,3,4-tetrahydroimidazo[1,2-a:5,4-c]dipyridine; enantiomer 2 (1R or S)-8-bromo-1-[2-(difluoromethoxy)phenyl]-1,2,3,4-tetrahydroimidazo[1,2-a:5,4-c]dipyridine

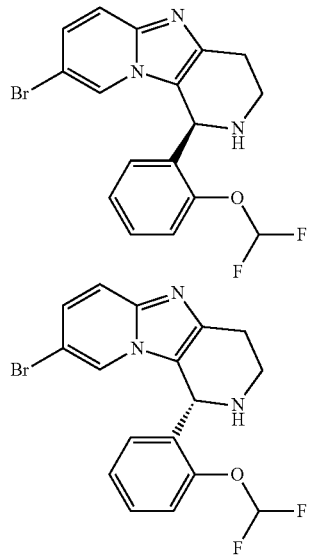

The title compounds were isolated by chiral chromatography of Example 4 under SFC conditions on Chiralcel OD (50*266 mm*mm, flow 360 mL/min, 25° C., CO₂+20% i-PrOH, injection of 10.6 mL solution at a concentration of 50 g/L). The first eluting enantiomer (RT 4.6 min) was collected and the fractions were evaporated to yield Example 19. ¹H NMR (400 MHz, CDCl₃) δ 7.52 (m, 1H), 7.41 (m, 2H), 7.32 (m, 1H), 7.22 (dd, J 9.4 Hz, J 1.6 Hz, 1H), 7.13 (td, J 7.7 Hz, J 0.4 Hz, 1H), 6.80 (m, 2H), 5.71 (s, 1H), 3.18 (m, 2H), 3.02 (m, 2H). LCMS (ES⁺) RT 2.89 min, 394.2/396.2 (M+H)⁺. The second eluting enantiomer (RT 6.2 min) was collected and the fractions were evaporated to yield Example 20. ¹H NMR (400 MHz, CDCl₃) δ 7.52 (d, J 9.6 Hz, 1H), 7.40 (m, 2H), 7.32 (m, 1H), 7.22 (dd, J 9.6 Hz, J 1.7 Hz, 1H), 7.13 (m, 1H), 6.80 (m, 2H), 5.71 (s, 1H), 3.18 (m, 2H), 3.02 (m, 2H). LCMS (ES⁺) RT 2.89 min, 394.1/395.9 (M+H)⁺.

Example 21

Enantiomer 2 (1R or S)-1-[2-(difluoromethoxy)phenyl]-8-[4-(methylsulfonyl)phenyl]-1,2,3,4-tetrahydroimidazo[1,2-a:5,4-c]dipyridine

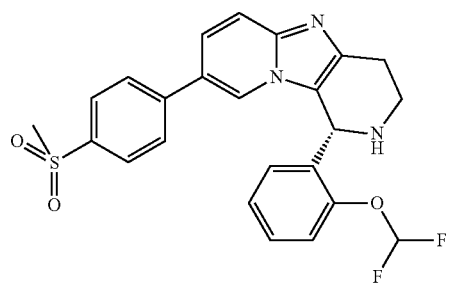 [SMILES: CS(=O)(=O)c1ccc(-c2ccc3nc4c(n3c2)[C@@H](c2ccccc2OC(F)F)NCC4)cc1]

The title compound was prepared from Example 20 (1.0 eq.) and 4,4,5,5-tetramethyl-2-(4-methylsulfonylphenyl)-1,3,2-dioxaborolane (1.2 eq.) by the Method C, yielding the title compound as a beige oil (14 mg, 16%). $^1$H NMR (400 MHz, CDCl$_3$) δ 7.94 (m, 2H), 7.70 (d, J 9.2 Hz, 1H), 7.47 (m, 3H), 7.38 (m, 2H), 7.31 (m, 1H), 7.12 (m, 1H), 6.78 (m, 2H), 5.77 (s, 1H), 3.21 (m, 2H), 3.05 (m, 5H). LCMS (ES$^+$) RT 2.8 min, 470 (M+H)$^+$.

Example 22

Enantiomer 1(1S or R)-1-[2-(difluoromethoxy)phenyl]-8-[4-(methylsulfonyl)phenyl]-1,2,3,4-tetrahydroimidazo[1,2-a:5,4-c]dipyridine

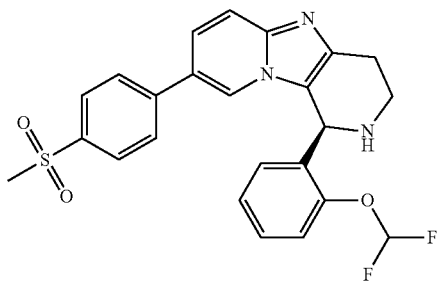 [SMILES: CS(=O)(=O)c1ccc(-c2ccc3nc4c(n3c2)[C@H](c2ccccc2OC(F)F)NCC4)cc1]

The title compound was prepared from Example 19 (1.0 eq.), and 4,4,5,5-tetramethyl-2-(4-methylsulfonylphenyl)-1,3,2-dioxaborolane (1.2 eq.) by the Method C, yielding the title compound as a white powder (32 mg, 34%). $^1$H NMR (400 MHz, CDCl$_3$) δ 7.97 (d, J 8.4 Hz, 2H), 7.72 (m, 1H), 7.50 (m, 3H), 7.40 (m, 2H), 7.34 (m, 1H), 7.14 (m, 1H), 6.80 (m, 2H), 5.80 (s, 1H), 3.25 (m, 2H), 3.07 (m, 5H). LCMS (ES) RT 2.7 min, 470.1 (M+H)$^+$.

Example 23

4-{5-[(R)-4-(2-difluoromethoxy-phenyl)-7-fluoro-1,4-dihydro-2H-3-oxa-4b,9-diaza-fluoren-6-yl]-pyridin-2-yl}-piperazine-1-carboxylic acid tert-butyl ester

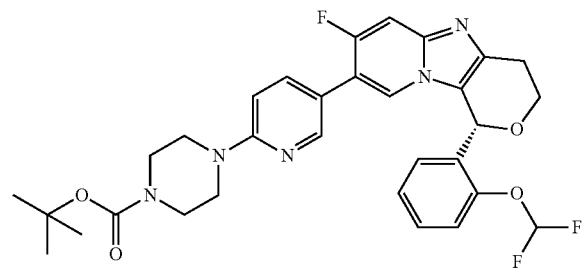 [SMILES: CC(C)(C)OC(=O)N1CCN(c2ccc(-c3cn4c5c(nc4cc3F)CCO[C@@H]5c3ccccc3OC(F)F)cn2)CC1]

The title compound was prepared from Example 6 (1.0 eq) and tert-butyl 4-[5-(4,4,5,5-tetramethyl-1,3,2-dioxaborolan-2-yl)-2-pyridyl]piperazine-1-carboxylate (1.2 eq.) by the Method C (heating at 100° C. during 20 h) yielding the title compound (450 mg, 100%). LCMS (ES$^+$) RT 5.08 min, 596.4 (M+H)$^+$.

Example 24 (Method D)

(1R)-1-[2-(difluoromethoxy)phenyl]-7-fluoro-8-[6-(piperazin-1-yl)pyridin-3-yl]-3,4-dihydro-1H-pyrano[4',3':4,5]imidazo[1,2-a]pyridine

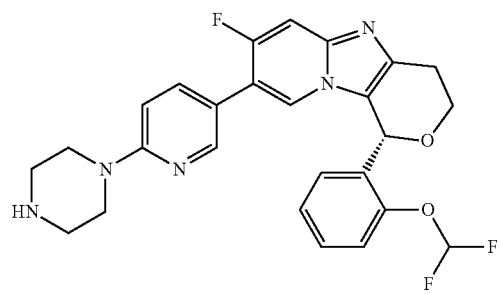 [SMILES: Fc1cc2nc3c(n2cc1-c1ccc(N2CCNCC2)nc1)[C@@H](c1ccccc1OC(F)F)OCC3]

Example 23 (0.4 g, 0.7 mmol 1 eq.) was dissolved in DCM (4 mL/mmol) and trifluoroacetic acid (4 mL/mmol). The mixture was stirred 2 h at r.t. EtOAc (100 mL) and water (50 mL) was added. The organic layer was discarded. The aqueous layer was basified by Na$_2$CO$_3$ and extracted with DCM (2×100 mL). The organic layer was separated, dried over MgSO$_4$ and concentrated in vacuo. The residue was purified by prep-HPLC yielding the title compound (0.093 g, 27%). $^1$H NMR (400 MHz, CDCl$_3$) δ 8.01 (s, 1H), 7.43 (m, 2H), 7.31 (m, 2H), 7.16 (m, 2H), 6.99 (m, 1H), 6.66 (m, 2H), 6.36 (s, 1H), 4.17 (m, 1H), 4.01 (m, 1H), 3.54 (m, 4H), 3.15 (m, 1H), 3.00 (m, 5H). LCMS (ES$^+$) RT 2.7 min, 496.2 (M+H)$^+$.

Example 25

4-{5-[(S)-4-(2-difluoromethoxy-phenyl)-7-fluoro-1,4-dihydro-2H-3-oxa-4b,9-diaza-fluoren-6-yl]-pyridin-2-yl}-piperazine-1-carboxylic acid tert-butyl ester

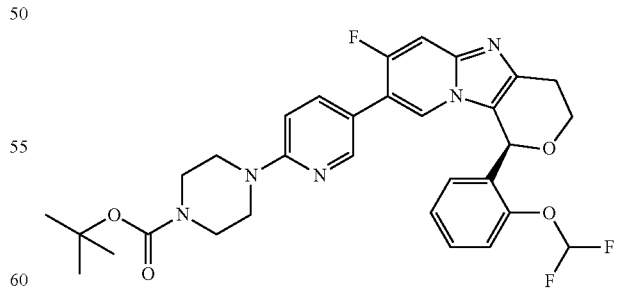

The title compound was prepared from Example 7 (0.165 g, 0.4 mmol, 1.0 eq.), and tert-butyl 4-[5-(4,4,5,5-tetramethyl-1,3,2-dioxaborolan-2-yl)-2-pyridyl]piperazine-1-carboxylate (0.194 g, 0.5 mmol, 1.25 eq.) by the Method C. LCMS (ES$^+$) RT 5.08 min, 596.4 (M+H)$^+$.

Example 26

(1R)-1-[2-(difluoromethoxy)phenyl]-7-fluoro-8-[6-(piperazin-1-yl)pyridin-3-yl]-3,4-dihydro-1H-pyrano[4',3':4,5]imidazo[1,2-a]pyridine

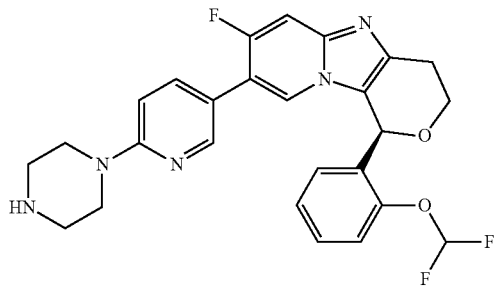 [SMILES: Fc1cc2nc3c(n2cc1-c1ccc(N2CCNCC2)nc1)[C@H](c1ccccc1OC(F)F)OCC3]

The title compound was prepared from Example 25 (238 mg, 0.4 mmol) and DCM (10 mL), TFA (10 mL) by the Method D (80 mg). $^1$H NMR (400 MHz, CDCl$_3$) δ 6.10 (m, 1H), 5.65 (m, 2H), 5.56 (m, 2H), 5.43 (m, 2H), 5.29 (m, 1H), 5.04 (m, 2H), 4.80 (m, 1H), 3.09 (m, 1H), 2.96 (m, 1H), 2.60 (m, 4H), 2.32 (m, 1H), 2.18 (m, 5H). LCMS (ES$^+$) RT 2.65 min, 496 (M+H)$^+$.

Examples 27-51

The following Examples were prepared using Method C from the assigned precursor using the appropriate boronic acid or boronate ester, either available commercially or prepared as set out in the intermediates above.

| Example No. | Precursor | Compound Name | LCMS |
|---|---|---|---|
| 27 | Ex 6 | Enantiomer 1(1R or S)-1-[2-(difluoromethoxy)phenyl]-7-fluoro-8-[4-(methylsulfonyl)phenyl]-3,4-dihydro-1H-pyrano[4',3':4,5]imidazo[1,2-a]pyridine 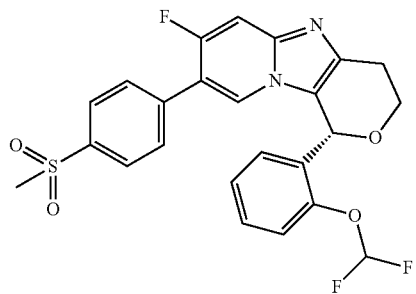 | LCMS (ES$^+$) RT 3.61 min, 489.2 (M + H)$^+$. |
| 28 | Ex 6 | Enantiomer 1(1R or S)-8-(6-cyclopropylpyridin-3-yl)-1-[2-(difluoromethoxy)phenyl]-7-fluoro-3,4-dihydro-1H-pyrano[4',3':4,5]imidazo[1,2-a]pyridine 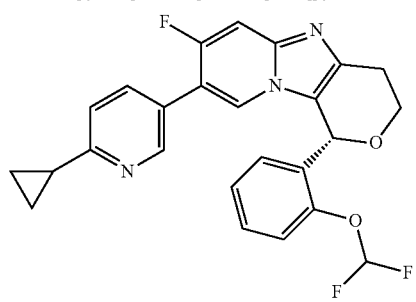 | LCMS (ES$^+$) RT 4.7 min, 452.2 (M + H)$^+$. |

-continued

| Example No. | Precursor | Compound Name | LCMS |
|---|---|---|---|
| 29 | Ex 6 | Enantiomer 1(1R or S)-1-[2-(difluoromethoxy)phenyl]-7-fluoro-8-[6-(methylsulfonyl)pyridin-3-yl]-3,4-dihydro-1H-pyrano[4',3':4,5]imidazo[1,2-a]pyridine | LCMS (ES+) RT 4.1 min, 490 (M + H)+. |
| 30 | Ex 6 | Enantiomer 1(1R or S)-8-(1-cyclopropyl-1H-pyrazol-4-yl)-1-[2-(difluoromethoxy)phenyl]-7-fluoro-3,4-dihydro-1H-pyrano[4',3':4,5]imidazo[1,2-a]pyridine | LCMS (ES+) RT 4.3 min, 441.3 (M + H)+. |
| 31 | Ex 6 | Enantiomer 1(1R or S)-1-[2-(difluoromethoxy)phenyl]-7-fluoro-8-[1-(phenylsulfonyl)-1H-pyrazol-4-yl]-3,4-dihydro-1H-pyrano[4',3':4,5]imidazo[1,2-a]pyridine | LCMS (ES+) RT 4.9 min, 541.2 (M + H)+. |

-continued

| Example No. | Precursor | Compound Name | LCMS |
|---|---|---|---|
| 32 | Ex 6 | N-(4-{Enantiomer 1(1R or S)-1-[2-(difluoromethoxy)phenyl]-7-fluoro-3,4-dihydro-1H-pyrano[4',3':4,5]imidazo[1,2-a]pyridin-8-yl}benzyl)acetamide | LCMS (ES+) RT 4.1 min, 482.3 (M + H)+. |
| 33 | Ex 6 | tert-butyl 5-{Enantiomer 1(1R or S)-1-[2-(difluoromethoxy)phenyl]-7-fluoro-3,4-dihydro-1H-pyrano[4',3':4,5]imidazo[1,2-a]pyridin-8-yl}-1,3-dihydro-2H-isoindole-2-carboxylate | LCMS (ES+) RT 5.3 min, 552.4 (M + H)+. |
| 34 | Ex 6 | 4-{Enantiomer 1(1R or S)-1-[2-(difluoromethoxy)phenyl]-7-fluoro-3,4-dihydro-1H-pyrano[4',3':4,5]imidazo[1,2-a]pyridin-8-yl}benzonitrile | LCMS (ES+) RT 4.58 min, 436.0 (M + H)+. |

-continued

| Example No. | Precursor | Compound Name | LCMS |
|---|---|---|---|
| 35 | Ex 6 | Enantiomer 1(1R or S)-1-[2-(difluoromethoxy)phenyl]-7-fluoro-8-(1H-pyrazol-4-yl)-3,4-dihydro-1H-pyrano[4′,3′:4,5]imidazo[1,2-a]pyridine 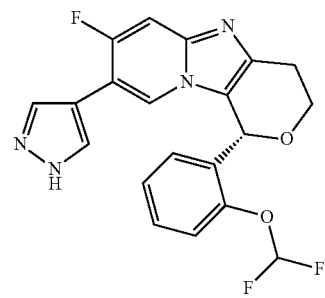 | LCMS (ES+) RT 1.30 min, 401.0 (M + H)+. |
| 36 | Ex 6 | Enantiomer 1(1R or S)-1-[2-(difluoromethoxy)phenyl]-7-fluoro-8-{4-[(methylsulfonyl)methyl]phenyl}-3,4-dihydro-1H-pyrano[4′,3′:4,5]imidazo[1,2-a]pyridine 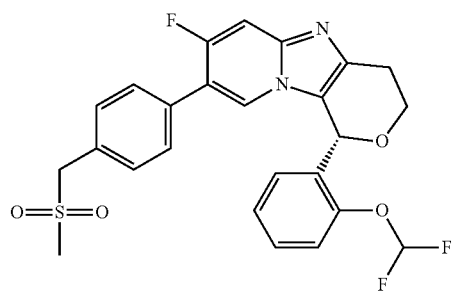 | LCMS (ES+) RT 3.41 min, 503.2 (M + H)+. |
| 37 | Ex 6 | (5-{Enantiomer 1(1R or S)-1-[2-(difluoromethoxy)phenyl]-7-fluoro-3,4-dihydro-1H-pyrano[4′,3′:4,5]imidazo[1,2-a]pyridin-8-yl}pyridin-2-yl)methanol 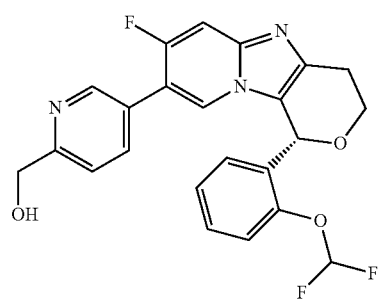 | LCMS (ES+) RT 3 min, 442.3 (M + H)+. |

| Example No. | Precursor | Compound Name | LCMS |
|---|---|---|---|
| 38 | Ex 3 | difluoromethyl 2-{8-[1-(phenylsulfonyl)-1H-pyrazol-4-yl]-3,4-dihydro-1H-pyrano[4',3':4,5]imidazo[1,2-a]pyridin-1-yl}phenyl ether | LCMS (ES⁺) RT 4.61 min, 523 (M + H)⁺. |
| 39 | Ex 3 | methyl 1-(5-{1-[2-(difluoromethoxy)phenyl]-3,4-dihydro-1H-pyrano[4',3':4,5]imidazo[1,2-a]pyridin-8-yl}pyrimidin-2-yl)piperidine-4-carboxylate | LCMS (ES⁺) RT 1.50 min, 536 (M + H)⁺. |
| 40 | Ex 7 | 1-(5-{Enantiomer 2: (4R or S)-1-[2-(difluoromethoxy)phenyl]-7-fluoro-3,4-dihydro-1H-pyrano[4',3':4,5]imidazo[1,2-a]pyridin-8-yl}pyrimidin-2-yl)-4-methylpiperidine-4-carboxylic acid ethyl ester | LCMS (ES⁺) RT 1.62 min, 582 (M + H)⁺. |

-continued

| Example No. | Precursor | Compound Name | LCMS |
|---|---|---|---|
| 41 | Ex 6 | 1-(5-{Enantiomer 1: (4S or R)-1-[2-(difluoromethoxy)phenyl]-7-fluoro-3,4-dihydro-1H-pyrano[4′,3′:4,5]imidazo[1,2-a]pyridin-8-yl}pyrimidin-2-yl)-4-methylpiperidine-4-carboxylic acid ethyl ester 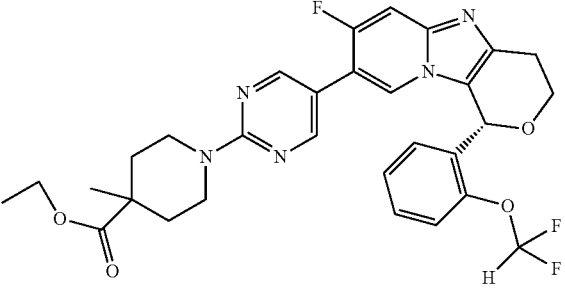 | LCMS (ES+) RT 1.62 min, 582 (M + H)+. |
| 42 | Ex 103 | 8-(6-methoxypyridin-3-yl)-1-phenyl-3,4-dihydro-1H-pyrano[4′,3′:4,5]imidazo[1,2-a]pyridine 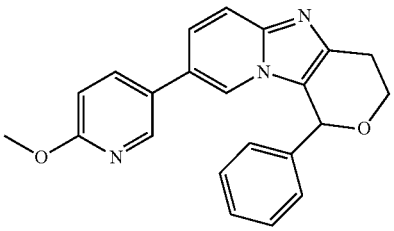 | LCMS (ES+) RT 5.67 min, 358 (M + H)+. |
| 43 | Ex 6 | Enantiomer 1: (4S or R)-1-[2-(difluoromethoxy)phenyl]-7-fluoro-8-[3-(methylsulfonyl)phenyl]-3,4-dihydro-1H-pyrano[4′,3′:4,5]imidazo[1,2-a]pyridine 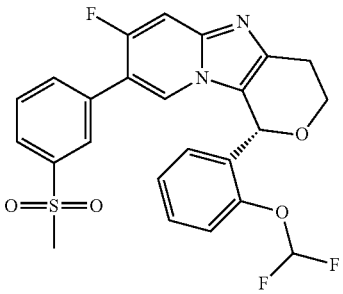 | LCMS (ES+) RT 3.97 min, 489 (M + H)+. |
| 44 | Ex 6 | Enantiomer 1: (4S or R)-1-[2-(difluoromethoxy)phenyl]-7-fluoro-8-[2-(methylsulfonyl)pyridin-4-yl]-3,4-dihydro-1H-pyrano[4′,3′:4,5]imidazo[1,2-a]pyridine 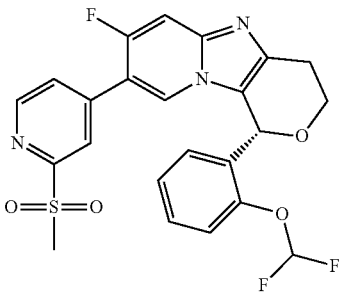 | LCMS (ES+) RT 4.06 min, 490 (M + H)+. |

-continued

| Example No. | Precursor | Compound Name | LCMS |
|---|---|---|---|
| 45 | Ex 9 | Enantiomer 1(4S or R)-8-fluoro-7-[4-(methylsulfonyl)phenyl]-4-phenyl-3,4-dihydro-1H-pyrano[3',4':4,5]imidazo[1,2-a]pyridine | LCMS (ES+) RT 4.28 min, 423 (M + H)+. |
| 46 | Ex 10 | Enantiomer 2(4R or S)-8-fluoro-7-[4-(methylsulfonyl)phenyl]-4-phenyl-3,4-dihydro-1H-pyrano[3',4':4,5]imidazo[1,2-a]pyridine | LCMS (ES+) RT 4.28 min, 423 (M + H)+. |
| 47 | Ex 11 | Enantiomer 1: (1S,4S or R)-1-[2-(difluoromethoxy)phenyl]-7-fluoro-8-[6-(tetrahydro-2H-pyran-4-yl)pyridin-3-yl]-3,4-dihydro-1H-pyrano[4',3':4,5]imidazo[1,2-a]pyridin-4-ol | LCMS (ES+) RT 3.56 min, 512 (M + H)+. |
| 48 | Ex 12 | Enantiomer 2 (1S,4R or S)-1-[2-(difluoromethoxy)phenyl]-7-fluoro-8-[6-(tetrahydro-2H-pyran-4-yl)pyridin-3-yl]-3,4-dihydro-1H-pyrano[4',3':4,5]imidazo[1,2-a]pyridin-4-ol | LCMS (ES+) RT 3.56 min, 512 (M + H)+. |

| Example No. | Precursor | Compound Name | LCMS |
|---|---|---|---|
| 49 | Ex 6 | N-(4-{Enantiomer 1(1S or R)-1-[2-(difluoromethoxy)phenyl]-7-fluoro-3,4-dihydro-1H-pyrano[4',3':4,5]imidazo[1,2-a]pyridin-8-yl}benzyl)-N-methylacetamide | LCMS (ES+) RT 3.26 min, 512.0 (M + H)+. |
| 50 | Ex 6 | Enantiomer 1(1S or R)-8-(2-cyclopropylpyrimidin-5-yl)-1-[2-(difluoromethoxy)phenyl]-7-fluoro-3,4-dihydro-1H-pyrano[4',3':4,5]imidazo[1,2-a]pyridine | LCMS (ES+) RT 3.71 min, 453.6 (M + H)+. |

Example 51

Enantiomer 1(1R or S)-1-[2-(difluoromethoxy)phenyl]-7-fluoro-8-[4-(5-meth 1-1H-1,2,4-triazol-3-yl)phenyl]-3,4-dihydro-1H-pyrano[4',3': 4,5]imidazo[1,2-a]pyridine

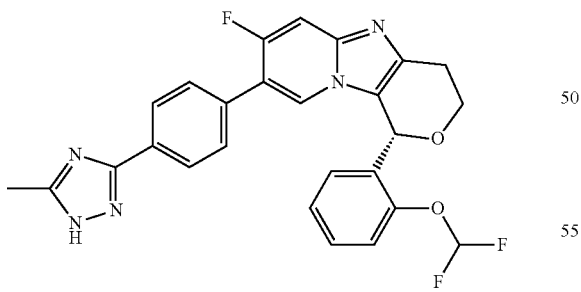

Example 34 (62 mg, 1 eq.), acetamidine hydrochloride (1.5 eq.), copper(I)bromide (0.05 eq.) and $Cs_2CO_3$ (3 eq.), were dissolved in DMSO (20 mL/g) and the mixture was heated for 18 h at 120° C. The mixture was quenched with water, extracted twice with EtOAc and the organic layers were concentrated in-vacuo. The residue was triturated in acetonitrile, yielding the title compound as beige solid (7 mg, 10% yield). LCMS (ES+) RT 3.94 min, 492.3 (M+H)+.

Example 52

Enantiomer 1(1R or S)-1-[2-(difluoromethoxy)phenyl]-7-fluoro-8-[1-(methylsulfonyl)-1H-pyrazol-4-yl]-3,4-dihydro-1H-pyrano[4',3': 4,5]imidazo[1,2-a]pyridine

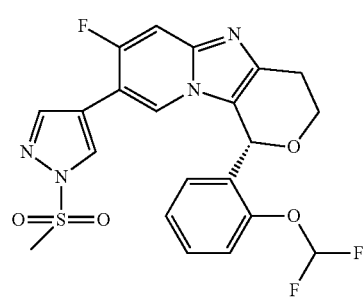 [SMILES: CS(=O)(=O)n1cc(-c2cn3c4c(nc3cc2F)CCO[C@@H]4c2ccccc2OC(F)F)cn1]

To a solution of Example 35(40 mg, 1 eq.) in DCM was added TEA (1.5 eq.). After stirring 5 min at r.t., methanesulfonyl chloride (1.2 eq.) was added. The mixture was stirred at r.t. for 5 min, diluted with DCM and washed with brine. The organic layers were concentrated and purified by reverse phase chromatography yielding the title compound as glassy solid (15 mg, 31% yield). $^1$H NMR (400 MHz, CDCl₃) δ 8.19 (d, J 1.8 Hz, 1H), 7.76 (s, 1H), 7.45 (td, J 7.9, 1.4 Hz, 1H), 7.41 (d, J 7.0 Hz, 1H), 7.32-7.38 (m, 2H), 7.20 (t, J 7.6 Hz, 1H), 7.09 (dd, J 7.7, 1.0 Hz, 1H), 6.72 (dd, J 76.1, 71.5 Hz, 1H), 6.37 (s, 1H), 4.26 (dt, J 11.2, 4.5 Hz, 1H), 4.03 (m, 1H), 3.36 (s, 3H), 3.16-3.26 (m, 1H), 3.00 (dt, J 16.5, 3.8 Hz, 1H). LCMS (ES⁺) RT 4.4 min, 479.2 (M+H)⁺.

Example 53

Enantiomer 1(1R or S)-1-[2-(difluoromethoxy)phenyl]-8-(2,3-dihydro-1H-isoindol-5-yl)-7-fluoro-3,4-dihydro-1H-pyrano[4',3':4,5]imidazo[1,2-a]pyridine

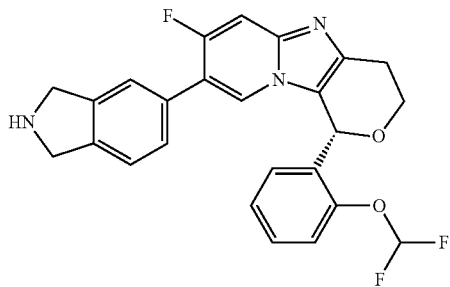 [SMILES: Fc1cc2nc3c(n2cc1-c1ccc2c(c1)CNC2)[C@@H](c1ccccc1OC(F)F)OCC3]

The title compound was prepared from Example 33, (190 mg, 1 eq) and trifluoroacetic acid (2 mL/g) by the Method D (2 mg, 1.3%). LCMS (ES⁺) RT 4.14 min, 452.3 (M+H)⁺

Example 54

Enantiomer 1(1R or S)-1-[2-(difluoromethoxy)phenyl]-7-fluoro-8-[2-(methylsulfonyl)-2,3-dihydro-1H-isoindol-5-yl]-3,4-dihydro-1H-pyrano[4',3':4,5]imidazo[1,2-a]pyridine

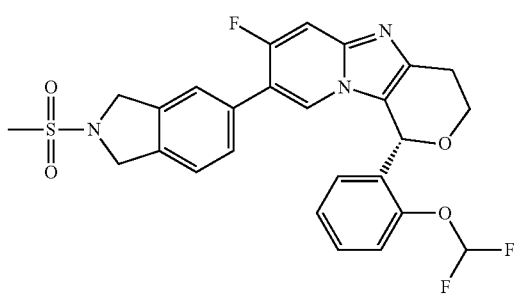 [SMILES: CS(=O)(=O)N1Cc2ccc(-c3cn4c5c(nc4cc3F)CCO[C@@H]5c3ccccc3OC(F)F)cc2C1]

The title compound was prepared from same method as for Example 52 from Example 54 (20 mg, 1 eq.), yielding the title compound as off white solid (2 mg, 8.5%). LCMS (ES⁺) RT 4.5 min, 530.2 (M+H)⁺.

Example 55

Enantiomer 1(1R or S)-)-1-[2-(difluoromethoxy)phenyl]-7-fluoro-8-{1-[2-(methylsulfonyl)ethyl]-1H-pyrazol-4-yl}-3,4-dihydro-1H-pyrano[4',3':4,5]imidazo-[1,2-a]pyridine

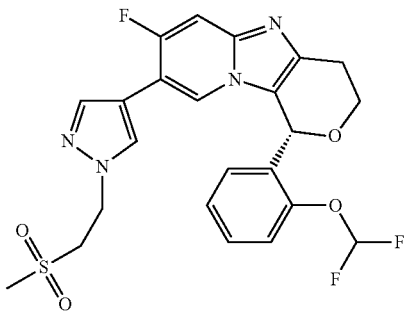 [SMILES: CS(=O)(=O)CCn1cc(-c2cn3c4c(nc3cc2F)CCO[C@@H]4c2ccccc2OC(F)F)cn1]

To a solution of Example 35 and K₂CO₃ (3 eq.) in acetonitrile (5 mL/mmol), 1-bromo-2-(methylsulfonyl)ethane (1.2 eq.) was added and the mixture was heated at 80° C. for 18 h in a closed vial. The reaction mixture was quenched with brine and extracted twice with EtOAc. The organic layers were dried (MgSO4) and concentrated yielding the title compound as a white solid (80 mg, 100%). ¹H NMR (400 MHz, CDCl₃) δ 7.70 (d, J 1.9 Hz, 1H), 7.53 (s, 1H), 7.44 (td, J 7.4, 1.5 Hz, 1H), 7.29-7.37 (m, 3H), 7.19 (t, J 7.2 Hz, 1H), 7.08 (dd, J 7.6, 1.2 Hz, 1H), 6.73 (t, J 76.5 Hz, 1H), 6.37 (s, 1H), 4.62 (t, J 6.2 Hz, 2H), 4.24 (td, J 9.6, 4.6 Hz, 1H), 4.02 (m, 1H), 3.64 (t, J 5.7 Hz, 2H), 3.18 (m, 1H), 2.99 (m, 1H), 2.55 (s, 3H). LCMS (ES⁺) RT 3.2 min, 507.3 (M+H)⁺.

Example 56

Enantiomer 1(1R or S)-)-1-[2-(difluoromethoxy)phenyl]-8-[1-(1,1-dioxidotetrahydrothiophen-3-yl)-1H-pyrazol-4-yl]-7-fluoro-3,4-dihydro-1H-pyrano[4',3':4,5]imidazo[1,2-a]pyridine

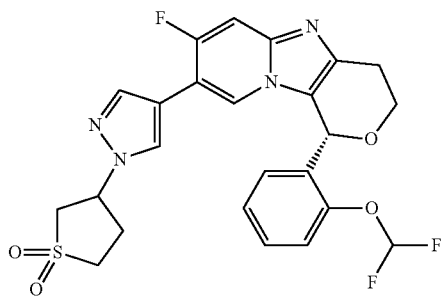 [SMILES: O=S1(=O)CCC(n2cc(-c3cn4c5c(nc4cc3F)CCO[C@@H]5c3ccccc3OC(F)F)cn2)C1]

The title compound was prepared following the Method used for Example 55 but from Example 35 and 3-bromotetrahydrothiophene 1,1-dioxide (1.2 eq.), yielding the title compound as a white solid (83 mg, 100% yield). ¹H NMR (400 MHz, CDCl₃) δ 7.69 (d, J 1.8 Hz, 1H), 7.51 (s, 1H), 7.44 (td, J 7.7, 1.4 Hz, 1H), 7.35 (t, J 7.0 Hz, 1H), 7.32 (d, J 11.4 Hz, 1H), 7.19 (t, J 7.7 Hz, 1H), 7.08 (dt, J 7.9, 1.5 Hz, 1H), 6.76 (m, 1H), 6.72 (dd, J 76.5, 71.5 Hz, 1H), 6.68 (dt, J 6.5, 2.2 Hz, 0.5H), 5.36 (s, 1H), 5.09 (quint, J 7.4 Hz, 1H), 4.24 (dt, J 11.2, 4.6 Hz, 1H), 4.02 (m, 1H), 3.56 (m, 2H), 3.21 (m, 2H), 2.98 (m, 2H), 2.73 (m, 2H). LCMS (ES$^+$) RT 3.3 min, 519.3 (M+H)$^+$.

Example 57

Enantiomer 1(1R or S)-1-[2-(difluoromethoxy)phenyl]-7-fluoro-8-{6-[(methylsulfonyl)methyl]pyridin-3-yl}-3,4-dihydro-1H-pyrano[4',3':4,5]imidazo[1,2-a]pyridine

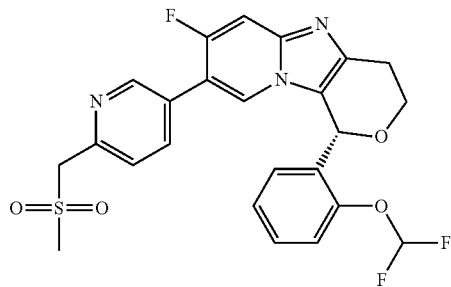 [SMILES: CS(=O)(=O)Cc1ccc(-c2cn3c4c(nc3cc2F)CCO[C@@H]4c2ccccc2OC(F)F)cn1]

To a solution of Intermediate 29 (61 mg, 1 eq.) in ethanol (16 mL/g), were added sodium methane sulfinate (4 eq.) and sodium iodide (0.1 eq.). The mixture was then heated at 100° C. under microwave irradiation for 15 min., concentrated, diluted in DCM, the organic layer was washed with water, dried (MgSO$_4$), concentrated and purified by chromatography on silica gel (EtOAc 100% followed by DCM/MeOH 98/2→95/5%), yielding the title compound as a white gum (21 mg, 31%). $^1$H NMR (400 MHz, CDCl$_3$) δ 8.48 (s, 1H), 7.71 (d, J 8.0 Hz, 1H), 7.52 (d, J 8.0 Hz, 1H), 7.44 (td, J 7.9, 1.5 Hz, 1H), 7.40 (d, J 10.8 Hz, 1H), 7.30 (m, 2H), 7.19 (t, J 7.6 Hz, 1H), 7.03 (dd, J 7.7, 1.2 Hz, 1H), 6.67 (dd, J 76.5, 71.7 Hz, 1H), 6.38 (s, 1H), 4.44 (s, 2H), 4.21 (dt, J 10.3, 4.8 Hz, 1H), 4.03 (ddd, J 12.0, 7.7, 4.5 Hz, 1H), 3.19 (dt, J 16.2, 5.7 Hz, 1H), 3.03 (m, 1H), 2.95 (s, 3H). LCMS (ES$^+$) RT 3.3 min, 504.2 (M+H)$^+$.

Example 58

Method E

1-[2-(difluoromethoxy)phenyl]-8-(4-methoxypiperidin-1-yl)-3,4-dihydro-1H-pyrano[4',3':4,5]imidazo[1,2-a]pyridine

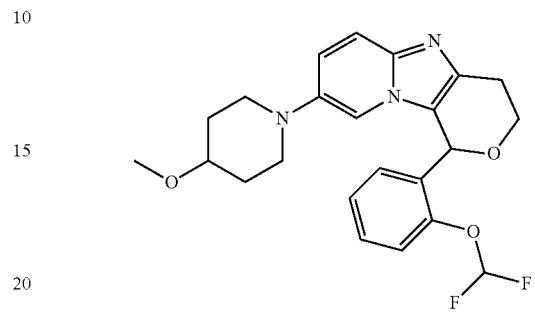

To a solution of Example 3 in Dioxane (20 mL/mmol) were added 4-methoxypiperidine (1.5 eq.), tBuONa (2.4 eq.) and Pd$_2$dba$_3$ (0.1 eq.), Xantphos (0.2 eq.) and cesium fluoride (4 eq.). The reaction mixture was degassed and heated under microwave irradiation at 120° C. for 1 h. The mixture was filtered through a 45 μm pore size filter and concentrated. The residue was purified by flash chromatography (DCM/methanolic ammonia 95/5) to give the pure desired product, yielding the title compound as an off white solid film (8 mg, 15% yield). $^1$H NMR (400 MHz, CDCl$_3$) δ 7.61 (d, J 9.8 Hz, 1H), 7.45 (t, J 7.4 Hz, 1H), 7.33 (d, J 8.2 Hz, 1H), 7.20 (t, J 7.7 Hz, 1H), 7.15 (dd, J 9.8, 1.4 Hz, 1H), 7.06 (d, J 7.5 Hz, 1H), 6.70 (dd, J 76.6, 71.1 Hz, 1H), 6.68 (s, 1H), 6.33 (s, 1H), 4.22 (dt, J 11.0, 4.8 Hz, 1H), 4.02 (ddd, J 11.9, 8.1, 4.6 Hz, 1H), 3.36 (s, 3H), 3.31 (m, 1H), 3.14-3.26 (m, 2H), 2.97-3.10 (m, 2H), 2.70 (m, 1H), 2.60 (m, 1H), 1.93 (m, 2H), 1.67 (m, 2H). LCMS (ES$^+$) RT 4.3 min, 430.2 (M+H)$^+$.

Examples 59-62

The following Examples were prepared using Method E from the assigned precursor using the appropriate amine, either available commercially or prepared as set out in the intermediates above.

| Example No. | Precursor | Compound Name | $^1$H NMR/LCMS |
|---|---|---|---|
| 59 | Ex 3 | 1-[2-(difluoromethoxy)phenyl]-8-[3-(methoxymethyl)pyrrolidin-1-yl]-3,4-dihydro-1H-pyrano[4',3':4,5]imidazo[1,2-a]pyridine 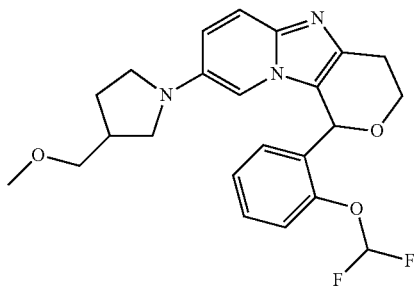 | LCMS (ES$^+$) RT 4.5 min, 430.1 (M + H)$^+$. |

-continued

| Example No. | Precursor | Compound Name | ¹H NMR/LCMS |
|---|---|---|---|
| 60 | Ex 3 | 1-[2-(difluoromethoxy)phenyl]-8-[4-(methylsulfonyl)piperazin-1-yl]-3,4-dihydro-1H-pyrano[4′,3′:4,5]imidazo[1,2-a]pyridine 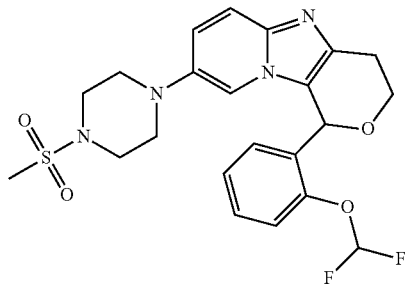 | LCMS (ES+) RT 3.97 min, 479 (M + H)+. |
| 61 | Ex 3 | 1-[2-(difluoromethoxy)phenyl]-8-(3-methoxyazetidin-1-yl)-3,4-dihydro-1H-pyrano[4′,3′:4,5]imidazo[1,2-a]pyridine 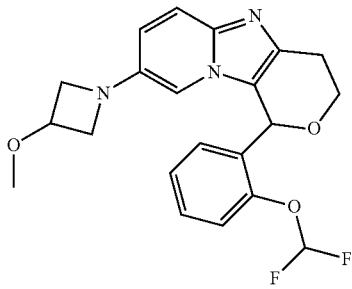 | LCMS (ES+) RT 4.15 min, 402 (M + H)+. |
| 62 | Ex 3 | 1-[2-(difluoromethoxy)phenyl]-8-(3-methoxypyrrolidin-1-yl)-3,4-dihydro-1H-pyrano[4′,3′:4,5]imidazo[1,2-a]pyridine 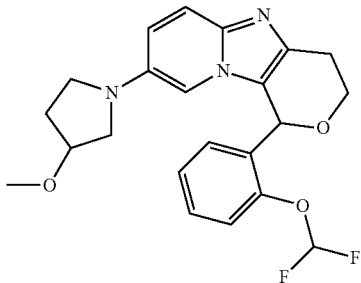 | LCMS (ES+) RT 4.29 min, 416 (M + H)+. |

Example 63

1-[2-(difluoromethoxy)phenyl]-8-(1H-pyrazol-4-yl)-3,4-dihydro-1H-pyrano[4',3':4,5]imidazo[1,2-a]pyridine

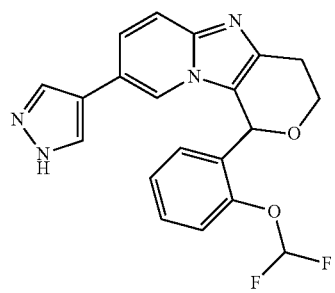 [SMILES: FC(F)Oc1ccccc1C1OCCc2nc3ccc(-c4cn[nH]c4)cn3c21]

To Example 31 (20 mg, 1 eq.) dissolved in THF (200 mL/mmol) was added TBAF (6 eq.) and the mixture was stirred and heated to reflux for 4 h. The mixture was quenched with brine, extracted twice with EtOAc. The organic layers were dried (MgSO$_4$), concentrated and purified by reverse phase chromatography, yielding the title compound as an orange oil (20.7 mg, 100%). $^1$H NMR (400 MHz, CDCl$_3$) δ 5.75 (m, 3H), 5.63 (m, 1H), 5.55 (m, 3H), 5.40 (m, 1H), 5.30 (m, 1H), 5.09 (m, 1H), 4.81 (s, 1H), 3.11 (m, 1H), 2.99 (m, 1H), 2.27 (m, 1H), 2.15 (m, 1H). LCMS (ES$^+$) RT 3.7 min, 383 (M+H)$^+$.

Example 64

Method F 1-(5-{(1-[2-(difluoromethoxy)phenyl]-3,4-dihydro-1H-pyrano[4',3':4,5]imidazo[1,2-a]pyridin-8-yl}pyrimidin-2-yl)piperidine-4-carboxylic acid

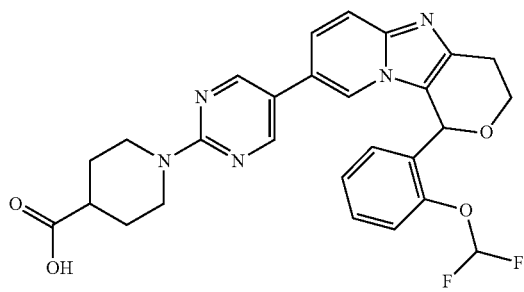 [SMILES: O=C(O)C1CCN(c2ncc(-c3ccc4nc5c(n4c3)C(c3ccccc3OC(F)F)OCC5)cn2)CC1]

Example 39 (0.234 g, 0.44 mmol) was dissolved in THF (3 mL) and 2 mL water. Lithium hydroxide monohydrate (0.037 g, 0.87 mmol) was added and the reaction was stirred at r.t. for 18 h. The reaction was concentrated in vacuo and dissolved in a minimal amount of water. The mixture was treated with a few drops of 6M HCl and a precipitate formed. The precipitate was filtered off and dried in vacuo. The solid was purified by prep-HPLC yielding the title compound as an off white solid (0.076 g, 33%). 1H NMR (DMSO-d6, 400 MHz) δ: 12.34 (s, 1H), 8.44 (s, 2H), 7.66 (m, 2H), 7.49 (m, 1H), 7.34 (d, J 8.1 Hz, 1H), 7.27 (s, 1H), 7.17 (m, 1H), 6.81 (dd, J 7.6 Hz, J 1.4 Hz, 1H), 6.42 (s, 1H), 4.50 (m, 2H), 3.94 (t, J 5.4 Hz, 2H), 3.08 (m, 2H), 2.94 (m, 2H), 2.53 (m, 2H), 1.87 (m, 2H), 1.47 (m, 2H). LCMS (ES$^+$) RT 1.86 min, 522.1 (M+H)$^+$.

Example 65

1-(5-{enantiomer 2: (1R or S)-1-[2-(difluoromethoxy)phenyl]7-fluoro-3,4-dihydro-1H-pyrano[4',3':4,5]imidazo[1,2-a]pyridin-8-yl}pyrimidin-2-yl)-4-methylpiperidine-4-carboxylic acid

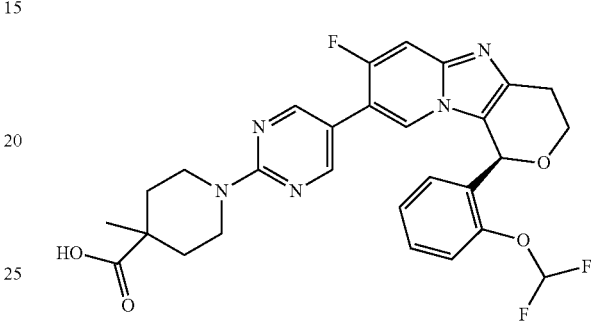

The title compound was prepared from Example 40 (0.25 g, 0.43 mmol) and lithium hydroxide monohydrate (0.036 g, 0.87 mmol) by the Method F (0.12 g, 53%). LCMS (ES$^+$) RT 1.40 min, 554.2 (M+H)+.

Example 66

1-(5-{enantiomer 1: (1S or R)-1-[2-(difluoromethoxy)phenyl]7-fluoro-3,4-dihydro-1H-pyrano[4',3':4,5]imidazo[1,2-a]pyridin-8-yl}pyrimidin-2-yl)-4-methylpiperidine-4-carboxylic acid

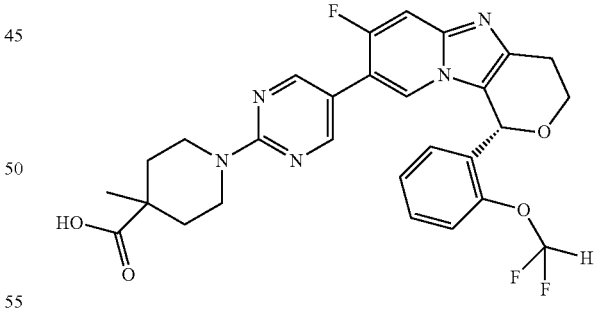

The title compound was prepared from Example 41 (0.25 g, 0.43 mmol) and lithium hydroxide monohydrate (0.036 g, 0.87 mmol) by the Method F (0.12 g, 53%). LCMS (ES$^+$) RT 1.40 min, 554.2 (M+H)+.

Examples 67-98

The following Examples were prepared using Method A and subsequently Method B from the assigned precursor using the appropriate aldehyde.

| Example No. | Precursor | Compound Name | LCMS |
|---|---|---|---|
| 67 | Int 22 | 1-(5-chloro-2-methylthiazol-4-yl)-7-fluoro-8-(2-morpholinopyrimidin-5-yl)-3,4-dihydro-1H-pyrano[4',3':4,5]imidazo[1,2-a]pyridine | LCMS (ES+) RT 3.34 min, 487.0 (M + H)+. |
| 68 | Int 22 | 1-(5-chloro-2-(difluoromethoxy)phenyl)-7-fluoro-8-(2-morpholinopyrimidin-5-yl)-3,4-dihydro-1H-pyrano[4',3':4,5]imidazo[1,2-a]pyridine | LCMS (ES+) RT 3.78 min, 532.0 (M + H)+. |
| 69 | Int 22 | 1-(5-chloro-2-(trifluoromethoxy)phenyl)-7-fluoro-8-(2-morpholinopyrimidin-5-yl)-3,4-dihydro-1H-pyrano[4',3':4,5]imidazo[1,2-a]pyridine | LCMS (ES+) RT 3.89 min, 550.0 (M + H)+. |
| 70 | Int 22 | 1-(2-chlorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.62 min, 466.0 (M + H)+. |

| Example No. | Precursor | Compound Name | LCMS |
|---|---|---|---|
| 71 | Int 22 | 1-(3-chlorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.66 min, 466.0 (M + H)+. |
| 72 | Int 22 | 1-(3-(difluoromethoxy)phenyl)-7-fluoro-8-(2-morpholinopyrimidin-5-yl)-3,4-dihydro-1H-pyrano[4',3':4,5]imidazo[1,2-a]pyridine | LCMS (ES+) RT 3.58 min, 498.0 (M + H)+. |
| 73 | Int 22 | 1-(2,5-dimethylphenyl)-7-fluoro-8-(2-morpholinopyrimidin-5-yl)-3,4-dihydro-1H-pyrano[4',3':4,5]imidazo[1,2-a]pyridine | LCMS (ES+) RT 3.74 min, 460.0 (M + H)+. |
| 74 | Int 22 | 1-(2,5-dichlorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.79 min, 500.0 (M + H)+. |

| Example No. | Precursor | Compound Name | LCMS |
|---|---|---|---|
| 75 | Int 22 | 1-(2-chloro-6-(difluoromethoxy)phenyl)-7-fluoro-8-(2-morpholinopyrimidin-5-yl)-3,4-dihydro-1H-pyrano[4',3':4,5]imidazo[1,2-a]pyridine | LCMS (ES+) RT 3.64 min, 532.0 (M + H)+. |
| 76 | Int 22 | 7-fluoro-8-(2-morpholinopyrimidin-5-yl)-1-(2-(trifluoromethoxy)phenyl)-3,4-dihydro-1H-pyrano[4',3':4,5]imidazo[1,2-a]pyridine | LCMS (ES+) RT 3.80 min, 516.0 (M + H)+. |
| 77 | Int 22 | 1-(2-chloro-6-(trifluoromethoxy)phenyl)-7-fluoro-8-(2-morpholinopyrimidin-5-yl)-3,4-dihydro-1H-pyrano[4',3':4,5]imidazo[1,2-a]pyridine | LCMS (ES+) RT 3.80 min, 550.0 (M + H)+. |
| 78 | Int 22 | 7-fluoro-8-(2-morpholinopyrimidin-5-yl)-1-(2-(trifluoromethyl)phenyl)-3,4-dihydro-1H-pyrano[4',3':4,5]imidazo[1,2-a]pyridine | LCMS (ES+) RT 3.74 min, 500.0 (M + H)+. |

| Example No. | Precursor | Compound Name | LCMS |
|---|---|---|---|
| 79 | Int 22 | 1-(2,5-bis(difluoromethoxy)phenyl)-7-fluoro-8-(2-morpholinopyrimidin-5-yl)-3,4-dihydro-1H-pyrano[4′,3′:4,5]imidazo[1,2-a]pyridine | LCMS (ES+) RT 3.66 min, 564.0 (M + H)+. |
| 80 | Int 22 | 1-(2-(difluoromethoxy)-5-fluorophenyl)-7-fluoro-8-(2-morpholinopyrimidin-5-yl)-3,4-dihydro-1H-pyrano[4′,3′:4,5]imidazo[1,2-a]pyridine | LCMS (ES+) RT 3.61 min, 516.0 (M + H)+. |
| 81 | Int 22 | 1-(2-(difluoromethoxy)-3,5-difluorophenyl)-7-fluoro-8-(2-morpholinopyrimidin-5-yl)-3,4-dihydro-1H-pyrano[4′,3′:4,5]imidazo[1,2-a]pyridine | LCMS (ES+) RT 3.67 min, 534.0 (M + H)+. |

| Example No. | Precursor | Compound Name | LCMS |
|---|---|---|---|
| 82 | Int 22 | 1-(2-(difluoromethoxy)-3-fluorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.66 min, 516.0 (M + H)+. |
| 83 | Int 22 | 1-(2-chloro-5-fluorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.65 min, 484.0 (M + H)+. |
| 84 | Int 22 | 1-(5-chloro-2-fluorophenyl)-7-fluoro-8-(2-morpholinopyrimidin-5-yl)-3,4-dihydro-1H-pyrano[4',3':4,5]imidazo[1,2-a]pyridine | LCMS (ES+) RT 3.65 min, 484.0 (M + H)+. |
| 85 | Int 22 | 1-(4,6-dimethoxypyrimidin-5-yl)-7-fluoro-8-(2-morpholinopyrimidin-5-yl)-3,4-dihydro-1H-pyrano[4',3':4,5]imidazo[1,2-a]pyridine | LCMS (ES+) RT 3.18 min, 494.0 (M + H)+. |

| Example No. | Precursor | Compound Name | LCMS |
|---|---|---|---|
| 86 | Int 22 | 7-fluoro-1-(2-methyl-4-(trifluoromethyl)thiazol-5-yl)-8-(2-morpholinopyrimidin-5-yl)-3,4-dihydro-1H-pyrano[4',3':4,5]imidazo[1,2-a]pyridine | LCMS (ES+) RT 3.51 min, 521.0 (M + H)+. |
| 87 | Int 22 | 1-[4-(difluoromethoxy)phenyl]-7-fluoro-8-[2-(morpholin-4-yl)pyrimidin-5-yl]-3,4-dihydro-1H-pyrano[4',3':4,5]imidazo[1,2-a]pyridine | LCMS (ES+) RT 3.60 min, 498.0 (M + H)+. |
| 88 | Int 22 | 1-(4-chlorophenyl)-7-fluoro-8-[2-(morpholin-4-yl)pyrimidin-5-yl]-3,4-dihydro-1H-pyrano[4',3':4,5]imidazo[1,2-a]pyridine | LCMS (ES+) RT 2.08 min, 466.0 (M + H)+. |

| Example No. | Precursor | Compound Name | LCMS |
|---|---|---|---|
| 89 | Int 22 | 3-{7-fluoro-8-[2-(morpholin-4-yl)pyrimidin-5-yl]-3,4-dihydro-1H-pyrano[4′,3′:4,5]imidazo[1,2-a]pyridin-1-yl}benzonitrile 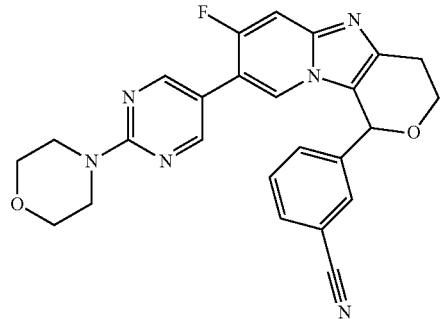 | LCMS (ES+) RT 1.38 min, 466.0 (M + H)+. |
| 90 | Int 22 | 7-fluoro-1-(4-methyl-1,3-thiazol-5-yl)-8-[2-(morpholin-4-yl)pyrimidin-5-yl]-3,4-dihydro-1H-pyrano[4′,3′:4,5]imidazo[1,2-a]pyridine 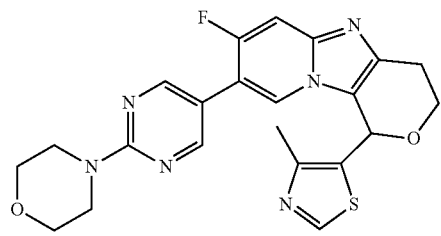 | LCMS (ES+) RT 1.25 min, 453.0 (M + H)+. |
| 91 | Int 22 | 1-(2,4-dimethyl-1,3-thiazol-5-yl)-7-fluoro-8-[2-(morpholin-4-yl)pyrimidin-5-yl]-3,4-dihydro-1H-pyrano[4′,3′:4,5]imidazo[1,2-a]pyridine 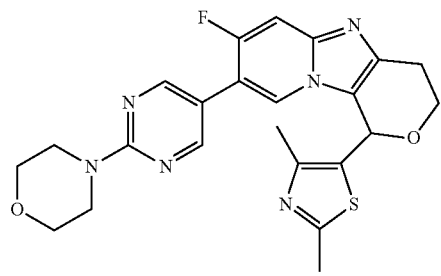 | LCMS (ES+) RT 1.25 min, 467.0 (M + H)+. |
| 92 | Int 22 | 4-{7-fluoro-8-[2-(morpholin-4-yl)pyrimidin-5-yl]-3,4-dihydro-1H-pyrano[4′,3′:4,5]imidazo[1,2-a]pyridin-1-yl}benzonitrile 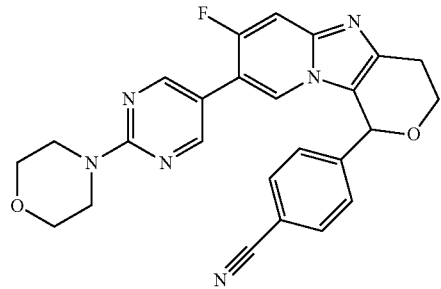 | LCMS (ES+) RT 1.33 min, 457.0 (M + H)+. |

-continued

| Example No. | Precursor | Compound Name | LCMS |
|---|---|---|---|
| 93 | Int 22 | 2-{7-fluoro-8-[2-(morpholin-4-yl)pyrimidin-5-yl]-3,4-dihydro-1H-pyrano[4',3':4,5]imidazo[1,2-a]pyridin-1-yl}benzonitrile | LCMS (ES+) RT 1.32 min, 457.0 (M + H)+. |
| 94 | Int 22 | 7-fluoro-1-(5-methoxypyrazin-2-yl)-8-[2-(morpholin-4-yl)pyrimidin-5-yl]-3,4-dihydro-1H-pyrano[4',3':4,5]imidazo[1,2-a]pyridine | LCMS (ES+) RT 1.29 min, 464.0 (M + H)+. |
| 95 | Int 22 | 7-fluoro-1-[4-(methylsulfonyl)phenyl]-8-[2-(morpholin-4-yl)pyrimidin-5-yl]-3,4-dihydro-1H-pyrano[4',3':4,5]imidazo[1,2-a]pyridine | LCMS (ES+) RT 1.24 min, 510.0 (M + H)+. |
| 96 | Int 22 | 6-chloro-7-fluoro-8'-[2-(morpholin-4-yl)pyrimidin-5-yl]-2,3,3',4'-tetrahydrospiro[indene-1,1'-pyrano[4',3':4,5]imidazo[1,2-a]pyridine] | LCMS (ES+) RT 1.35 min, 492.0 (M + H)+. |

-continued

| Example No. | Precursor | Compound Name | LCMS |
|---|---|---|---|
| 97 | Int 22 | 1-(4-chloro-1,3-thiazol-5-yl)-7-fluoro-8-[2-(morpholin-4-yl)pyrimidin-5-yl]-3,4-dihydro-1H-pyrano[4',3':4,5]imidazo[1,2-a]pyridine | LCMS (ES+) RT 1.35 min, 473.0 (M + H)+. |
| 98 | Int 10 | 8-bromo-1-(2-methoxypyridin-3-yl)-3,4-dihydro-1H-pyrano[4',3':4,5]imidazo[1,2-a]pyridine | LCMS (ES+) RT 3.72 min, 360.2/362.2 (M + H)+. |

Example 99

2-(6-methoxypyridin-3-yl)-10-phenyl-7,8,9,10-tetrahydro-6H-cyclohepta[4,5]imidazo[1,2-a]pyridin-10-ol

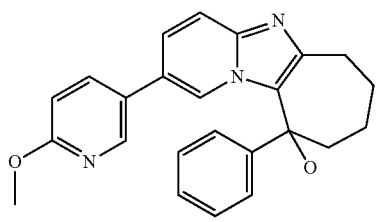 [SMILES: COc1ccc(-c2ccc3nc4c(n3c2)C(O)(c2ccccc2)CCCC4)cn1]

Phenyl magnesium bromide (1M in THF, 650 µl, 0.66 mmol, 4.00 eq.) was added to a cooled (0° C.) solution of Intermediate 24 (50 mg, 016 mmol) in anhydrous THF (2 ml). After addition the temperature was allowed to reach r.t. and the reaction was stirred for 2 h. The reaction mixture was quenched with sat. aq. NH$_4$Cl, then rendered alkaline with K$_2$CO$_3$(s). The aqueous mixture was extracted with EtOAc (2×). The combined organic layers were washed with brine, dried over Na$_2$SO$_4$ and concentrated in vacuo. The residue was purified by column chromatography (silica gel, 5% MeOH in DCM) to yielding the title compound as a yellow solid (38 mg, 60%). 1H NMR (300 MHz, CDCl$_3$) δ 8.05 (s, 1H), 8.01 (d, J 2.0 Hz, 1H), 7.54 (d, J 9.2 Hz, 1H), 7.43 (dd, J 8.6, 2.5 Hz, 1H), 7.38-7.19 (m, 6H), 6.71 (d, J 8.6 Hz, 1H), 3.92 (s, 3H), 3.22-3.00 (m, 2H), 2.60 (br s, 1H), 2.48-2.28 (m, 2H), 2.06-1.74 (m, 3H), 1.70-1.48 (m, 1H).

Example 100

8-chloro-1-phenyl-3,4-dihydro-1H-pyrano[4',3':4,5]imidazo[1,2-a]pyridine

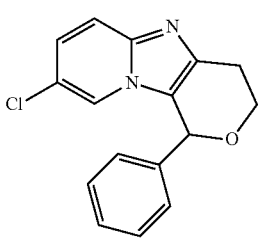 [SMILES: Clc1ccc2nc3c(n2c1)C(c1ccccc1)OCC3]

The title compound was prepared from Intermediate 2 (0.200 g, 1.02 mmol) and dimethoxymethylbenzene (155 mg, 1.02 mmol) by the Method B (90 mg, 78%). LCMS (ES+) 285.1/287.1 (M+H)+.

Example 101

(1R or S,4S or R)-1-[2-(difluoromethoxy)phenyl]-7-fluoro-8-[4-(methylsulfonyl)phenyl]-3,4-dihydro-1H-pyrano[4',3':4,5]imidazo[1,2-a]pyridin-4-ol

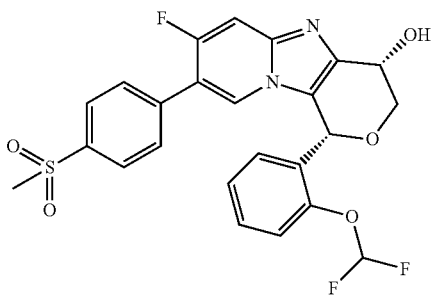 [SMILES: CS(=O)(=O)c1ccc(-c2cn3c4c(nc3cc2F)[C@H](O)CO[C@@H]4c2ccccc2OC(F)F)cc1]

A solution A was prepared with Example 27 (5.07 mg, 0.0113 mmol, 1 eq) in 2 mL of acetonitrile and was diluted with 8 mL of water to reach a 0.5 mg/mL. A solution B was prepared from a solution of D-Glucose 6-phosphate disodium salt hydrate (2.113 g, 100 mM), B-nicotinamide adenine dinucleotide phosphate (533.5 mg, 10 mM) and 700 µL of $MgCl_2.6H_2O$ (1 M) in 69 mL of phosphate buffer (100 mM, pH=7.4). In a glassware tube, 5.5 mL of phosphate buffer, 1 mL of mouse microsome (20 mg/mL Male CD1 pool of 1042, M1000), 1 mL of solution A, 2.5 mL of solution B, 12 µL of glucose-6-phosphate dehydrogenase was incubated at 37° C. under swelling for 30 minutes. The incubation was stopped by addition of 5 mL of acetonitrile and the tube was centrifuged for 15 minutes at 3000 rpm. The title compound was purified from the supernatant by preparative 2D LCMS yielding the title compound as a white solid (312 µg, 6%). $^1$H NMR (400 MHz, DMSO-$d_6$) δ (d, J 8.0 Hz, 2H), 7.57 (m, 5H), 7.30 (m, 2H), 7.07 (m, 2H), 6.37 (s, 1H), 5.60 (m, 1H), 4.76 (m, 1H), 3.81 (m, 2H), 3.23 (s, 3H). LCMS (ES$^+$) RT 3.67 min, 505 (M+H)$^+$.

Examples 102-106

The following Examples were prepared using Method C from the assigned precursor using the appropriate boronic acid or boronate ester, either available commercially or prepared as set out in the intermediates above.

| Example No. | Precursor | Compound Name | LCMS |
|---|---|---|---|
| 102 | Int 30 | 2-(4-{(1R,4S)-1-[5-chloro-2-(difluoromethoxy)phenyl]-7-fluoro-4-hydroxy-3,4-dihydro-1H-pyrano[4',3':4,5]imidazo[1,2-a]pyridin-8-yl}phenyl)-2-methylpropanenitrile | LCMS (ES$^+$) RT 1.50 min 528.0 (M + H)$^+$. |
| 103 | Int 31 | 2-(4-{(1S,4S)-1-[5-chloro-2-(difluoromethoxy)phenyl]-7-fluoro-4-hydroxy-3,4-dihydro-1H-pyrano[4',3':4,5]imidazo[1,2-a]pyridin-8-yl}phenyl)-2-methylpropanenitrile | LCMS (ES$^+$) RT 1.52 min 528.0 (M + H)$^+$. |

-continued

| Example No. | Precursor | Compound Name | LCMS |
|---|---|---|---|
| 104 | Int 30 | (1R,4S)-1-[2-(difluoromethoxy)phenyl]-7-fluoro-8-[2-(tetrahydro-2H-pyran-4-yl)pyrimidin-5-yl]-3,4-dihydro-1H-pyrano[4',3':4,5]imidazo[1,2-a]pyridin-4-ol | LCMS (ES+) RT 1.50 min 513.0 (M + H)+. |
| 105 | Int 31 | (1S,4S)-1-[2-(difluoromethoxy)phenyl]-7-fluoro-8-[2-(tetrahydro-2H-pyran-4-yl)pyrimidin-5-yl]-3,4-dihydro-1H-pyrano[4',3':4,5]imidazo[1,2-a]pyridin-4-ol | LCMS (ES+) RT 1.50 min 513.0 (M + H)+. |
| 106 | Ex 6 | 2-(5-{(1R)-1-[2-(difluoromethoxy)phenyl]-7-fluoro-3,4-dihydro-1H-pyrano[4',3':4,5]imidazo[1,2-a]pyridin-8-yl}pyrimidin-2-yl)propan-2-ol | LCMS (ES+) RT 1.50 min 471.0 (M + H)+. |

Example 107

(1R)-1-[2-(difluoromethoxy)phenyl]-7-fluoro-8-[2-(2-fluoropropan-2-yl)pyrimidin-5-yl]-3,4-dihydro-1H-pyrano[4',3':4,5]imidazo[1,2-a]pyridine

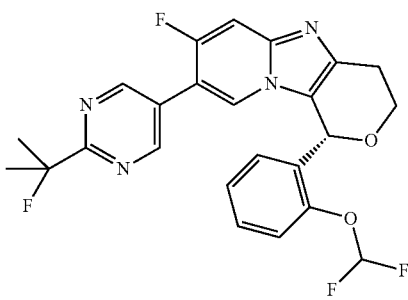 [SMILES: CC(C)(F)c1ncc(-c2cn3c4c(nc3cc2F)CCO[C@@H]4c2ccccc2OC(F)F)cn1]

To a solution of Example 106 (308 mg, 0.655 mmol) in 3 mL of DCM was added at 0° C., difluoro(morpholino)sulfonium tetrafluoroborate (175 mg, 0.720 mmol) by portion. The reaction was stirred for 30 minutes at 0° C. and then for 18 h at r.t. A saturated solution of NaHCO$_3$ (2 mL) was added. The aqueous layer was extracted by ethyl acetate (2×3 mL), combined organic layers were dried over magnesium sulfate and concentrated in vacuo. The residue was purified by column chromatography (SiO$_2$, 24% EtOAc in heptane) yielding the title compound as a white solid (65 mg, 21%). LCMS (ES$^+$) RT 4.53 min, 473.3 (M+H)$^+$.

Example 108

(4R or S)-4-[2-(difluoromethoxy)phenyl]-7-[6-(methylsulfonyl)pyridin-3-yl]-3,4-dihydroimidazo[1,2-a:4,5-c']dipyridin-1(2H)-one and (4S or R)-4-[2-(difluoromethoxy)phenyl]-7-[6-(methylsulfonyl)pyridin-3-yl]-3,4-dihydroimidazo[1,2-a:4,5-c']dipyridin-1(2H)-one

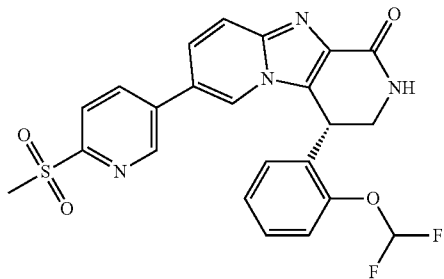 [SMILES: CS(=O)(=O)c1ccc(-c2ccc3nc4c(n3c2)[C@@H](c2ccccc2OC(F)F)CNC4=O)cn1]

To a solution of Intermediate 39 (250 mg, 0.53 mmol) in (2:1) DCM (4 mL): methanesulfonic acid (2 mL) at 0° C. was added portion wise sodium azide (51.93 mg, 0.8 mmol) and the resulting mixture was allowed to warm to r.t. and stirred for 48 h. The reaction mixture was poured on to water, basified with 6N NaOH and extracted with DCM (50 mL×2). The combined organic layers were dried over magnesium sulfate, concentrated in vacuo. The residue was purified by Chiral HPLC (20:80 MeOH:CO$_2$ with Cellulose 3 column) yielding Example 108 as a pale yellow solid RT 4.79 minutes (8.3 mg, 7%). $^1$H NMR (500 MHz, DMSO-d6) δ 9.04 (d, J 2.1 Hz, 1H), 8.53 (s, 1H), 8.39 (dd, J 8.2, 2.3 Hz, 1H), 8.11 (d, J 8.3 Hz, 1H), 7.89 (d, J 9.5 Hz, 1H), 7.81 (dd, J 9.6, 1.7 Hz, 1H), 7.63-7.52 (m, 1H), 7.47-6.99 (m, 4H), 6.40-6.32 (m, 1H), 5.19-5.01 (m, 1H), 4.08 (dd, J 12.7, 5.8 Hz, 1H), 3.58-3.47 (m, 1H), 3.29 (s, 3H). LCMS (ES$^+$) RT 1.21 min, 485.0 (M+H)$^+$.

The invention claimed is:

1. A compound represented by formula (I), or a pharmaceutically acceptable salt thereof,

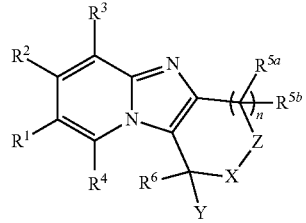

(I)

wherein n represents an integer equal to 1 or 2;

Y represents C$_{3-7}$ cycloalkyl, aryl, C$_{3-7}$ heterocycloalkyl or heteroaryl, any of which groups may be optionally substituted by one, two or three substituents independently selected from halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, (C$_{1-6}$)alkylsulfonyloxy, amino, C$_{1-6}$ alkyl-amino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkyl-aminocarbonyl, aminosulfonyl, C$_{1-6}$ alkylaminosulfonyl and di(C$_{1-6}$)alkylaminosulfonyl;

X and Z independently represent a heteroatom; carbonyl, —S(O)—, —S(O)$_2$—, —S(O)(N—R$^d$), —NC(O)R$^d$, —N(CO)—OR$^d$, —NS(O)$_2$R$^d$ or —N(R$^d$); or X and Z independently represent a straight or branched C$_{1-4}$ alkylene chain optionally substituted by one or more substituents selected from halogen, hydroxy, oxo, C$_{1-6}$ alkoxy, aryl, —C(O)R$^d$, —CO$_2$R$^d$, —CONR$^b$R$^c$—S(O)(N—R$^d$)R$^a$, or —SO$_2$NR$^b$R$^c$;

R$^1$ represents cyano or R$^1$ represents C$_{1-6}$ alkyl, C$_{2-6}$ alkynyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl-(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl-, heteroaryl-aryl, or (C$_{4-9}$)spiroheterocycloalkyl-heteroaryl-, any of which groups may be optionally substituted by one, two or three substituents independently selected from halogen, halo(C$_{1-6}$)alkyl, cyano, cyano(C$_{1-6}$)alkyl, nitro(C$_{1-6}$) alkyl, C$_{1-6}$ alkyl, trifluoromethyl, trifluoroethyl, C$_{2-6}$ alkenyl, hydroxy, hydroxy(C$_{1-6}$)alkyl, C$_{1-6}$ alkoxy, trifluoroethoxy, carboxy(C$_{3-7}$)cycloalkyloxy, C$_{1-6}$ alkylthio, C$_{1-6}$ alkylsulphonyl, aryl-sulphonyl, (C$_{1-6}$)alkylsulphonyl(C$_{1-6}$)alkyl, oxo, amino, amino-(C$_{1-6}$)alkyl, C$_{1-6}$ alkylamino, di(C$_{1-6}$)alkylamino, (C$_{1-6}$)alkoxy ($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, di($C_{1-6}$)alkylaminocarbonyl, aminosulphonyl, ($C_{1-6}$)alkylsulphoximinyl and [($C_{1-6}$)alkyl][N—($C_{1-6}$)alkyl]sulphoximinyl;

$R^2$ represents hydrogen, halogen, cyano, nitro, hydroxy, trifluoromethyl, trifluoromethoxy or —$OR^a$; or $R^2$ represents $C_{1-6}$ alkyl optionally substituted by $C_{2-6}$ alkoxycarbonyl;

$R^3$ and $R^4$ independently represents hydrogen, halogen, cyano, nitro, hydroxy, trifluoromethyl, trifluoromethoxy or —$OR^a$; or $C_{1-6}$ alkyl;

$R^{5a}$ and $R^{5b}$ independently represent hydrogen, hydroxy, halogen, trifluoromethyl, cyano; —$NR^bR^c$, —$S(O)_2R^a$, —$OR^a$, or —$O(CO)$—$R^d$—; or $R^{5a}$ and $R^{5b}$ independently represent $C_{1-6}$ alkyl which group may be optionally substituted by one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, oxo, and carboxy; or $R^{5a}$ and $R^{5b}$ when taken together with the carbon to which they are attached represent a carbonyl, thiocarbonyl or —C═N—OH; and $R^6$ represents hydrogen, hydroxy, halogen, or trifluoromethyl; or $R^6$ and Y together with the carbon to which they are attached form a $C_{3-7}$ cycloalkyl or $C_{3-7}$ heterocycloalkyl, optionally substituted by halogen; and $R^a$ represents $C_{1-6}$ alkylaryl($C_{1-6}$)alkyl, or heteroaryl($C_{1-6}$)alkyl, any of which groups may be optionally substituted by $C_{1-6}$ alkoxy or oxo;

$R^b$ represents hydrogen or $R^b$ represents $C_{1-6}$ alkyl, aryl($C_{1-6}$)alkyl, $C_{3-7}$ heterocycloalkyl, and $C_{3-7}$ heterocycloalkyl($C_{1-6}$)alkyl, any of which groups may be optionally substituted by one or more substituents selected from $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino;

$R^c$ represents hydrogen or $R^c$ represents $C_{1-6}$ alkyl, $C_{3-7}$ cycloalkyl, or $C_{3-7}$ heterocycloalkyl, any of which groups may be optionally substituted by $C_{2-6}$ alkylcarbonyl or $C_{2-6}$ alkoxycarbonyl; and $R^d$ represents hydrogen or $R^d$ represents $C_{1-6}$ alkyl, aryl, or heteroaryl, either of which groups may be optionally substituted by one or more substituents selected from halogen, $C_{1-6}$ alkyl, $C_{1-6}$ alkoxy, oxo, $C_{2-6}$ alkylcarbonyloxy and di($C_{1-6}$)alkylamino.

2. The compound as claimed in claim 1, represented by formula (IIA), or a pharmaceutically acceptable salt thereof,

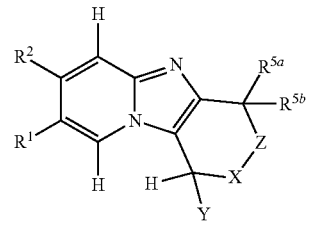

(IIA)

wherein
$R^2$ represents hydrogen, halogen, trifluoromethyl, or cyano; or $R^2$ represents an optionally substituted $C_{1-6}$ alkyl optionally substituted by $C_{2-6}$ alkoxycarbonyl;

X is oxygen or —$NR^d$;

Z represents a straight or branched $C_{1-4}$ alkylene chain optionally substituted by one or more substituents selected from halogen, hydroxy, oxo, $C_{1-6}$ alkoxy, aryl, —$C(O)R^d$, —$CO_2R^d$, —$CONR^bR^c$—$S(O)(N$—$R^d)R^a$, or —$SO_2NR^bR^c$;

$R^{5a}$ represents hydrogen, hydroxy, halogen, trifluoromethyl, cyano; —$NR^bR^c$, —$S(O)_2R^a$, —$OR^a$, or —$O(CO)$—$R^d$—; or $R^{5a}$ represents $C_{1-6}$ alkyl, which group may be optionally substituted by one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$) alkylsulphonyl($C_{1-6}$)alkyl, di($C_{1-6}$)alkylaminocarbonyl, oxo, and carboxy; and $R^{5b}$ represents hydrogen, hydroxy, halogen, cyano, or trifluoromethyl; or $R^{5b}$ represents $C_{1-6}$ alkyl, any of which groups may be optionally substituted by one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, oxo, and carboxy; or $R^{5a}$ and $R^{5b}$ when taken together with the carbon to which they are attached represent a carbonyl, thiocarbonyl, or —C═N—OH.

3. The compound as claimed in claim 2, represented by formula (IIB) or formula (IIN), or a pharmaceutically acceptable salt thereof,

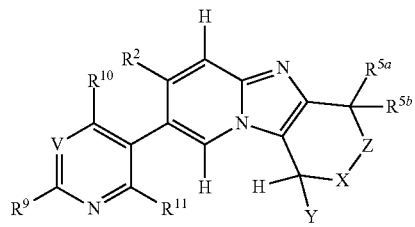

(IIB)

wherein
V represents C—$R^{12}$ or N;
$R^9$ represents hydrogen, halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, aryl-sulphonyl, ($C_{1-6}$)alkylsulphonyl ($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$) alkylamino, N—[($C_{1-6}$)alkyl]-N-[hydroxy($C_{1-6}$) alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$) alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$) alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl ($C_{1-6}$)alkoxycarbonyl, $C_{2-6}$ alkoxycarbonylmethylidenyl, aminocarbonyl, di($C_{1-6}$) alkylaminocarbonyl, aminosulphonyl, ($C_{1-6}$) alkylsulphoximinyl or [($C_{1-6}$)alkyl][N—($C_{1-6}$)alkyl] sulphoximinyl; or $R^9$ represents ($C_{3-7}$)cycloalkyl, ($C_{3-7}$)heterocycloalkyl, or heteroaryl, any of which groups may be optionally substituted by one or more substituents selected from cyano, trifluoromethyl, hydroxy, $C_{1-6}$ alkyl, $C_{1-6}$ alkoxy, $C_{1-6}$ alkylsulphonyl, ($C_{1-6}$)alkylsulphoximinyl, $C_{1-6}$ alkylcarbonyl, $C_{1-6}$ alkoxycarbonyl, oxo and carboxy;

$R^{10}$ and $R^{11}$ independently represents hydrogen, halogen, cyano, trifluoromethyl, hydroxy; —$NR^bR^c$, —$OR^a$, $C_{1-6}$ alkyl, or $C_{1-6}$ alkylsulphonyl; and $R^{12}$ represents hydrogen, halogen or $C_{1-6}$ alkyl.

4. The compound as claimed in claim 1 represented by formula (IIP), (IIQ), (IIS), or (IIT), or a pharmaceutically acceptable salt thereof,

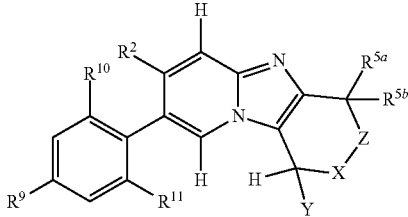

(IIN)

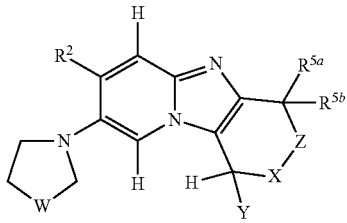

(IIP)

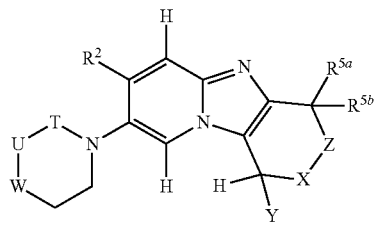

(IIQ)

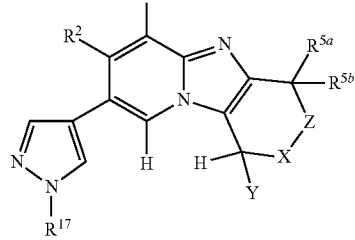

(IIS)

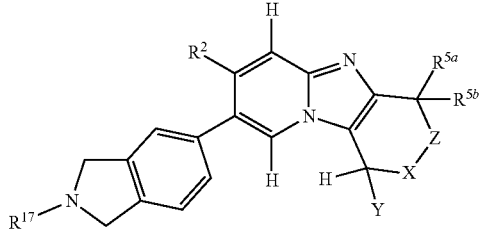

(IIT)

wherein
$R^{17}$ independently represents hydrogen, $C_{1-6}$ alkyl, $C_{1-6}$ alkylsulphonyl, $C_{1-6}$ alkylsulphonylalkyl, trifluoromethyl or $C_{2-6}$ alkoxycarbonyl;

X is oxygen or —$NR^d$;

Z represents a straight or branched $C_{1-4}$ alkylene chain optionally substituted by one or more substituents selected from halogen, hydroxy, oxo, $C_{1-6}$ alkoxy, aryl, —$C(O)R^d$, —$CO_2R^d$, —$CONR^bR^c$—$S(O)(N$—$R^d)R^a$, or —$SO_2NR^bR^c$;

$R^{5a}$ represents hydrogen, hydroxy, halogen, trifluoromethyl, cyano; —$NR^bR^c$, —$S(O)_2R^a$, —$OR^a$, or —$O(CO)$—$R^d$—; or $R^{5a}$ represents $C_{1-6}$ alkyl, which group may be optionally substituted by one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$) alkylsulphonyl($C_{1-6}$)alkyl, di($C_{1-6}$)alkylaminocarbonyl, oxo, and carboxy;

$R^{5b}$ represents hydrogen, hydroxy, halogen, cyano, or trifluoromethyl; or $R^{5b}$ represents $C_{1-6}$ alkyl, any of which groups may be optionally substituted by one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, ($C_{3-7}$)cycloalkyl, $C_{1-6}$ alkylsulphonyl, ($C_{1-6}$)alkylsulphonyl($C_{1-6}$)alkyl, di($C_{1-6}$)alkylaminocarbonyl, oxo, and carboxy; or $R^{5a}$ and $R^{5b}$ when taken together with the carbon to which they are attached represent a carbonyl, thiocarbonyl, or —C=N—OH;

$R^2$ represents hydrogen, halogen, trifluoromethyl, or cyano; or $R^2$ represents an optionally substituted $C_{1-6}$ alkyl optionally substituted by $C_{2-6}$ alkoxycarbonyl;

T represents —$CH_2$— or —$CH_2CH_2$;

U represents C(O) or S(O)$_2$;

W represents O, N($R^{14}$), or C($R^{15}$)($R^{16}$);

$R^{14}$ represents hydrogen, $C_{1-6}$ alkyl, or $C_{2-6}$ alkylcarbonyl;

$R^{15}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)

alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$)alkoxyaminocarbonyl, tetrazolyl or hydroxyoxadiazolyl;

$R^{16}$ represents hydrogen, halogen or $C_{1-6}$ alkyl.

5. The compound as claimed in claim 3 wherein, $R^9$ represents ($C_{1-6}$)alkyl, halo($C_{1-6}$)alkyl, (hydroxy)$C_{1-6}$ alkyl, $C_{1-6}$ alkoxy, arylsulphonyl, $C_{1-6}$ alkylsulphonyl, ($C_{1-6}$)alkylsulphonyl($C_{1-6}$)alkyl, $C_{2-6}$ alkylcarbonylamino($C_{1-6}$)alkyl, ($C_{1-6}$)alkylsulphoximinyl, carboxy, oxo, or $C_{2-6}$ alkyloxycarbonyl; or $R^9$ represents ($C_{3-7}$)cycloalkyl, ($C_{3-7}$)heterocloalkyl, or heteroaryl, any of which groups may be optionally substituted by one or more substituents selected from cyano, trifluoromethyl, hydroxy, $C_{1-6}$ alkyl, $C_{1-6}$ alkoxy, $C_{1-6}$ alkylsulphonyl, ($C_{1-6}$)alkylsulphoximinyl, $C_{1-6}$ alkylcarbonyl, $C_{1-6}$ alkoxycarbonyl, oxo and carboxy.

6. The compound as claimed in claim 1 represented by formula (IIW), or a pharmaceutically acceptable salt thereof,

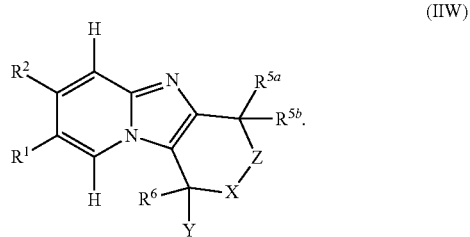

(IIW)

7. The compound as claimed in claim 1 wherein X represents an oxygen atom.

8. The compound as claimed in claim 1 wherein Z represents a methylene group.

9. The compound as claimed in claim 1 wherein Y represents an optionally substituted aryl.

10. The compound as claimed in claim 1 wherein Y represents 2-difluoromethoxy-phenyl.

11. The compound as claimed in claim 1 wherein $R^2$ represents hydrogen or halogen.

12. The compound according to claim 1 wherein $R^{5a}$ represents hydroxyl or hydrogen.

13. The compound as claimed in claim 1, wherein $R^{5b}$ represents hydrogen or methyl.

14. A compound that is
1-[2-(difluoromethoxy)phenyl]-8-(6-methoxypyridin-3-yl)-3,4-dihydro-1H-pyrano[4',3':4,5]imidazo[1,2-a]pyridine;
1-[2-(difluoromethoxy)phenyl]-8-[2-(morpholin-4-yl)pyrimidin-5-yl]-3,4-dihydro-1H-pyrano[4',3':4,5]imidazo[1,2-a]pyridine;
1-[2-(difluoromethoxy)phenyl]-8-[2-(morpholin-4-yl)pyrimidin-5-yl]-1,2,3,4-tetrahydroimidazo[1,2-a:5,4-c']dipyridine;
1-[2-(difluoromethoxy)phenyl]-8-(6-methoxypyridin-3-yl)-1,2,3,4-tetrahydroimidazo[1,2-a:5,4-c']dipyridine;
8-(6-methoxypyridin-3-yl)-1-phenyl-1,2,3,4-tetrahydroimidazo[1,2-a:5,4-c']dipyridine;
(1S)-1-[2-(difluoromethoxy)phenyl]-8-[4-(methylsulfonyl)phenyl]-1,2,3,4-tetrahydroimidazo[1,2-a:5,4-c']dipyridine;
(1R)-1-[2-(difluoromethoxy)phenyl]-8-[4-(methylsulfonyl)phenyl]-1,2,3,4-tetrahydroimidazo[1,2-a:5,4-c']dipyridine;
4-{5-[(R)-4-(2-difluoromethoxy-phenyl)-7-fluoro-1,4-dihydro-2H-3-oxa-4b,9-diaza-fluoren-6-yl]-pyridin-2-yl}-piperazine-1-carboxylic acid tert-butyl ester;
(1R)-1-[2-(difluoromethoxy)phenyl]-7-fluoro-8-[6-(piperazin-1-yl)pyridin-3-yl]-3,4-dihydro-1H-pyrano[4',3':4,5]imidazo[1,2-a]pyridine;
4-{5-[(S)-4-(2-difluoromethoxy-phenyl)-7-fluoro-1,4-dihydro-2H-3-oxa-4b,9-diaza-fluoren-6-yl]-pyridin-2-yl}-piperazine-1-carboxylic acid tert-butyl ester;
(1S)-1-[2-(difluoromethoxy)phenyl]-7-fluoro-8-[6-(piperazin-1-yl)pyridin-3-yl]-3,4-dihydro-1H-pyrano[4',3':4,5]imidazo[1,2-a]pyridine;
(1R or S)-1-[2-(difluoromethoxy)phenyl]-7-fluoro-8-[4-(methylsulfonyl)phenyl]-3,4-dihydro-1H-pyrano[4',3':4,5]imidazo[1,2-a]pyridine;
(1R or S)-8-(6-cyclopropylpyridin-3-yl)-1-[2-(difluoromethoxy)phenyl]-7-fluoro-3,4-dihydro-1H-pyrano[4',3':4,5]imidazo[1,2-a]pyridine;
(1R or S)-1-[2-(difluoromethoxy)phenyl]-7-fluoro-8-[6-(methylsulfonyl)pyridin-3-yl]-3,4-dihydro-1H-pyrano[4',3':4,5]imidazo[1,2-a]pyridine;
(1R or S)-8-(1-cyclopropyl-1H-pyrazol-4-yl)-1-[2-(difluoromethoxy)phenyl]-7-fluoro-3,4-dihydro-1H-pyrano[4',3':4,5]imidazo[1,2-a]pyridine;
(1R or S)-1-[2-(difluoromethoxy)phenyl]-7-fluoro-8-[1-(phenylsulfonyl)-1H-pyrazol-4-yl]-3,4-dihydro-1H-pyrano[4',3':4,5]imidazo[1,2-a]pyridine;
N-(4-{(1R or S)-1-[2-(difluoromethoxy)phenyl]-7-fluoro-3,4-dihydro-1H-pyrano[4',3':4,5]imidazo[1,2-a]pyridin-8-yl}benzyl)acetamide;
tert-butyl 5-{(1R or S)-1-[2-(difluoromethoxy)phenyl]-7-fluoro-3,4-dihydro-1H-pyrano[4',3':4,5]imidazo[1,2-a]pyridin-8-yl}-1,3-dihydro-2H-isoindole-2-carboxylate;
4-{(1R or S)-1-[2-(difluoromethoxy)phenyl]-7-fluoro-3,4-dihydro-1H-pyrano[4',3':4,5]imidazo[1,2-a]pyridin-8-yl}benzonitrile;
(1R or S)-1-[2-(difluoromethoxy)phenyl]-7-fluoro-8-(1H-pyrazol-4-yl)-3,4-dihydro-1H-pyrano[4',3':4,5]imidazo[1,2-a]pyridine;
(1R or S)-1-[2-(difluoromethoxy)phenyl]-7-fluoro-8-{4-[(methylsulfonyl)methyl]phenyl}-3,4-dihydro-1H-pyrano[4',3':4,5]imidazo[1,2-a]pyridine;
(5-{(1R or S)-1-[2-(difluoromethoxy)phenyl]-7-fluoro-3,4-dihydro-1H-pyrano[4',3':4,5]imidazo[1,2-a]pyridin-8-yl}pyridin-2-yl)methanol;
difluoromethyl 2-{8-[1-(phenylsulfonyl)-1H-pyrazol-4-yl]-3,4-dihydro-1H-pyrano[4',3':4,5]imidazo[1,2-a]pyridin-1-yl}phenyl ether;
methyl 1-(5-{1-[2-(difluoromethoxy)phenyl]-3,4-dihydro-1H-pyrano[4',3':4,5]imidazo[1,2-a]pyridin-8-yl}pyrimidin-2-yl)piperidine-4-carboxylate;
1-(5-{(4R)-1-[2-(difluoromethoxy)phenyl]-7-fluoro-3,4-dihydro-1H-pyrano[4',3':4,5]imidazo[1,2-a]pyridin-8-yl}pyrimidin-2-yl)-4-methylpiperidine-4-carboxylic acid ethyl ester;
1-(5-{(4S)-1-[2-(difluoromethoxy)phenyl]-7-fluoro-3,4-dihydro-1H-pyrano[4',3':4,5]imidazo[1,2-a]pyridin-8-yl}pyrimidin-2-yl)-4-methylpiperidine-4-carboxylic acid ethyl ester;
8-(6-methoxypyridin-3-yl)-1-phenyl-3,4-dihydro-1H-pyrano[4',3':4,5]imidazo[1,2-a]pyridine;
(4S or R)-1-[2-(difluoromethoxy)phenyl]-7-fluoro-8-[3-(methylsulfonyl)phenyl]-3,4-dihydro-1H-pyrano[4',3':4,5]imidazo[1,2-a]pyridine;
(4S or R)-1-[2-(difluoromethoxy)phenyl]-7-fluoro-8-[2-(methylsulfonyl)pyridin-4-yl]-3,4-dihydro-1H-pyrano[4',3':4,5]imidazo[1,2-a]pyridine;

(4S)-8-fluoro-7-[4-(methylsulfonyl)phenyl]-4-phenyl-3,4-dihydro-1H-pyrano[3',4':4,5]imidazo[1,2-a]pyridine;

(4R)-8-fluoro-7-[4-(methylsulfonyl)phenyl]-4-phenyl-3,4-dihydro-1H-pyrano[3',4':4,5]imidazo[1,2-a]pyridine;

(1S,4S)-1-[2-(difluoromethoxy)phenyl]-7-fluoro-8-[6-(tetrahydro-2H-pyran-4-yl)pyridin-3-yl]-3,4-dihydro-1H-pyrano[4',3':4,5]imidazo[1,2-a]pyridin-4-ol;

(1S,4R)-1-[2-(difluoromethoxy)phenyl]-7-fluoro-8-[6-(tetrahydro-2H-pyran-4-yl)pyridin-3-yl]-3,4-dihydro-1H-pyrano[4',3':4,5]imidazo[1,2-a]pyridin-4-ol;

N-(4-{(1S or R)-1-[2-(difluoromethoxy)phenyl]-7-fluoro-3,4-dihydro-1H-pyrano[4',3':4,5]imidazo[1,2-a]pyridin-8-yl}benzyl)-N-methylacetamide;

(1S or R)-8-(2-cyclopropylpyrimidin-5-yl)-1-[2-(difluoromethoxy)phenyl]-7-fluoro-3,4-dihydro-1H-pyrano[4',3':4,5]imidazo[1,2-a]pyridine;

(1R or S)-1-[2-(difluoromethoxy)phenyl]-7-fluoro-8-[4-(5-methyl-1H-1,2,4-triazol-3-yl)phenyl]-3,4-dihydro-1H-pyrano[4',3':4,5]imidazo[1,2-a]pyridine;

(1R or S)-1-[2-(difluoromethoxy)phenyl]-7-fluoro-8-[1-(methylsulfonyl)-1H-pyrazol-4-yl]-3,4-dihydro-1H-pyrano[4',3':4,5]imidazo[1,2-a]pyridine;

(1R or S)-1-[2-(difluoromethoxy)phenyl]-8-(2,3-dihydro-1H-isoindol-5-yl)-7-fluoro-3,4-dihydro-1H-pyrano[4',3':4,5]imidazo[1,2-a]pyridine;

(1R or S)-1-[2-(difluoromethoxy)phenyl]-7-fluoro-8-[2-(methylsulfonyl)-2,3-dihydro-1H-isoindol-5-yl]-3,4-dihydro-1H-pyrano[4',3':4,5]imidazo[1,2-a]pyridine;

(1R or S)-1-[2-(difluoromethoxy)phenyl]-7-fluoro-8-{1-[2-(methylsulfonyl)ethyl]-1H-pyrazol-4-yl}-3,4-dihydro-1H-pyrano[4',3':4,5]imidazo[1,2-a]pyridine;

(1R or S)-1-[2-(difluoromethoxy)phenyl]-8-[1-(1,1-dioxidotetrahydrothiophen-3-yl)-1H-pyrazol-4-yl]-7-fluoro-3,4-dihydro-1H-pyrano[4',3':4,5]imidazo[1,2-a]pyridine;

(1R or S)-1-[2-(difluoromethoxy)phenyl]-7-fluoro-8-{6-[(methylsulfonyl)methyl]pyridin-3-yl}-3,4-dihydro-1H-pyrano[4',3':4,5]imidazo[1,2-a]pyridine;

1-[2-(difluoromethoxy)phenyl]-8-(4-methoxypiperidin-1-yl)-3,4-dihydro-1H-pyrano[4',3':4,5]imidazo[1,2-a]pyridine;

1-[2-(difluoromethoxy)phenyl]-8-[4-(methylsulfonyl)piperazin-1-yl]-3,4-dihydro-1H-pyrano[4',3':4,5]imidazo[1,2-a]pyridine;

1-[2-(difluoromethoxy)phenyl]-8-(3-methoxyazetidin-1-yl)-3,4-dihydro-1H-pyrano[4',3':4,5]imidazo[1,2-a]pyridine;

1-[2-(difluoromethoxy)phenyl]-8-[3-methoxypyrrolidin-1-yl]-3,4-dihydro-1H-pyrano[4',3':4,5]imidazo[1,2-a]pyridine;

1-[2-(difluoromethoxy)phenyl]-8-(1H-pyrazol-4-yl)-3,4-dihydro-1H-pyrano[4',3':4,5]imidazo[1,2-a]pyridine;

1-(5-{(1-[2-(difluoromethoxy)phenyl]-3,4-dihydro-1H-pyrano[4',3':4,5]imidazo[1,2-a]pyridin-8-yl}pyrimidin-2-yl)piperidine-4-carboxylic acid;

1-(5-{(1R)-1-[2-(difluoromethoxy)phenyl]7-fluoro-3,4-dihydro-1H-pyrano[4',3':4,5]imidazo[1,2-a]pyridin-8-yl}pyrimidin-2-yl)-4-methylpiperidine-4-carboxylic acid;

1-(5-{(1S)-1-[2-(difluoromethoxy)phenyl]7-fluoro-3,4-dihydro-1H-pyrano[4',3':4,5]imidazo[1,2-a]pyridin-8-yl}pyrimidin-2-yl)-4-methylpiperidine-4-carboxylic acid;

1-(5-chloro-2-methylthiazol-4-yl)-7-fluoro-8-(2-morpholinopyrimidin-5-yl)-3,4-dihydro-1H-pyrano[4',3':4,5]imidazo[1,2-a]pyridine;

1-(5-chloro-2-(difluoromethoxy)phenyl)-7-fluoro-8-(2-morpholinopyrimidin-5-yl)-3,4-dihydro-1H-pyrano[4',3':4,5]imidazo[1,2-a]pyridine;

1-(5-chloro-2-(trifluoromethoxy)phenyl)-7-fluoro-8-(2-morpholinopyrimidin-5-yl)-3,4-dihydro-1H-pyrano[4',3':4,5]imidazo[1,2-a]pyridine;

1-(2-chlorophenyl)-7-fluoro-8-(2-morpholinopyrimidin-5-yl)-3,4-dihydro-1H-pyrano[4',3':4,5]imidazo[1,2-a]pyridine;

1-(3-chlorophenyl)-7-fluoro-8-(2-morpholinopyrimidin-5-yl)-3,4-dihydro-1H-pyrano[4',3':4,5]imidazo[1,2-a]pyridine;

1-(3-(difluoromethoxy)phenyl)-7-fluoro-8-(2-morpholinopyrimidin-5-yl)-3,4-dihydro-1H-pyrano[4',3':4,5]imidazo[1,2-a]pyridine;

1-(2,5-dimethylphenyl)-7-fluoro-8-(2-morpholinopyrimidin-5-yl)-3,4-dihydro-1H-pyrano[4',3':4,5]imidazo[1,2-a]pyridine;

1-(2,5-dichlorophenyl)-7-fluoro-8-(2-morpholinopyrimidin-5-yl)-3,4-dihydro-1H-pyrano[4',3':4,5]imidazo[1,2-a]pyridine;

1-(2-chloro-6-(difluoromethoxy)phenyl)-7-fluoro-8-(2-morpholinopyrimidin-5-yl)-3,4-dihydro-1H-pyrano[4',3':4,5]imidazo[1,2-a]pyridine;

7-fluoro-8-(2-morpholinopyrimidin-5-yl)-1-(2-(trifluoromethoxy)phenyl)-3,4-dihydro-1H-pyrano[4',3':4,5]imidazo[1,2-a]pyridine;

1-(2-chloro-6-(trifluoromethoxy)phenyl)-7-fluoro-8-(2-morpholinopyrimidin-5-yl)-3,4-dihydro-1H-pyrano[4',3':4,5]imidazo[1,2-a]pyridine;

7-fluoro-8-(2-morpholinopyrimidin-5-yl)-1-(2-(trifluoromethyl)phenyl)-3,4-dihydro-1H-pyrano[4',3':4,5]imidazo[1,2-a]pyridine;

1-(2,5-bis(difluoromethoxy)phenyl)-7-fluoro-8-(2-morpholinopyrimidin-5-yl)-3,4-dihydro-1H-pyrano[4',3':4,5]imidazo[1,2-a]pyridine;

1-(2-(difluoromethoxy)-5-fluorophenyl)-7-fluoro-8-(2-morpholinopyrimidin-5-yl)-3,4-dihydro-1H-pyrano[4',3':4,5]imidazo[1,2-a]pyridine;

1-(2-(difluoromethoxy)-3,5-difluorophenyl)-7-fluoro-8-(2-morpholinopyrimidin-5-yl)-3,4-dihydro-1H-pyrano[4',3':4,5]imidazo[1,2-a]pyridine;

1-(2-(difluoromethoxy)-3-fluorophenyl)-7-fluoro-8-(2-morpholinopyrimidin-5-yl)-3,4-dihydro-1H-pyrano[4',3':4,5]imidazo[1,2-a]pyridine;

1-(2-chloro-5-fluorophenyl)-7-fluoro-8-(2-morpholinopyrimidin-5-yl)-3,4-dihydro-1H-pyrano[4',3':4,5]imidazo[1,2-a]pyridine;

1-(5-chloro-2-fluorophenyl)-7-fluoro-8-(2-morpholinopyrimidin-5-yl)-3,4-dihydro-1H-pyrano[4',3':4,5]imidazo[1,2-a]pyridine;

1-(4,6-dimethoxypyrimidin-5-yl)-7-fluoro-8-(2-morpholinopyrimidin-5-yl)-3,4-dihydro-1H-pyrano[4',3':4,5]imidazo[1,2-a]pyridine;

7-fluoro-1-(2-methyl-4-(trifluoromethyl)thiazol-5-yl)-8-(2-morpholinopyrimidin-5-yl)-3,4-dihydro-1H-pyrano[4',3':4,5]imidazo[1,2-a]pyridine;

1-[4-(difluoromethoxy)phenyl]-7-fluoro-8-[2-(morpholin-4-yl)pyrimidin-5-yl]-3,4-dihydro-1H-pyrano[4',3':4,5]imidazo[1,2-a]pyridine;

1-(4-chlorophenyl)-7-fluoro-8-[2-(morpholin-4-yl)pyrimidin-5-yl]-3,4-dihydro-1H-pyrano[4',3':4,5]imidazo[1,2-a]pyridine;

3-{7-fluoro-8-[2-(morpholin-4-yl)pyrimidin-5-yl]-3,4-dihydro-1H-pyrano[4',3':4,5]imidazo[1,2-a]pyridin-1-yl}benzonitrile;

7-fluoro-1-(4-methyl-1,3-thiazol-5-yl)-8-[2-(morpholin-4-yl)pyrimidin-5-yl]-3,4-dihydro-1H-pyrano[4',3':4,5]imidazo[1,2-a]pyridine;

1-(2,4-dimethyl-1,3-thiazol-5-yl)-7-fluoro-8-[2-(morpholin-4-yl)pyrimidin-5-yl]-3,4-dihydro-1H-pyrano[4',3':4,5]imidazo[1,2-a]pyridine;

4-{7-fluoro-8-[2-(morpholin-4-yl)pyrimidin-5-yl]-3,4-dihydro-1H-pyrano[4',3':4,5]imidazo[1,2-a]pyridin-1-yl}benzonitrile;

2-{7-fluoro-8-[2-(morpholin-4-yl)pyrimidin-5-yl]-3,4-dihydro-1H-pyrano[4',3':4,5]imidazo[1,2-a]pyridin-1-yl}benzonitrile;

7-fluoro-1-(5-methoxypyrazin-2-yl)-8-[2-(morpholin-4-yl)pyrimidin-5-yl]-3,4-dihydro-1H-pyrano[4',3':4,5]imidazo[1,2-a]pyridine;

7-fluoro-1-[4-(methyl sulfonyl)phenyl]-8-[2-(morpholin-4-yl)pyrimidin-5-yl]-3,4-dihydro-1H-pyrano[4',3':4,5]imidazo[1,2-a]pyridine;

6-chloro-7'-fluoro-8'-[2-(morpholin-4-yl)pyrimidin-5-yl]-2,3,3',4'-tetrahydrospiro[indene-1,1'-pyrano[4',3':4,5]imidazo[1,2-a]pyridine;

1-(4-chloro-1,3-thiazol-5-yl)-7-fluoro-8-[2-(morpholin-4-yl)pyrimidin-5-yl]-3,4-dihydro-1H-pyrano[4',3':4,5]imidazo[1,2-a]pyridine;

2-(6-methoxypyridin-3-yl)-10-phenyl-7,8,9,10-tetrahydro-6H-cyclohepta[4,5]imidazo[1,2-a]pyridin-10-ol;

(1R or S,4S or R)-1-[2-(difluoromethoxy)phenyl]-7-fluoro-8-[4-(methylsulfonyl)phenyl]-3,4-dihydro-1H-pyrano[4',3':4,5]imidazo[1,2-a]pyridin-4-ol;

2-(4-{(1R,4S)-1-[5-chloro-2-(difluoromethoxy)phenyl]-7-fluoro-4-hydroxy-3,4-dihydro-1H-pyrano[4',3':4,5]imidazo[1,2-a]pyridin-8-yl}phenyl)-2-methylpropanenitrile;

2-(4-{(1S,4S)-1-[5-chloro-2-(difluoromethoxy)phenyl]-7-fluoro-4-hydroxy-3,4-dihydro-1H-pyrano[4',3':4,5]imidazo[1,2-a]pyridin-8-yl}phenyl)-2-methylpropanenitrile;

(1R,4S)-1-[2-(difluoromethoxy)phenyl]-7-fluoro-8-[2-(tetrahydro-2H-pyran-4-yl)pyrimidin-5-yl]-3,4-dihydro-1H-pyrano[4',3':4,5]imidazo[1,2-a]pyridin-4-ol;

(1S,4S)-1-[2-(difluoromethoxy)phenyl]-7-fluoro-8-[2-(tetrahydro-2H-pyran-4-yl)pyrimidin-5-yl]-3,4-dihydro-1H-pyrano[4',3':4,5]imidazo[1,2-a]pyridin-4-ol;

2-(5-{(1R)-1-[2-(difluoromethoxy)phenyl]-7-fluoro-3,4-dihydro-1H-pyrano[4',3':4,5]imidazo[1,2-a]pyridin-8-yl}pyrimidin-2-yl)propan-2-ol;

(1R)-1-[2-(difluoromethoxy)phenyl]-7-fluoro-8-[2-(2-fluoropropan-2-yl)pyrimidin-5-yl]-3,4-dihydro-1H-pyrano[4',3':4,5]imidazo[1,2-a]pyridine; or (4R or S)-4-[2-(difluoromethoxy)phenyl]-7-[6-(methylsulfonyl)pyridin-3-yl]-3,4-dihydroimidazo[1,2-a:4,5-c']dipyridin-1(2H)-one and (4S or R)-4-[2-(difluoromethoxy)phenyl]-7-[6-(methylsulfonyl)pyridin-3-yl]-3,4-dihydroimidazo[1,2-a:4,5-c']dipyridin-1(2H)-one.

15. A pharmaceutical composition comprising a compound of formula (I) as defined in claim 1 or an N-oxide thereof, or a pharmaceutically acceptable salt thereof, in association with a pharmaceutically acceptable carrier.

16. A method of treating rheumatoid arthritis, psoriasis, or inflammatory bowel disease, which method comprises administering to a patient in need of such treatment an effective amount of a compound of formula (I), as defined in claim 1 or a pharmaceutically acceptable salt thereof.

* * * * *